(12) United States Patent
Abeyratne et al.

(10) Patent No.: US 10,098,569 B2
(45) Date of Patent: Oct. 16, 2018

(54) METHOD AND APPARATUS FOR PROCESSING PATIENT SOUNDS

(71) Applicant: THE UNIVERSITY OF QUEENSLAND, St. Lucia, Queensland (AU)

(72) Inventors: Udantha R. Abeyratne, St. Lucia (AU); Vinayak Swarnkar, St. Lucia (AU); Yusuf A. Amrulloh, St. Lucia (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 14/389,291

(22) PCT Filed: Mar. 28, 2013

(86) PCT No.: PCT/AU2013/000323
§ 371 (c)(1),
(2) Date: Sep. 29, 2014

(87) PCT Pub. No.: WO2013/142908
PCT Pub. Date: Oct. 3, 2013

(65) Prior Publication Data
US 2015/0073306 A1   Mar. 12, 2015

(30) Foreign Application Priority Data

Mar. 29, 2012  (AU) .................................. 2012901255

(51) Int. Cl.
*A61B 7/00* (2006.01)
*A61B 5/08* (2006.01)
(Continued)

(52) U.S. Cl.
CPC ............ *A61B 5/0823* (2013.01); *A61B 5/742* (2013.01); *A61B 7/003* (2013.01); *A61B 7/04* (2013.01);
(Continued)

(58) Field of Classification Search
CPC ... A61B 5/0823; A61B 5/0803; A61B 5/7264; A61B 7/003; A61B 7/04; G06F 19/3431; G06F 19/345
See application file for complete search history.

(56) References Cited

U.S. PATENT DOCUMENTS 5,598,508 A * 1/1997 Goldman ............. A61B 5/0803
706/20
6,436,057 B1 8/2002 Goldsmith et al.
(Continued)

FOREIGN PATENT DOCUMENTS

EP   1 932 473   6/2008
JP   2003-038460   2/2003
(Continued)

OTHER PUBLICATIONS

Drugman et al., "Assessment of audio features for automatic cough detection." Signal Processing Conference, 2011 19th European. IEEE, 2011.*
(Continued)

*Primary Examiner* — Devin Henson
(74) *Attorney, Agent, or Firm* — Nixon & Vanderhye PC

(57) ABSTRACT

A method of operating a computational device to process patient sounds, the method comprises the steps of: extracting features from segments of said patient sounds; and classifying the segments as cough or non-cough sounds based upon the extracted features and predetermined criteria; and presenting a diagnosis of a disease related state on a display
(Continued)

under control of the computational device based on segments of the patient sounds classified as cough sounds.

19 Claims, 22 Drawing Sheets

(51) Int. Cl.

| | | |
|---|---|---|
| *A61B 7/04* | (2006.01) | |
| *G06K 9/00* | (2006.01) | |
| *G10L 25/66* | (2013.01) | |
| *G16H 50/30* | (2018.01) | |
| *G16H 50/20* | (2018.01) | |
| *A61B 5/00* | (2006.01) | |
| *G10L 25/30* | (2013.01) | |

(52) U.S. Cl.
CPC ..... *G06K 9/00523* (2013.01); *G06K 9/00536* (2013.01); *G10L 25/66* (2013.01); *G16H 50/20* (2018.01); *G16H 50/30* (2018.01); *A61B 5/0803* (2013.01); *A61B 5/7264* (2013.01); *G10L 25/30* (2013.01); *Y02A 90/26* (2018.01)

(56) References Cited

U.S. PATENT DOCUMENTS

| | | | | |
|---|---|---|---|---|
| 6,443,907 | B1* | 9/2002 | Mansy | A61B 7/04 |
| | | | | 600/529 |
| 2008/0082017 | A1* | 4/2008 | Savic | A61B 7/003 |
| | | | | 600/529 |
| 2008/0082018 | A1 | 4/2008 | Sackner et al. | |
| 2011/0087079 | A1* | 4/2011 | Aarts | A61B 7/003 |
| | | | | 600/300 |
| 2011/0125044 | A1 | 5/2011 | Rhee et al. | |
| 2012/0071777 | A1* | 3/2012 | MacAuslan | A61B 5/0823 |
| | | | | 600/529 |
| 2012/0265024 | A1* | 10/2012 | Shrivastav | A61B 5/40 |
| | | | | 600/300 |

FOREIGN PATENT DOCUMENTS

| | | | | |
|---|---|---|---|---|
| JP | 2008-506423 | | 3/2008 | |
| JP | 2008-178635 | | 8/2008 | |
| JP | 2011-167524 | | 9/2011 | |
| WO | WO 2008/152433 | | 12/2008 | |
| WO | WO 2010066008 | A1* | 6/2010 | A61B 7/003 |

OTHER PUBLICATIONS

Taplidou et al., "Nonlinear characteristics of wheezes as seen in the wavelet higher-order spectra domain." EMBS Annual Conference, pp. 4506-4509, Aug.-Sep. 2006.*

International Search Report for PCT/AU2013/000323, dated Jun. 25, 2013.

Written Opinion for PCT/AU2013/000323, dated Jun. 25, 2013.

European Search Report and Search Opinion dated Dec. 1, 2015 in European Application No. 13768257.1, 10 pages.

Office Action dated Dec. 3, 2015 in Chinese Application No. 201380028268X (with translation), 6 pages.

Y.H. Hiew et al., "DSP Algorithm for Cough Identification and Counting," 2002 IEEE International Conference on Acoustics, Speech, and Signal Processing, May 13, 2002, pp. IV-3888-IV-3891.

Office Action dated Feb. 27, 2017 in corresponding Japanese Application No. 2015-502020 (with translation), 3 pages.

* cited by examiner

Histogram of sensitivity and specificities achieved for 200 training and testing datasets. Only selected features were used for LR model designing.

METHOD AND APPARATUS FOR PROCESSING PATIENT SOUNDS

This application is the U.S. national phase of International Application No. PCT/AU2013/000323, filed 28 Mar. 2013, which designated the U.S. and claims priority to AU Application No. 2012901255, filed 29 Mar. 2012, the entire contents of each of which are hereby incorporated by reference.

TECHNICAL FIELD

In a first aspect, the present invention relates to an automated method and an apparatus for detecting cough sounds of a patient. In a second aspect the present invention relates to a method and apparatus for diagnosing disease states from patient sounds such as cough sounds.

BACKGROUND ART

Any references to methods, apparatus or documents of the prior art are not to be taken as constituting any evidence or admission that they formed, or form part of the common general knowledge.

Cough is a defense mechanism of the body to clear the respiratory tract from foreign materials which is inhaled accidentally or produced internally by infections [1]. It is a common symptom in a range of respiratory diseases such as asthma and whooping cough (pertussis) as well as pneumonia, which is the leading cause of death in children under 5 years of age. It has been estimated [2] that pneumonia causes over 1.6 million deaths in this group per year, with more than 97% [3] of cases occurring in the developing world. The world health organization (WHO) also reported that in those countries, pertussis has became one of the major childhood morbidities with an estimated 50 million cases and 300,000 deaths every year [4].

Even though cough is common in respiratory diseases and considered an importance clinical symptom, there is no golden standard to assess it. In a typical consultation session, physicians may listen to several episodes of natural or voluntary coughs, to obtain qualitative information such as the "wetness" of a cough. Such qualitative information is extremely useful in diagnosis as well as the treatment of respiratory diseases. However, manual analysis suffers from operator bias and leads to subjective outcomes.

During the consultation session physicians may also seek quantitative information on coughs, such as the frequency of occurrence of cough events over a given time interval. This information can be used to determine the nature (e.g., acute, chronic) and the severity of coughs as well as to monitor the efficacy of treatment. However, to obtain this information, physicians heavily rely on subjective reports of patients or their carers. There is a great need for an automated device capable of counting the number of coughs, especially in childhood diseases. More importantly, technology capable of automatically extracting cough events from long pediatric recordings is needed in order to facilitate the diagnosis of diseases such as pneumonia, pertussis and asthma.

Several approaches have been taken to develop automated cough counting systems (e.g., Hull Automatic Cough Counter (HACC) [5], Leicester Cough Monitor (LCM) [6], LifeShirt [7], VitaloJAK [8], and PulmoTrack [9]). The performances of these devices are varied. The HACC claimed a sensitivity and specificity of (80%, 96%) [5]. The figures for LifeShirt, Pulmotrack, LCM, and Vitalojak are (78%, 99%), (94%, 96%), (85.7%, 99.9%), and (97.5%, 97.7%) respectively [6, 10-13]. They relied on sound intensity dependent techniques, making them susceptible to variations in recording conditions and the particular instruments used. To the best of the inventors' knowledge, none of these commercial devices have been tested on pediatric populations.

Cough recording on children, especially the younger ones, pose several additional challenges. Younger children are unable to produce voluntary coughs upon request. Any method targeting pediatric populations should be capable of using natural coughs recorded over a period of interest. In pediatric recordings, crying, vocalization, and grunting are found abundantly, intermixed with cough sounds. Consequently, technology developed for adults are unlikely to be optimal for use on children. Another issue in cough recording from children is the cough sound intensity variation. Diseases such as severe pediatric pneumonia can dramatically lower the amplitude of a cough sound. Even in healthy people, cough sounds can have a large dynamic range, covering loud coughs to the barely audible. This condition may make intensity-based techniques unreliable for field use. The performance will also depend on particular sound capturing equipment, calibration status, and measurement protocols used.

Existing commercial cough counting devices such as LifeShirt, Vitalojak, and Pulmotrack employ contact sensors. While the use of contact sensors may have some advantages, they also carry several drawbacks. The intervening musculature severely curtails the bandwidth of a cough recorded using contact sensors; free air systems are immune to this. Contact sensors, compared to non-contact (free-air) microphones are robust against background sound propagated through air. However, they are more vulnerable to sound conducted through tissue and bones; spurious rubbing sounds due to sensor movement can also be an issue. In infectious diseases, elaborate efforts are needed to avoid cross contamination of patients through contact instrumentation. Furthermore, in pediatric subjects, contact sensors can also be difficult to attach because of patient discomfort.

Cough sounds carry critically useful information on the state of the airways. However, the existing devices use method that can detect only the presence of events ("Cough Detection") but are unable to automatically extract cough events ("Cough Segmentation") for further analysis. Thus they are limited to the counting of coughs. Cough Segmentation requires, in addition to Cough Detection capabilities, the knowledge on the exact beginning as well as the end of each cough event. It is known that inter-cough gaps, the durations of the coughs, and the amplitude of coughs may carry information related to respiratory diseases [14].

One disease whose symptoms include coughing is pneumonia. Pneumonia is the leading killer of young children around the world. It accounts for more than 19% of under-five child deaths each year. It's a disease of poverty and is strongly related with malnutrition and poor healthcare facilities. As a result childhood pneumonia deaths are critically high in developing countries. Pneumonia is also a problem among the aged people throughout the world.

Pneumonia is defined as an infection in the lungs with accumulation of inflammatory cells and secretions in the alveoli. The common symptoms of the Pneumonia includes, cough, difficulty in breathing, fever, headaches, loss of appetite, runny nose, and wheezing. In severe pneumonia cases young infants struggle for breath and may suffer convulsions, skin pallor, unconsciousness, hypothermia and lethargy.

Pneumonia is a difficult disease to diagnose. Current methods of diagnosis include clinical examination (eg: physical signs, chest auscultation), bio-chemical testing (eg: sputum analysis, oxygen saturation) and medical imaging (eg: chest X-rays and in some cases X-ray CT).

What are the Problems with Current Diagnostic Method?

Chest X-ray (CXR) is considered as a commonly available reference standard for diagnosing pneumonia. However, it is not a golden standard. In early stages of the disease, or when the disease involves a part of the lung not easily seen in CXR, pneumonia can be difficult to diagnose using CXR alone. Moreover, sometimes CXR results can be misleading due to lung scarring or congestive heart failure, which can mimic pneumonia in CXR. Even though X-ray CT may provide better outcomes, they are not widely available even in tertiary care hospitals in developing countries. Sputum tests require laboratory cultures and can take a minimum 2-3 days making them too slow for initial diagnosis. A positive sputum test does not necessarily indicate the presence of pneumonia because many of the pathogens causing pneumonia are naturally present in the throats of healthy people. Therefore, sputum test is mainly done to check the sensitiveness of a particular antibiotic that has already been started on a patient. The clinical examination together with the chest auscultation via stethoscopes is the frontline approach used in the initial diagnosis of pneumonia in a clinical setting; X-ray may be used to confirm a diagnosis when available.

None of the methods described above are available for mass deployment in remote regions of the world where pneumonia is rampant. They are expensive, resource intensive and require trained medical professionals to perform them.

In order overcome this problem, World Health Organization (WHO) has developed a set of highly simplified guidelines [ ref. 3] to diagnose childhood pneumonia in resource poor and remote areas of the world. According to these, a child presenting with difficult breathing or cough is diagnosed with pneumonia if they have tachyponea (fast breathing). Fast breathing is defined as 60 breaths or more in infants less than 2 months, 50 breaths or more per minute for the infants between 2 months to 12 months and 40 breaths or more per minute for children age between 12 months to 5 year old [ref 3, 4]. Chest in-drawing, skin pallor and unconsciousness may indicate severe pneumonia and also belong in WHO Danger Signs. This system is easier to implement in the field and is designed to have a high sensitivity of diagnosis (about 90% patients with the disease are picked up). However, WHO guidelines suffer from poor specificity of diagnosis; a large number of patients without pneumonia are also picked up as having pneumonia. The specificity of WHO algorithm is known to be about 20%.

Though WHO guidelines have helped in reducing the mortality rate down to 1.6 million childhood deaths per annum, several problems remain with the method. Due to its low specificity[ref.6], a large number of non-pneumonic children are receiving antibiotics unnecessarily. This has resulted in treatment failures arising from community antibiotic resistance. In many pneumonia endemic regions diseases such as malaria are also common. Both pneumonia and malaria share symptoms of fever, fast breathing and cough, and WHO algorithm for pneumonia can lead to misdiagnosis and delay in treatment. Several other diseases/conditions (such as COPD, asthma, pulmonary edema, lung cancer etc), which do not require antibiotics, can present with similar clinical features to pneumonia.

To improve the specificity of the WHO criteria, Cardoso et al [ref 6] suggested including presence of fever to diagnose pneumonia. They showed that adding fever improves diagnostic specificity significantly (up to 50%). Several other researchers in the past have assessed the accuracy of the WHO criteria in childhood pneumonia diagnosis. Harari et al [ref 7] studied several variables including tachypnoea to determine which clinical signs best predict radiographic evidence of pneumonia, in 185 children. They reported sensitivity of 73% and 64% specificity in diagnosing pneumonia with only tachypnoea (respiratory rate (RR) 50≥breaths/min for kids<12 months and RR≥40 breaths/min if age 1 year or older) as predictor. When they added chest indrawing to tachypnoea sensitivity improved by 4% at the cost of specificity (dropped by 6%). Similarly with the other clinical symptoms such as nasal flaring, fever, sleeping poorly cough>2 days etc, sensitivity and specificity varied between 20 to 90%[ref 6-10]. High sensitivity was achieved at the cost of specificity and vice-versa.

It is an object of a first aspect of the present invention to provide an improved method for identifying cough sounds.

Furthermore, it is an object of a further aspect of the present invention to provide a method for diagnosis of particular disease states, for example pneumonia, asthma and rhinopharyngitis from cough sounds.

SUMMARY OF THE INVENTION

According to a first aspect of the present invention there is provided a method of operating a computational device to process patient sounds, the method comprising the steps of extracting features from segments of said patient sounds; and classifying the segments as cough or non-cough sounds based upon the extracted features and predetermined criteria.

The patient sounds will preferably comprise sound recordings of the patient.

In a preferred embodiment of the invention the step of extracting features from the patient sound recordings includes processing the segments to determine predetermined statistical parameters.

For example, in a preferred embodiment the predetermined statistical parameters comprise mel-frequency cepstral coefficients "$M_k$" corresponding to the segments.

The predetermined statistical parameters may also include non-Gaussianity scores "$N_k$" indicating the deviation of the segments from a Gaussian model.

The step of extracting features from the patient sound recordings may also include estimating formant frequencies "$F_k$" for said segments.

Preferably the step of extracting features includes determining zero crossing rates "$Z_k$" for the segments to thereby detect a periodicity associated with the recordings.

In a preferred embodiment of the invention the step of extracting features from the segments includes determining wavelet Shannon entropy values "$S_k$", computing kurtosis ($v_k$), pitch ($p_a$), bispectrum scores ($B_k$), log energy ($E_k$).

Preferably the method includes calculating a normalized feature vector $f_k$ based upon said $M_k$, $N_k$, $F_k$, $Z_k$, $S_k$, $v_k$, $p_k$, $B_k$ and $E_k$.

Preferably the step of classifying the segments as cough or non-cough sounds includes determining if they meet the predetermined criteria by comparing the extracted features, or a parameter derived from the extracted features, such as the normalized feature vector, to features of a data set of pre-recorded cough sounds.

The step of classifying the segments may include training an artificial neural network with features of the data set of pre-recorded cough sounds for subsequent classification of test features corresponding to test sound segments to thereby classify the test sound segments into non-cough or cough classes. Alternatively other pattern classifiers may also be used, for example, a logistic regression classification method.

Preferably the method further comprises diagnosing a disease related state based on segments of the patient sound recordings classified as cough sounds.

The method may further include monitoring patient data from a number of sensors.

For example, the method may include monitoring patient data from one or more of: breathing detection sensor, temperature sensor, a movement sensor; EEG sensor; Oxygen level sensor.

The method may include categorizing cough sounds as being "wet cough" or "non-wet cough" sounds.

Where the method comprises diagnosing a disease state it will further include the steps of:
  categorizing cough events of the patient sounds as either diseased or non-diseased;
  computing a diseased cough index indicating the proportion of diseased cough events categorized; and
  deeming the patient to be suffering from the particular disease state in the event of the diseased cough index complying with a predetermined requirement.

The predetermined requirement may be that the diseased cough index exceeds a predetermined threshold.

Preferably the step of categorizing the cough events as either diseased or non-diseased includes processing features extracted from the cough events according to a classification procedure. For example, the classification procedure may comprise application of a logistic regression model. Alternatively, the classifier may comprise application of a trained artificial neural network.

According to another aspect of the present invention there is provided a computational device including at least one electronic processor in communication with an electronic memory containing instructions for the processor to carry out the previously described method for processing sound recordings of a patient to categorize segments of said recordings as cough or non-cough sounds.

For example, the computational device may include a mobile telephone or like device that is programmed to carry out the previously described method.

According to a further aspect of the present invention there is provided a machine readable media bearing tangible instructions for execution by an electronic processor for carrying out the previously described method.

According to a further aspect of the present invention there is provided a method of operating a computational device to process patient sounds of a patient to thereby transform said sounds to indicate a diagnosis of a particular disease state of the patient. For example, the disease state may comprise pneumonia.

Preferably the patient sounds comprise a sound recording of the patient

Preferably the method for diagnosis includes the steps of:
  categorizing cough events of the sound recording as either diseased or non-diseased;
  computing a diseased cough index indicating the proportion of diseased cough events categorized; and
  deeming the patient to be suffering from the particular disease state in the event of the diseased cough index complying with a predetermined requirement.

For example, the predetermined requirement may be that the diseased cough index exceeds a predetermined threshold.

The method may include monitoring patient data from one or more of: a movement sensor; EEG sensor; Oxygen level sensor, breathing detection sensor and temperature sensor.

Preferably the step of categorizing the cough events as either diseased or non-diseased includes processing features extracted from the cough events according to a classification procedure.

For example, the classification procedure may comprise application of a logistic regression model. Alternatively, the classifier may comprise application of a trained artificial neural network, Bayes Classifier, Hidden Markov Model (HMM) based classifier, Support Vector Machine (SVM) etc. In one embodiment a training set for the classifier includes non-pneumonic sounds recorded from patients suffering from complaints such as, Asthma, Bronchitis, Rhinopharyngitis and wheezing, tonsillopharyngitis, congestive heart disease, laryngomalacia and foreign body inhalation.

Various embodiments of the invention encompass long term monitoring (without contact sensors) of inmates in elderly care facilities such as nursing homes. It will be realized that pneumonia is a serious problem among old people and it is best to start treatment as early as possible. Any respiratory condition needing a physician's intervention should be noted by the staff on an urgent basis and the application of methods described herein are of assistance in meeting this requirement. Such a method, according to an embodiment of an aspect of the present invention may be applied to chronically ill patients (with diseases of the immune system or respiratory system) such as AIDS patients, for example.

Embodiments of various aspects of the present invention encompass the triaging of respiratory patients waiting to see a particular specialist in and outside a hospital environment.

According to another aspect of the present invention there is provided a computational device including at least one electronic processor in communication with an electronic memory containing instructions for the processor to carry out the previously described method for processing sound recordings of a patient to categorize segments of said recordings as cough or non-cough sounds.

According to a further aspect of the present invention there is provided a machine readable media bearing tangible instructions for execution by an electronic processor for carrying out the previously described method.

According to another aspect of the present invention there is provided a method of operating a computational device to process patient sounds in a digital electronic format, the method comprising the steps of operating at least one processor of the computational device to extract features from segments of said patient sounds,
  classify the segments as cough or non-cough sounds based upon the extracted features and predetermined criteria, and
  tangibly mark segments as cough or non-cough classified for further processing by the computational device.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
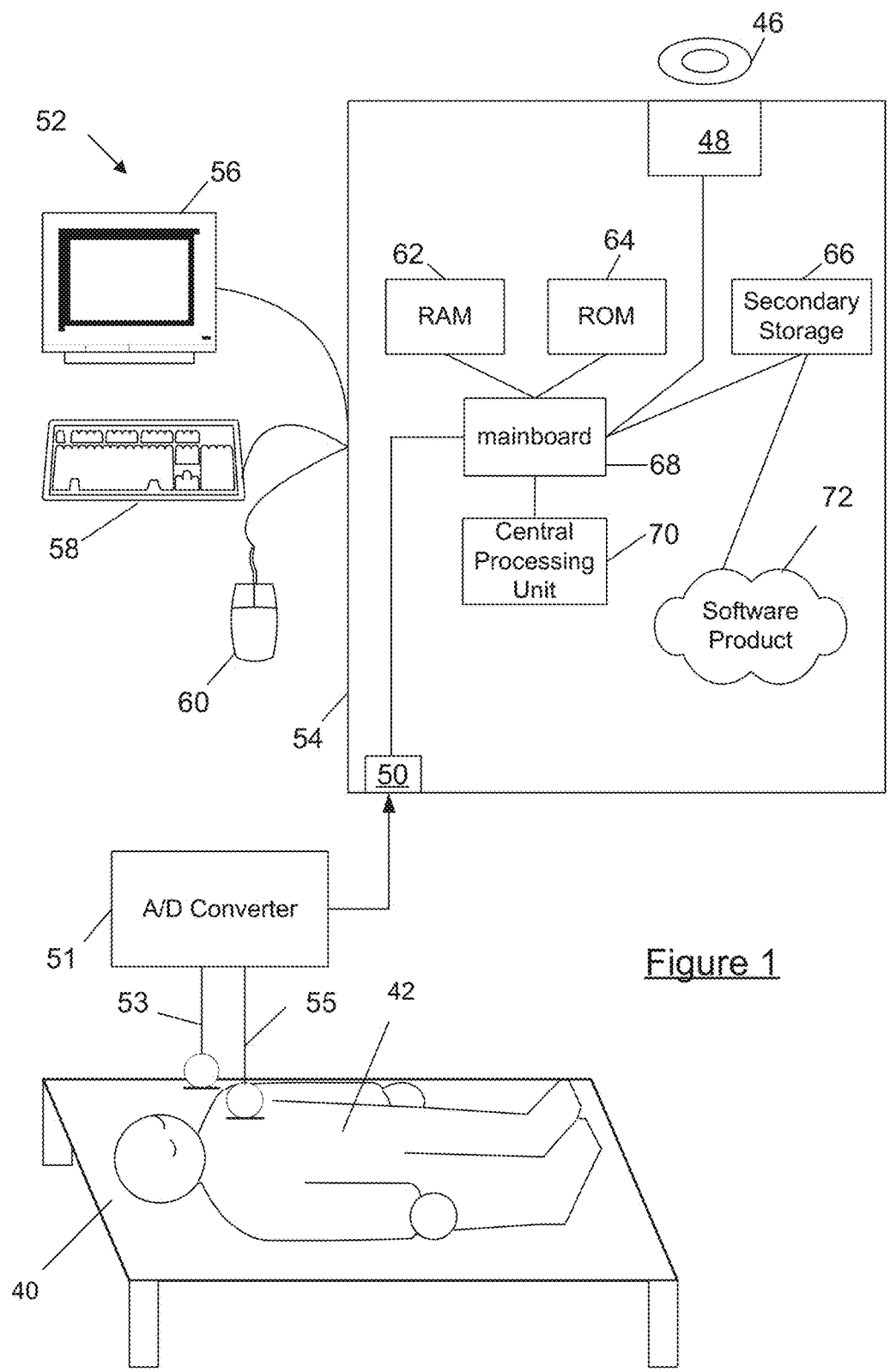
FIG. 1. Is a block diagram of a cough processing system according to an embodiment of the present invention.

I. First Method for Cough Classification 2.1. Cough Recording Protocol

The cough recording system consisted of low-noise microphones 53, 55 having a hypercardiod beam pattern (Model NT3, RODE®, Sydney, Australia), followed by a pre-amplifier 52 and A/D converter 51 (Model Mobile Pre-USB, M-Audio®, CA, USA) for the signal acquisition. The output of the Mobile Pre-USB was connected to the USB port 50 of a laptop computer 52. The nominal distance from the microphones to the mouth of subject 42 was 50 cm. The actual distance could vary from 40 cm to 100 cm due to the subject movement. However, the proposed method did not depend on the sound intensity and the results were independent of the mouth to microphone distance. We kept the sampling rate at 44.1 k samples/s and 16-bit resolution to obtain the best sound quality.

The computer system 52 operates as a cough/non-cough classification system and/or a cough based diagnosis system according to preferred embodiments of various aspects of the present invention, while executing a computer program which will be described shortly. Personal Computer system 52 includes data entry devices in the form of pointing device 60 and keyboard 58 and a data output device in the form of display 56. The data entry and output devices are coupled to a processing box 54 which includes a central processing unit 70. The display 56 comprises a human-machine interface for presenting the results of various classification procedures implemented by the methods described herein. Other human-machine interfaces are also possible, such as a smart phone or a printer for example.

Central processing unit (CPU) 70 interfaces with storage devices that are readable by machine and which tangibly embody programs of instructions that are executable by the CPU. These storage devices include RAM 62, ROM 64 and secondary storage devices i.e. a magnetic hard disk 66 and optical disk reader 48, via mainboard 68. The personal computer system also includes a USB port 50 for communication with the external ADC module 51 which pre-amplifies, filters and digitises signals from microphones 53 and 55. The microphones pick up sounds, e.g. cough sounds, from the subject 42 lying on bed 40.

Secondary storage device 66 is a magnetic data storage medium that bears tangible instructions, for execution by central processor 70. These instructions will typically have been installed from an installation disk such as optical disk 46 although they might also be provided in a memory integrated circuit or via a computer network from a remote server installation. The instructions constitute a software product 72 that is loaded into the electronic memory of RAM 62. When executed the instructions cause computer system 52 to operate as a cough-based diagnosis system, and/or a cough or non-cough patient sound classifier, and in particular to implement a one of a number of methods that will be described shortly.

It will be realised by those skilled in the art that the programming of software product 72 is straightforward in light of the method of the present invention, embodiments of which will now be described. In the following method various variables are manipulated. It will be realized that during operation of computer system 52 to implement the method corresponding registers of CPU 70 will be incremented and data written to and retrieved from secondary storage 66 and RAM 62 by virtue of electrical signals travelling along conductive busses etched on mainboard 68. Consequently, physical effects and transformations occur within computer system 52 as it executes software 72 to implement, the method that will now be described.

Although the computational device that has been shown comprises a personal computer, e.g. a desktop or laptop computer, embodiments of the invention encompass other computational devices. For example, embodiments of the invention encompass a dedicated medical device and also a smartphone loaded with an application, i.e. an "app" for implementing one or more of the methods described herein. In the case of a smartphone the phone's onboard microphone may be used to monitor the patient sounds or alternatively one or more high quality external microphones may be connected to the smartphone for such monitoring. The smartphone may transmit digital recordings of patient sounds to a distant computer which then processes the digital recordings, via cellular telephone networks and/or the Internet, according to the methods that are described herein. The results of the processing may be transmitted back to the smartphone for display thereon or alternatively be displayed on an electronic display device under the control of the distant computer.

The computational device may also be interfaced to a number of patient sensors such as a movement sensor; EEG sensor; Oxygen level sensor, breathing detection sensor, temperature sensor for example. The data from these sensors may also be used during performance of the various methods described herein.

The data for this work was recorded at Sardjito hospital, Yogyakarta, Indonesia, from pediatric patients admitted for respiratory complaints. We acquired data in the natural hospital environment, without modifying it in anyway, other than placing our sound recording system by the bed (see FIG. 1). Recordings were carried out in two types of hospital rooms (single occupancy and double occupancy) during daytime. The research protocol had received ethics clearances from Sardjito Hospital and The University of Queensland, Australia.

Our database consisted of cough sounds from children spanning the age range of 5-64 months. See Table 1 for details of inclusion and exclusion criteria.

TABLE 1

INCLUSION AND EXCLUSION CRITERIA USED IN THE STUDY

| Inclusion criteria | Exclusion criteria |
|---|---|
| Symptoms of respiratory tract infection, at least 2 of: cough, sputum, breathlessness, and temperature >37.5° | Advanced disease where recovery is not expected. Droplet precautions Having non-invasive ventilation treatment |
| Informed consent complete | No informed consent |

The recordings were started after physicians had examined the subjects and the initial treatment had begun. The duration of recording for each subject was from 4-6 hours. In Table 2, we illustrate the demographic details of the subjects.

TABLE 2

THE DEMOGRAPHIC INFORMATION OF THE SUBJECTS INVOLVED IN THIS STUDY.

| Subject | Age (months) | Gender | Diagnosis |
|---|---|---|---|
| 1 | 6 | M | Heart failure, pneumonia |
| 2 | 8 | M | Pneumonia |
| 3 | 2 | M | Rhinopharyngitis |
| 4 | 8 | M | Pneumonia |
| 4 | 5 | M | Pneumonia |
| 6 | 12 | F | Pneumonia |
| 7 | 64 | F | Bronchopneumonia |
| 8 | 16 | F | Pneumonia |
| 9 | 15 | F | Tonsilopharyngitis |
| 10 | 16 | F | Rhinopharyngitis |
| 11 | 9 | M | Pneumonia |
| 12 | 11 | M | Pneumonia |
| 13 | 30 | M | Bronchitis |
| 14 | 11 | M | Pneumonia |

2.2. Cough Segmentation Method

The discretized sound recording, r[n], can be modeled as the summation of cough sounds $s_c[n]$, background noises b[n], and non-cough sounds $s_{nc}[n]$ (e.g., speech, cry, vocalization, appliances movement, etc) as follows:

$$r[n]=s_c[n]+s_{nc}[n]+b[n] \quad (1)$$

Figure 2:
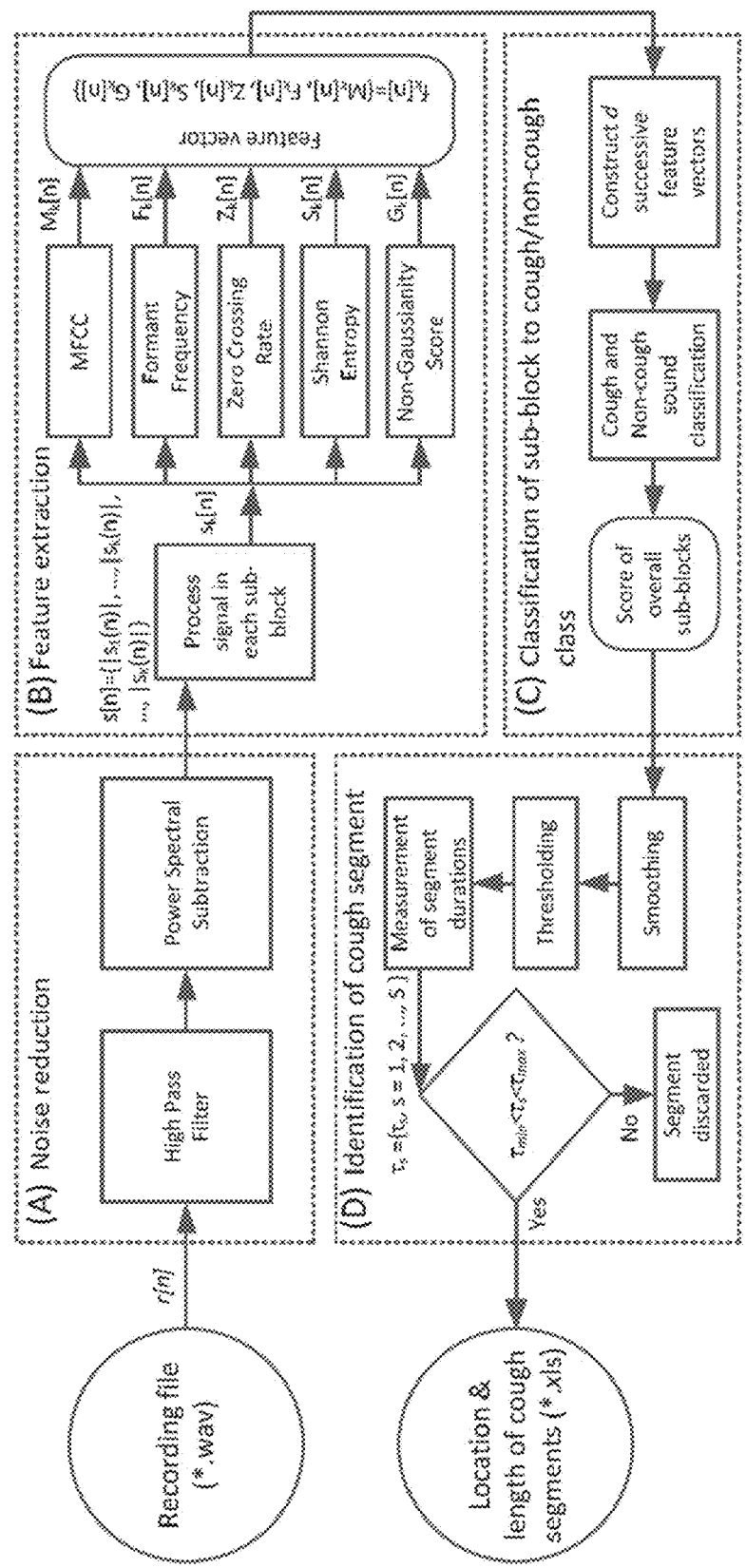
FIG. 2. Is a flowchart of a method according to a preferred embodiment of an aspect of the present invention.

An embodiment of the invention provides an automated method to extract $s_c[n]$ from the recording r[n]. The block diagram of the overall method is shown in FIG. 2. It comprises of four main processes: (a) noise reduction, (b) feature extraction from sub-blocks of data, (c) classification of the sub-blocks of data into cough group (CG) and non-cough group (NG) classes, and (d) identifying/forming cough segments by appropriately grouping CG/NG-classified contiguous sub-blocks of data.

In sections 2.2.1-2.2.4, we provide a detailed description of the method.

2.2.1 Noise Reduction

In order to reduce the background noise b[n], we processed r[n] through two different filters: (a) a high pass filter (HPF), and, (b) a power spectral subtractions (PSS) filter. The HPF was designed as a fourth-order Butterworth filter. It was used to reduce the low frequency interference that may come from the movement of the microphone stands or the bed. The PSS filter was employed to reduce the locally stationary background noise. It estimates the clean sound signal by subtracting the power spectral of original sound signal with estimated background noise [15]. The output signal ŝ[n] after filtering can be re-written as follows:

$$\hat{s}[n] = \hat{s}_c[n] + \hat{s}_{nc}[n] \quad (2)$$

We measured the performance of the filter by computing the signal to ratio [SNR], defined as a measure of signal magnitude relative to background noise, before and after noise reduction process. The SNR is computed as:

$$SNR = 20 \log\left(\frac{R_s}{R_b}\right) \quad (3)$$

where $R_s$ and $R_b$ are respectively the root mean square (rms) value of signal ŝ[n] and the background noise b[n].

After the noise reduction process, ŝ[n] is used as the input to the feature extraction unit.

2.2.2 Feature Extraction of Sound Signal

In this section, we describe the model of cough sound production and the details of the feature extraction unit.

(a) Cough Sound Modeling

Based on physiological considerations, cough sounds are often considered as a combination of four different phases [1]: inspiratory, contractive, compressive, and expulsive. The inspiratory phase is initiated by breathing in and terminated by the closure of the glottis, supraglottis sphincters, or both. In the contractive phase, groups of respiratory muscles contract against glottal structures leading to the compressive phase characterized by marked elevation of alveolar, pleural, and sub glottis airway pressures. In the expulsive phase, the glottis opens quickly followed by rapid exhalation of air under a large pressure gradient. The rapid movement of air expelled from the lung generates the cough sounds with contributions coming from different areas of the respiratory system. The mechanism of cough sounds production shares some similarities to that of speech production.

(b) Feature Design and Extraction

To obtain the features of the sound signal, we apply a rectangular sliding window $w_r[n]$ of length N to ŝ[n], generating data sub-blocks. Let the $k^{th}$ data sub-block be denoted by $s_k[n]$; hence ŝ[n] can be expressed as the concatenation of sub-blocks $s_k[n]$, i.e., ŝ[n]={l||$s_1[n]$|, |$s_2[n]$|, ..., |$s_k[n]$|, ..., $s_k[n]$|} where K is the total number of sub-blocks in ŝ[n]. We compute the following features for each sub-block $s_k[n]$.

i) Mel-frequency cepstral coefficients (MFCCs): MFCC is widely used in speech processing [16, 17], and were found to be highly useful for snore analysis [18-21] as well. In this work, inspired by the similarities of cough/respiratory sounds to snores and speech, we explore the use of MFCC in Cough Segmentation. We compute the first L Mel-frequency cepstral coefficients $M(l)_k = \{M(l)_k, l=1, 2, \ldots, L\}$ of each sub-blocks $s_k[n]$. The coefficient was computed by multiplying the signal $s_k[n]$ with a hamming window $w_h$ followed by applying the successive processes of: Fast Fourier Transform (FFT), Mel-frequency filter bank $f_m$ filtering, and discrete cosine transform. The Mel-frequency filter $f_m$ is defined in (4) and $M(l)_k$ is given in (5).

$$f_m = \left[2595 \log \frac{(1 + f(Hz))}{700}\right] \quad (4)$$

$$M(l)_k = \sqrt{\frac{2}{c}} \sum_{c=1}^{C} (\log D_c) \cos[n(c - 0.5)\pi/c], \quad (5)$$

$$n = 1, 2, \ldots, N$$

where $D_c$ (c=1, 2, ..., C) is the output of the Mel-filter banks.

ii) Formant frequency: In speech, Formant frequencies show characteristics of vocal tract resonances; in snore sound analysis they indicate the resonance of the upper airway. We hypothesized that in cough/respiratory sounds, formant may carry resonances of the entire respiratory tract. For instance, wheezing sounds, which originates due to vibrations of the bronchioles of the lung, may contribute higher frequency formants (resonance frequencies) in the cough sounds. In this work, we estimated the first P formant frequencies $F(p)_k = \{F(p)_k, p=1, 2, \ldots, P\}$. LPC spectrum and its parameters were determined by solving Yule-Walker equations via the Levinson-Durbin recursion [22].

iii) Zero crossing rates (ZCR): The ZCR, defined as the total times a signal crosses the zero axis, is a simple but useful method to detect the periodic nature of a signal regardless of its magnitude. The ZCR feature $Z_k$ is computed as follows.

$$Z_k = \frac{1}{N-1} \sum_{m=1}^{N-1} \prod \{s_k(m)s_k(m-1) < 0\} \quad (6)$$

where the indicator function $\Pi\{A\}$ is 1 if the argument A is true and 0 for otherwise.

iv) Non-Gaussianity score (NGS): The non-Gaussianity score (NGS) provides an easy method to quantify the deviation of a given signal from a Gaussian model. In our previous work on snore sound analysis [23], this feature showed a capability to screen obstructive sleep apnea. To obtain the NGS, in each and every $s_k[n]$, we computed the inverse ($F^{-1}$) of normal Cumulative Distribution Function ($\gamma$) as given in (7).

$$\gamma = F^{-1}(p|\mu,\sigma) = \{\gamma : F(\gamma|\mu,\sigma) = p\} \quad (7)$$

where $\mu$, $\sigma$, respectively are the mean and standard deviation of $s_k[n]$, and p is defined in (8).

$$p = F(\gamma|\mu, \sigma) = \frac{1}{\sigma\sqrt{2\pi}} \int_{-\infty}^{\gamma} e^{\frac{-(t-\mu)^2}{2\sigma^2}} dt \quad (8)$$

The NGS ($N_k$), is the deviation of the probability plot of $s_k[n]$ ($\gamma$) to its reference Gaussian probability plot (g) given in (9), where g[n] and $\gamma$[n], respectively represent the probabilities of the reference normal data and the analyzed data.

$$N_k = 1 - \left(\frac{\sum_{n=1}^{M} g[n] - \bar{g}}{\sum_{n=1}^{M} \gamma[n] - \bar{\gamma}}\right) \quad (9)$$

v) Shannon entropy: Cough sound is a complex signal which represents contributions from various sub-structures of the respiratory tract. Some of these components display pseudo-periodic structures, while others have a random stochastic character. In some cases, cough sounds have abrupt transitions from inspiratory phase to expiratory phase. This period may contain instant break as well as high frequency components. In this work, we computed the Shannon wavelet entropy to capture these features. In wavelet analysis, the signal $s_k[n]$ at scale i can be decomposed into its high and low frequency component using a complementary filter consisted of low pass and high pass filter. The outputs from low and high filter are defined as approximation and details ($A_i$ and $D_i$, respectively). The wavelet Shannon entropy $S_k$ is obtained using definition in (9) by computing the wavelet energy spectrum $E_i$ as in (10) [24].

$$S_k = -\Sum_{i=1}^{1} E_i \log E_i \quad (9)$$

$$E_i = |D_i[n]^2| \quad (10)$$

The features described in B(i)-(v) are computed for each sub-blocks $s_k[n]$. In each feature, we computed the minimum and the maximum values in each feature of $M_k$, $F_k$, $Z_k$, $S_k$, and $N_k$. We used these values to normalize the components of the corresponding feature into range of −1 to 1.

The normalized parameter vector $f_k$ of $s_k[n]$ is then defined as: $f_k = \{[M_k \ F_k \ Z_k \ S_k \ N_k]^T\}$. The overall feature matrix $G_j$ for the $j^{th}$ patients is then given by $G_j = \{f_{1,1}, f_{1,2}, \ldots, f_{k,j}, \ldots, f_{K,J}\}$.

As illustrated in FIG. 2, the Cough Segmentation technique according to an embodiment of the invention starts by classifying each and every data sub-blocks $s_k[n]$ into the two non-overlapping categories of Cough. Group (CG) and non-Cough Group (NG) based on the feature vector $f_{k,j}$.

In section 2.2.3, we describe the pattern classification scheme we developed for this CG/NG classification at the sub-block level.

2.2.3 Classification of Sub-Blocks into Cough and Non-Cough Classes

One embodiment of the invention makes use of an Artificial Neural Network (ANN) as the CG/NG pattern classifier at the sub-block level. We used the ANN inspired by the capability of human brain to recognize different types of cough sounds regardless of their intensity, duration, or wetness. Moreover, ANN has several advantages in that its capable of classifying data using non-linear decision boundaries, based on a process of supervised learning with a set of given examples. It has a proven ability to work with limited training data sets compared to conventional methods [25]. In this work, we used the particular form of an ANN known as a Time Delay Neural Network (TDNN) [26] that has found success in speech recognition applications. TDNN is capable of classifying data sub-blocks $s_k[n]$ discounting temporal translations [26] of the input feature set.

Figure 3:
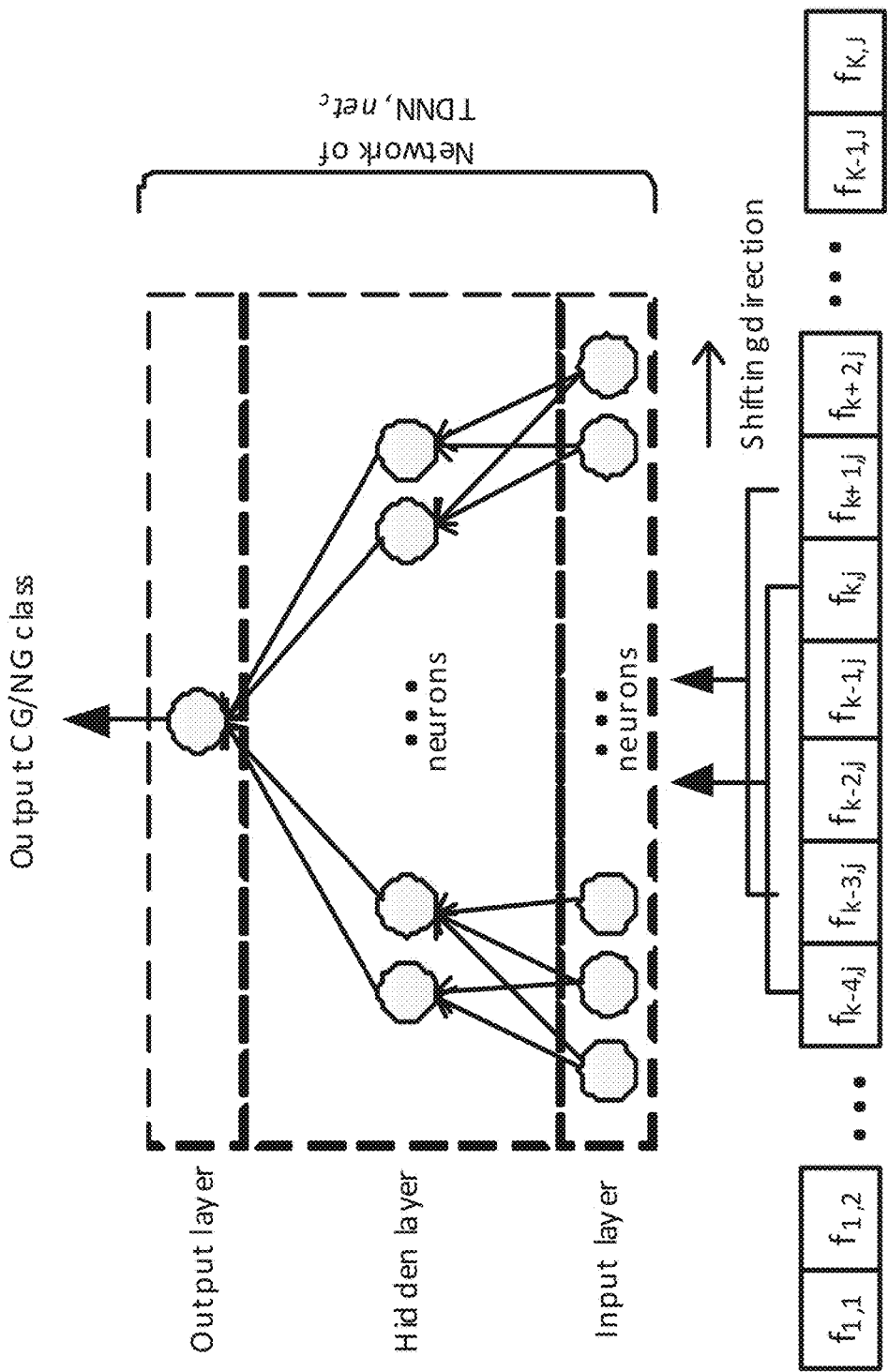
FIG. 3. The structure of TDNN. It comprised of an input layer, a hidden layer, and an output layer. The input of TDNN is d successive feature vector $f_k$. As an example, for d=5, the input is $\{f_{k-4,j}, f_{k-3,j}, \ldots, f_{k,j}\}$. To classify the all sub-blocks, the input is shifted by a sub-block to the right.

We show the structure of TDDN in FIG. 3. It comprised of an input layer, a hidden layer, and an output layer. In TDNN, we used d successive feature vectors of the matrix $G_j$, to classify a sub-block as a CG/NG class. To classify the next sub-block, we shifted the input by a sub-block the right, and used the next group of feature vectors. We performed this process from the beginning to the end of matrix thus all of the sub-blocks in ŝ[n], can be classified into CG/NG class.

The classification of sub-blocks using TDNN was carried out through the process of training, validation, and testing. To complete these processes, we prepared a data set, selected the training parameters, trained the TDNN, and validated the classification results. Details of these processes are described in the following sub-sections.

(a) TDNN Data Set Preparation.

We developed a data set comprised of cough and other sounds from the recording. There are 665 cough sounds in our data set. We divided our data set into three non-overlapping random partitions, and named them as training (TDS), validation (VDS) and testing (TeDS), respectively. The proportions of TDS, VDS, and TeDS from the database are (40%, 30%, and 30%, respectively). We denote the $m^{th}$ such random partitions by the symbol $C_m$, m=1, 2, . . . , M, where M is the total number of random partitions used in this work. All classification data set were analyzed independently. We effectively used our data set by applying K-fold cross validation method using the random sub-sampling technique.

By using information cough segments locations of the classification data set, we defined a matrix $W_k = [w_1, w_2, \ldots, w_k, \ldots, w_K, w_k = \Pi\{CG \ class\}]$, where $w_k$ is the class of each sub-block of $s_k[n]$ filled by "1" when the argument of $\Pi\{CG \ class\}$ is correct and "0" for otherwise. The matrix $W_k$ was used as a target in the training process. Note that the dimension of $W_k$ is similar to $G_j$.

(b) TDNN Training Process

TDNN used in this study has the parameters as prescribed in Table 3.

TABLE 3

TDNN TRAINING PARAMETERS

| Parameters | Details |
| --- | --- |
| Number of layers | 3 |
| Number of neurons per layer | Input layer ($L_i$) = 110, Hidden layer ($L_h$) = 20, Output layer ($L_o$) = 1 |
| Activation function | Tangent sigmoid and linear |
| Weight and initialization | Nguyen-Widrow |
| Training method | Resilient back propagation (RPROP) |
| Stopping criteria | Mean square error = $10^{-5}$, Minimum gradient = $10^{-10}$, Maximum validation failure = 100 |
| Successive inputs (d) | 5 |

We explain the procedure used to determine the selection of number of the neuron in Section 3.4.

We constructed the network of TDNN, denoted as $net_c$, comprising of an input layer $L_i$, a hidden layer $L_h$, and an output layer $L_o$. The linear and sigmoid functions were selected as activation function between layers. To determine the initial weight and bias, we used the Nguyen-Widrow initialization method.

For updating the bias term and weights of neuron during the training process, we employed the resilient back propagation (RPROP) algorithm [27]. The RPROP was found success to overcome problem of determining learning rate for updating the weights of neurons. In gradient descent algorithm, a too small learning rate increase the computation time while a too large learning rate will produce oscillation before reach the optimum point with reasonable error. In contrast, the RPROP use an adaptive value to update the weight, hence it is capable of achieving the maximum optimization quickly. The details of this algorithm is described in [27].

In the training process, we defined stopping criteria: (a) the mean squared error (mse) of the training data was less than $10^{-5}$, (b) the validation error began increasing, and (c) a minimum gradient in training performance of $10^{-10}$ was reached. Unless the training was stopped earlier, the neural network was allowed to train up to 100 epochs.

Once these parameters have been set, we started training the TDNN. In the training process, we let the network of TDNN $net_c$, to learn classifying the sub-blocks into CG/NG class. The process was carried by giving d successive feature vectors from $G_j$ to $net_c$, to approximate a target in, $W_k$. We investigated several combinations of features in $f_k$ to find the combination of inputs which give the best results in classifying the CG and NG classes. We denoted the output of the $net_c$ during training process as $\hat{W}_k$, the approximation of $W_k$. To identify the Cough Segments, $\hat{W}_k$ was processed as in the following section.

2.2.4 Identification of Cough Segment

In this section, we describe the technique to obtain the Cough Segment by processing the output of TDNN ($\hat{W}_k$) through segment identification process. The process comprised of: smoothing the output of TDNN, applying a threshold to the smoothed signal to obtain segments, measurement of the duration of segments, and selection of the segments based on a criterion. The overall processes are described in the following steps:

(S1) Define a parameter β, a small positive integer which determines the span of moving average filter (H). Apply $\hat{W}_k$ to filter H to produce a smoothed signal $\hat{w}_k$.

(S2) Apply threshold value (2) to the smoothed signal $\hat{w}_k$. The output signal from this process was denoted as $\ddot{w}_k$ given in (11). The group of contiguous elements in $\ddot{w}_k$ was defined as cough segment candidates.

$$\ddot{w}_k \begin{cases} 1, & \text{for } \hat{w}_k \geq \lambda \\ 0, & \text{for } \hat{w}_k < \lambda \end{cases} \quad (11)$$

(S3) Compute the duration ($\tau_s$) of the corresponding segments containing '1' in $\overline{w}_k$. This process is carried by determining the start and end of each segment.
  a. Starting k=1, find the smallest value of k (say $k_a$) where all sub-blocks $\ddot{w}_k$ correspond to the category of NG class. The beginning of the sub-block $\ddot{w}_k$, k=$k_a$ was taken as the beginning of a NG segment.
  b. To identify the beginning of cough segment, start the searching in the domain of $k_a$<k<K. Find the smallest value of k (say $k_b$) in that domain, such that none of the sub-blocks in $\ddot{w}_k$ correspond to NG. The beginning of the sub-block $\ddot{w}_k$, k=$k_b$ is taken as the beginning of a CG segment.
  c. The end of NG is determined in a process similar to step (S3.a), with search domain for k set to $k_b$<k<K.

(S4) Define parameters of $\tau_{min}$ and $\tau_{max}$, a small positive fraction which determine the minimum and maximum segment duration of a typical cough sound from children. The segments which durations are outside of this constraint will be discarded. We denoted the output signal of this process as $\dot{w}_k$.

Steps (S1)-(S4) describe the method to determine the beginning and the end of each segment of $s_c[n]$ and to discount segments of $s_{nc}[n]$ in a recording. In order to validate the results, all obtained cough segments in $\dot{w}_k$ were compared with cough segments in $W_k$.

II. Results and Discussion

3.1 Cough Segment Duration

Figure 4:
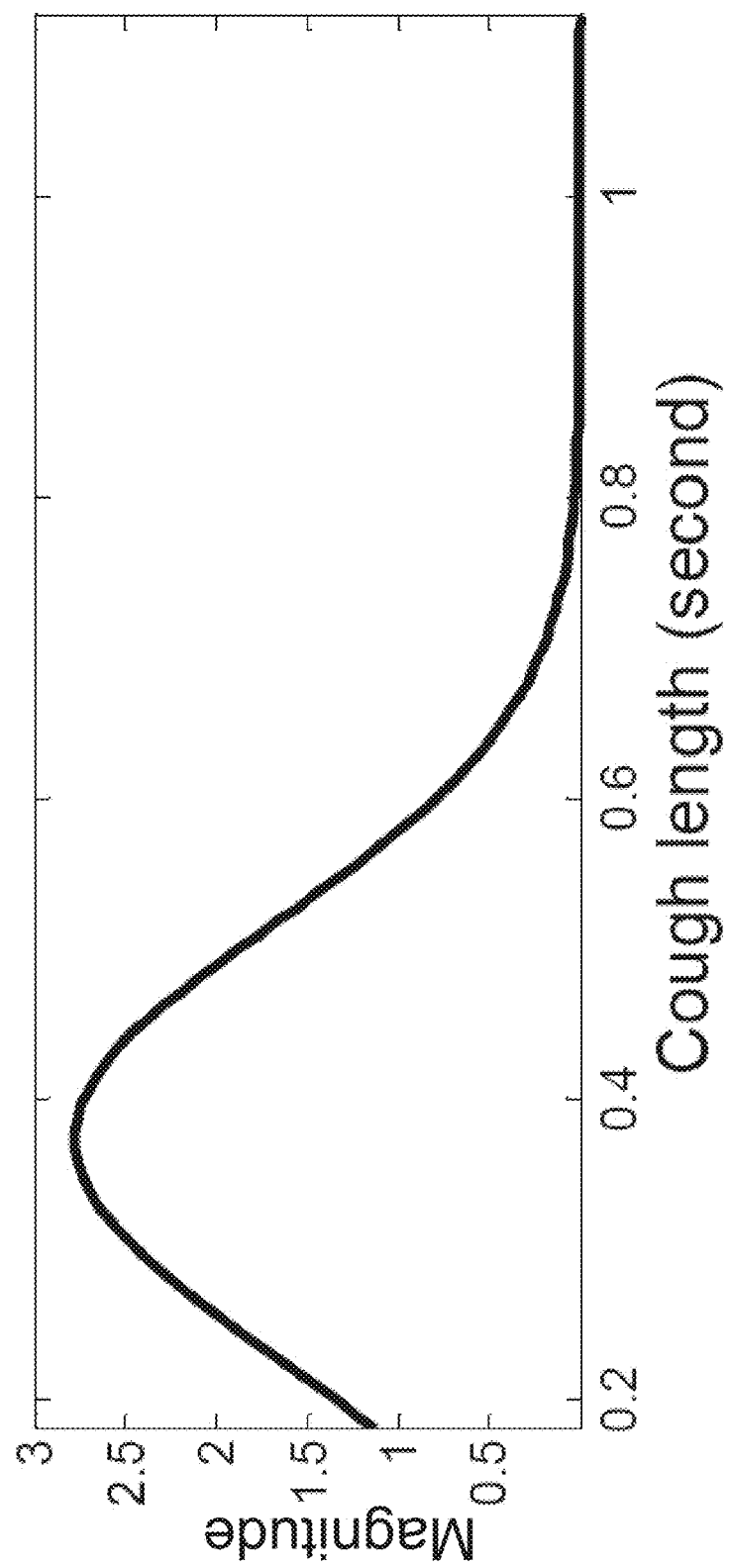
FIG. 4. The smoothed probability density function of the duration of cough segments ($\tau_s$). It has mean of 0.373 s, and standard deviation of 0.144 s.

In our clinical data, we identified the duration of each cough segment ($\tau_s$) by a combined process of visual observation and listening. The smoothed probability density function of $\tau_s$ is illustrated in FIG. 4. The cough segments have minimum and maximum duration of ($\tau_{min}$=0.18 s and $\tau_{max}$=11.6 s). The mean and standard deviation of the cough segments are ($\mu_s$=0.373, $\sigma_s$=0.144). In the segmentation process, we use the $\tau_{min}$ and $\tau_{max}$ as one of the criteria to determine the predicted segments as cough or non-cough sound. We describe this process in Section 3.5.

3.2 Noise Reduction

Recording in an uncontrolled environment makes the data more susceptible to background noise. In our recordings, we identified two separate components of noise: (a) low-frequency noise below 10 Hz and (b) white Gaussian noise (see FIG. 5(A)). From the figure it could be seen that the recording has a poor signal to noise ratio (SNR) spanning the range 1.54-5.92 dB. To reduce theses noises we used a fourth order Butterworth high pass filter (HPF) with 10 Hz cut off frequency and power spectral subtraction (PSS) filter.

These filters improved the SNR significantly. The HPF increased it to 11.98-17.19 dB (FIG. 5(B)) and the PSS further increases it to 12.62-17.44 dB (FIG. 5(C)). These results show that the developed filters capable of reducing the background noise and improving the SNR of the recording signal.

3.3 Characteristic of the Sound Feature

As described in Section 2.2.2, we computed the feature vector $f_k$={$M_k$ $F_k$ $Z_k$ $S_k$ $N_k$} for each sub-block of $s_k$[n]. We used the sub-block size N=882 (20 ms). The selected sub-block size is the basic unit for feature extraction of MFCC. Smaller sizes (e.g., 10 ms), generally lead to distorted results, because of very few samples involved in Mel-filter integration; larger sizes have tendency to increase the word error rate [28].

The feature vector $f_k$ contains 22 elements: 14 coefficients of $M_k$ (including log energy and the $0^{th}$-$12^{th}$ cepstral coefficients), 5 coefficients of $F_k$, and 1 coefficient of each $Z_k$, $S_k$, and $N_k$. To discover the characteristic of these features, we calculated the probability density function (pdf) of a specific sound in the CG and NG classes. The NG represent wide range of non-cough sounds, hence in this work; we choose the most dominant sound such as cry (CY), vocalization (abbreviated as VC, e.g., speech, typical baby voices) and appliances sound (abbreviated as AS, e.g., sound from the door bank, trolley, bed).

Figure 6:
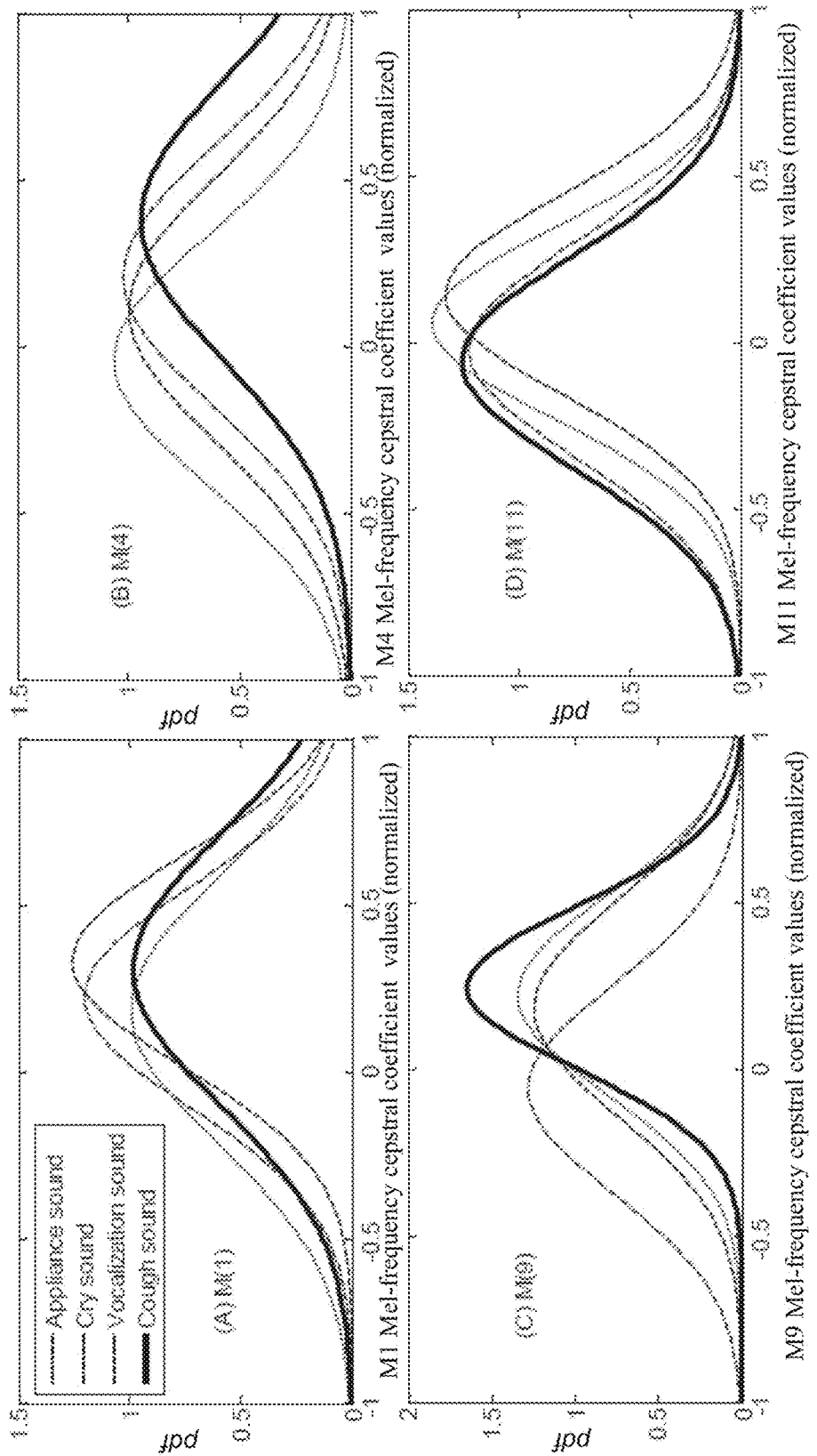
FIG. 6. The probability density function (pdf) of randomly selected Mel-frequency cepstral coefficient (smoothed for display purposes). Although there are overlapping, the coefficient M(4) can be used to differentiate cough and appliance sound, the coefficient M(9) differentiate between cough to cry, and M(11) differentiate between cough and vocalization.
Figure 7:
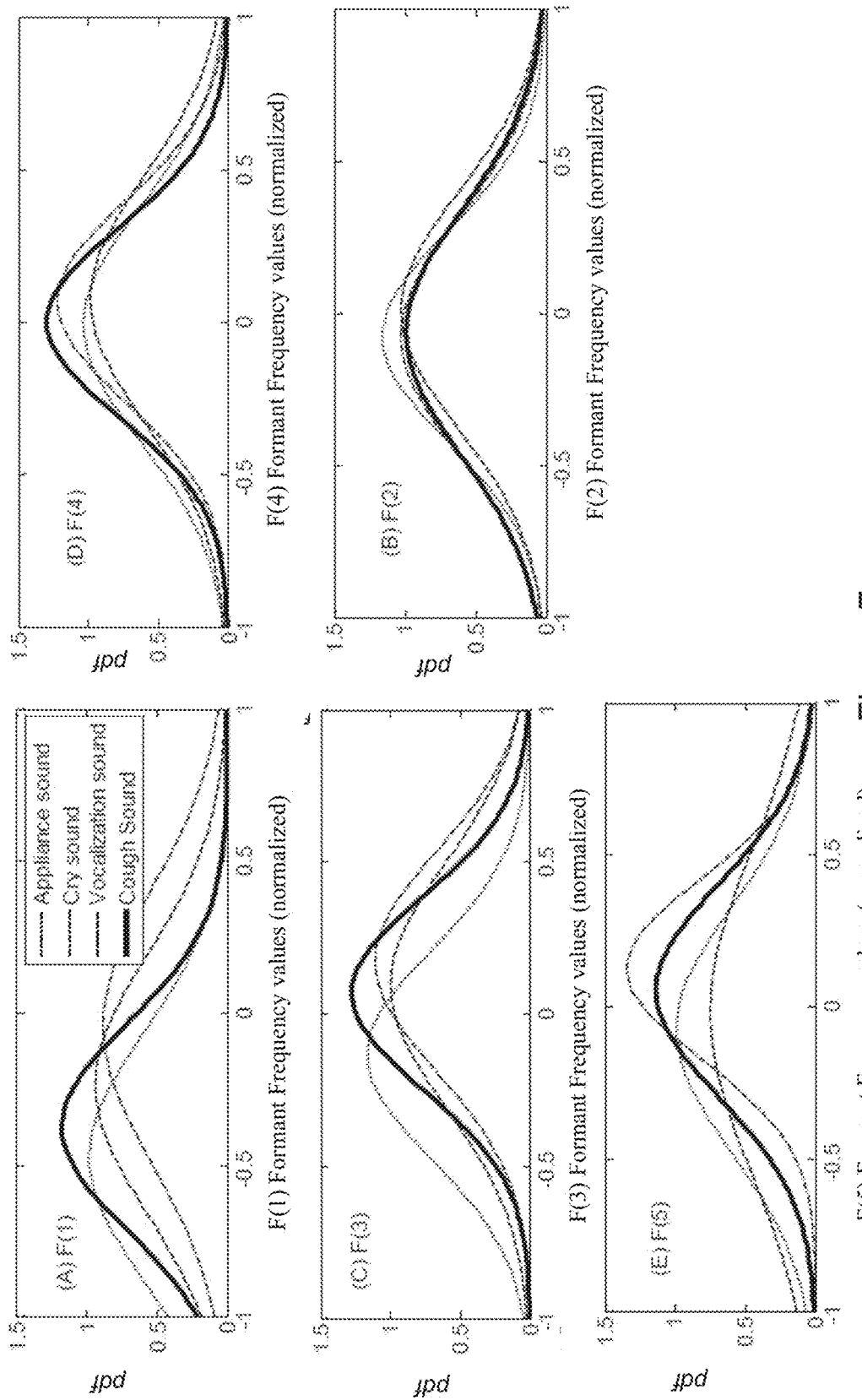
FIG. 7. The pdf of five first formant frequencies (F(1)-F(5)). Even though the distribution of the formant frequencies are overlapping, they have different mean, skewness, and kurtosis, especially for F(1), F(3), and F(5).
Figure 8:
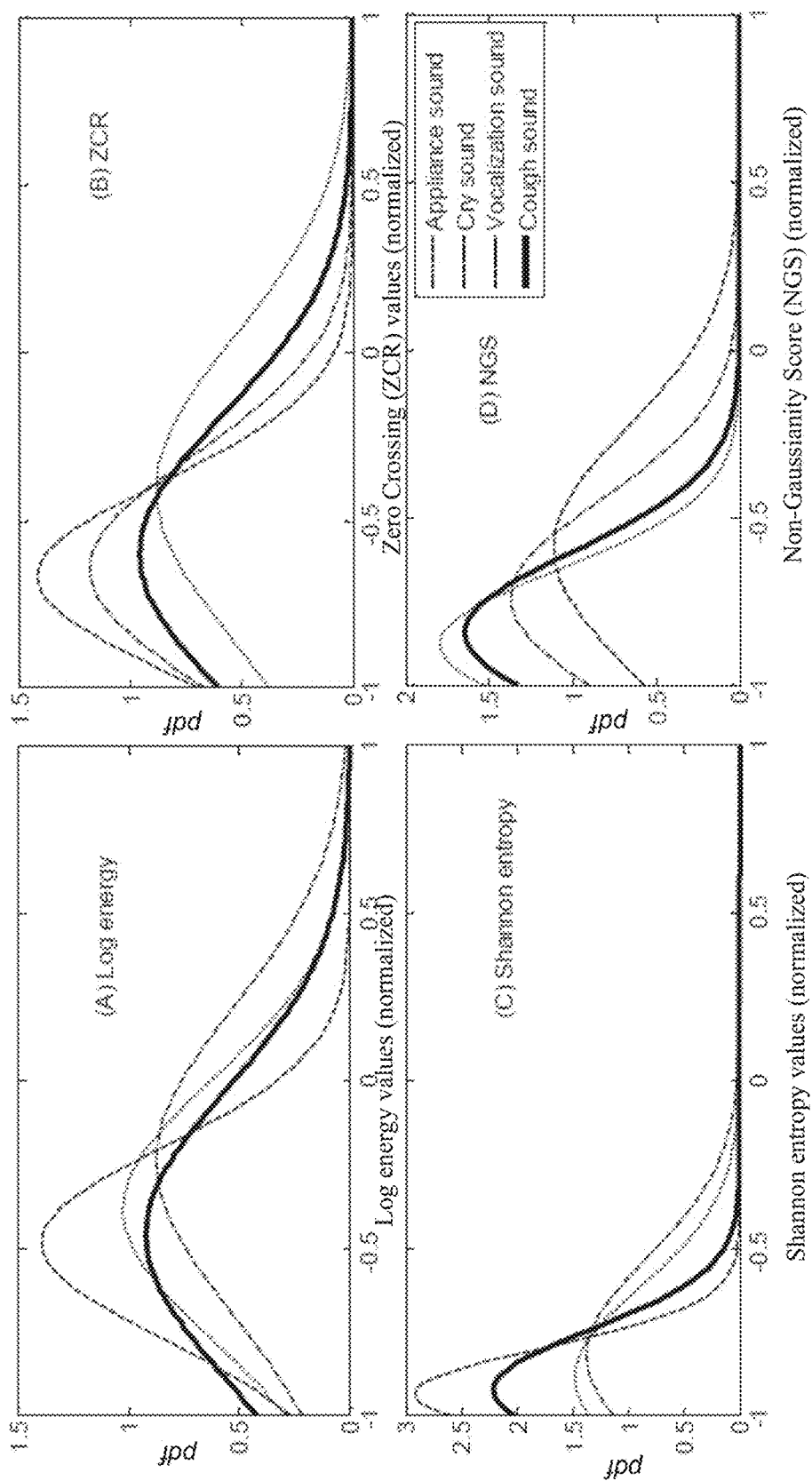
FIG. 8. The pdf of the energy, zero crossing rate (ZCR), Shannon entropy, and non-Gaussianity score (NGS). The NGS can be used to differentiate between cough with vocalization and cry, while ZCR differentiate between cough and appliance sound. The profile of log energy and Shannon entropy between sounds are similar but they have different skewness and kurtosis.

We illustrate the smoothed pdf of each feature of $f_k$ in FIG. 6-8. As can be seen from these figures, the distribution of features ($M_k$, $F_k$, $Z_k$, $S_k$, and $N_k$) between cough and other sounds are overlapping. However, each component of the features has a unique distribution.

Figure 5:
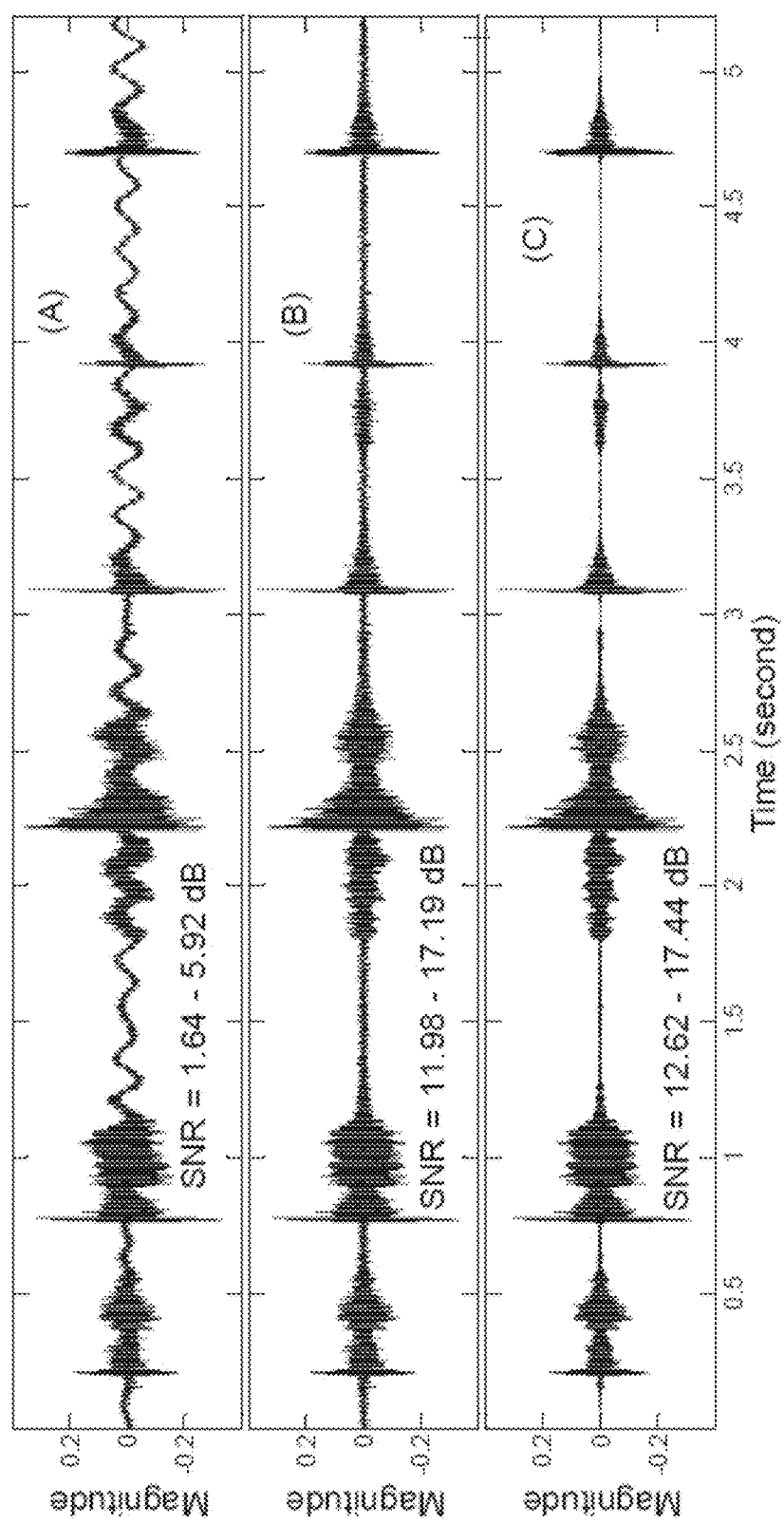
FIG. 5. Illustrates a noise reduction process. (A) is typical signal in the recording, (B) is the output of high pass filter, and (C) is the output spectral subtraction filter. The developed filter improved the SNR (signal to ratio) of the signal significantly.

FIG. 6 shows the pdf from a randomly selected elements of MFCC (M(1), M(4), M(9), and M(11)). From FIGS. 5(A) and 5(B), it could be seen that the pdf of M(1) in CG and AS classes have different mean ($\mu$=0.31 to 0.18). The pdf of M(9) in FIG. 5(C) show that CG has lower mean than CY ($\mu$=−0.01 to $\mu$=−0.13, respectively).

FIG. 7 exhibits the pdf of formant frequencies. The statistical distribution (mean, standard deviation, skewness, and kurtosis) of formant frequencies of F(1), F(3), and F(5) between CG and AS are distinguishable. The distribution of F(2) in CG, CY, VC, and AS seem similar, however CG has the lowest mean (−0.06). Moreover, the distribution of F(4) in TS has the lowest mean among the classes (−0.003).

In FIG. 8 we illustrate the NGS index of CG, CY, VC, and AS. The NGS has the potential to discriminate CG from VC and CY (FIG. 7(D)). Similarly, from FIG. 6(B) it could be seen that ZCR can be used to discriminate CG from AS.

The pdf of the features shows that there are no dominant feature which can be used alone as an input for TDNN to classify CG/NG class. Hence, to obtain the maximum benefit of each component of the features, we combined them and used d successive of features vector as the input of TDNN to classify CG/NG class.

3.4 TDNN-Based Analysis in CG/NG Classification

In this work, we used five successive feature vectors (d=5); hence the number of neurons in the input layer is ($L_i$=110). In the output layer, there is only one neuron ($L_o$=1) to represent of CG or NG class. To determine the number of neurons in $L_h$, we tested several numbers of neurons during the training process.

To evaluate the performance of the network ($net_c$), we computed the sensitivity and the specificity defined by the following equations.

$$\text{sensitivity} = TP/(TP+FN) \times 100 \quad (12)$$

$$\text{specificity} = TN/(FP+TN) \times 100 \quad (13)$$

where TP=True Positive, TN=True Negative, FP=False Positive, and FN=False Negative.

In Table 4, we show the performance of net for different values of $L_h$.

TABLE 4

THE PERFORMANCE OF TDNN FOR DIFFERENT COMBINATIONS OF HIDDEN LAYERS ($L_H$). THE HIDDEN LAYER WITH 20 NEURONS SHOWS THE BEST CLASSIFICATION PERFORMANCE.

| Number of neurons in hidden layer ($L_h$) | Data set | Performance Sensitivity | Specificity |
|---|---|---|---|
| 10 | TDS | 98.34 | 98.35 |
|  | VDS | 85.24 | 85.24 |
|  | TeDS | 90.32 | 90.35 |
| 20 | TDS | 98.12 | 98.13 |
|  | VDS | 86.80 | 86.61 |
|  | TeDS | 91.51 | 91.51 |
| 30 | TDS | 98.31 | 98.32 |
|  | VDS | 85.03 | 85.05 |
|  | TeDS | 90.24 | 90.25 |
| 40 | TDS | 98.41 | 98.41 |
|  | VDS | 85.57 | 85.57 |
|  | TeDS | 91.45 | 91.45 |
| 50 | TDS | 98.43 | 98.43 |
|  | VDS | 85.69 | 85.69 |
|  | TeDS | 89.89 | 89.92 |

From Table 4 it could be seen that in the testing set (TeDS), the $net_c$ with 20 neurons in the hidden layer has the highest sensitivity and specificity of (both 91.51%). Thus, for the rest of this discussion we fix the network $net_c$ ($L_i$=110, $L_h$=20, $L_o$=1). The number of neurons in net is compact enough to be used in a system with limited computing resources. The small number of layer and neurons also improve the capability of the network to develop the best model for CG/NG classification and to avoid memorizing the samples given in the training.

We show the performance of the classification of sub-block $s_k[n]$ into cough (CG) and non-cough (NG) classes, using different combination of features in Table 5.

TABLE 5

THE PERFORMANCE OF TDNN IN DIFFERENT COMBINATION OF FEATURES. THE COMPLETE COMBINATION $\{M_K F_K Z_K S_K N_K\}$ HAS THE BEST SENSITIVITY AND SPECIFICITY.

| Data set | $M_k + F_k$ | | $Z_k + S_k + N_k$ | | $M_k + Z_k + S_k + F_k + N_k$ | |
|---|---|---|---|---|---|---|
| | Sens. | Spec. | Sens. | Spec. | Sens. | Spec. |
| TDS | 99.05 | 99.05 | 87.00 | 87.00 | 98.12 | 98.13 |
| VDS | 85.69 | 85.73 | 81.44 | 81.48 | 86.80 | 86.81 |
| TeDS | 89.37 | 89.37 | 79.95 | 79.98 | 91.51 | 91.51 |

In the testing set (TeDS), the classification result using $\{Z_k S_{hk} N_k\}$ shows the lowest sensitivity and specificity (79.95 and 99.98) respectively. The combination $\{M_k F_k\}$ has a higher result with 89.37% of sensitivity and specificity. In contrast, the combination of $\{M_k F_k Z_k S_{hk} N_k\}$ achieved the best sensitivity and specificity of 91.51%. Next, we explored the combination $\{M_k F_k Z_k S_{hk} N_k\}$ as the input for TDNN.

The performance of TDNN for M=14, ($C_m$, m=1, 2, . . . , 14) is shown in Table 6.

TABLE 6

SUMMARY OF NG/CG CLASSIFICATION OUTCOMES FROM TDNN FOR M = 14, (CM, M = 1, 2, . . . , 14).

| Data set | Sensitivity | | Specificity | |
|---|---|---|---|---|
| | mean | std | mean | std |
| TDS | 96.77 | 0.0121 | 96.78 | 0.0121 |
| VDS | 89.40 | 0.0170 | 89.41 | 0.0170 |
| TeDS | 91.13 | 0.0073 | 91.14 | 0.0073 |

Classification outcomes for each realization, $C_m$, m=1, 2, . . . , 14, were computed and the mean and the standard deviation of sensitivity and specificity were estimated (91.13±0.0073% and 91.14±0.0073%, respectively).

2.3. Formation of Cough Segments from Sub-Blocks

Figure 9:
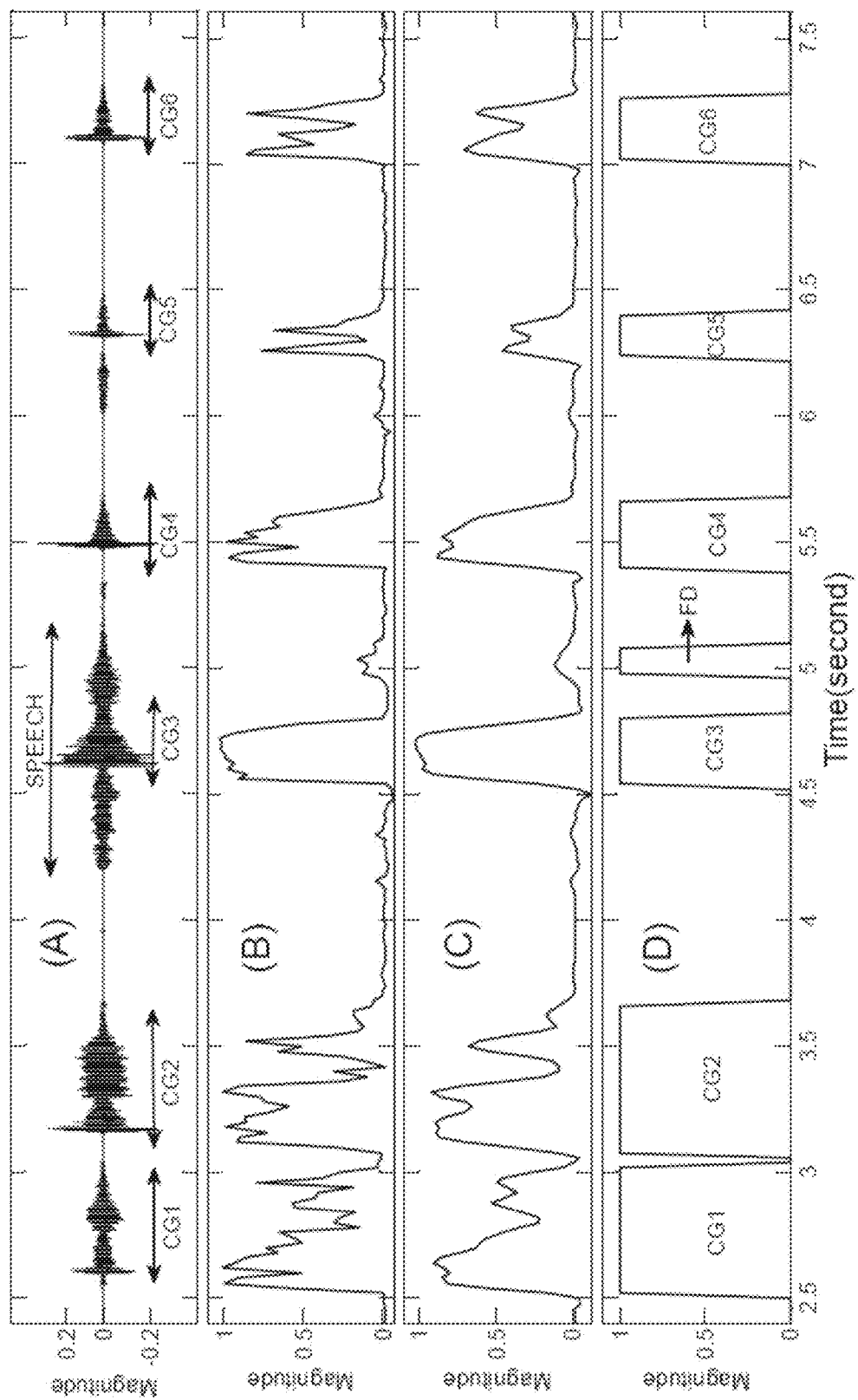
FIG. 9. Illustrates cough segment identification. (A) The sound signal from the noise reduction process, (B) the output signal from TDNN, (C) the output signal after smoothing process, and (D) the output signal after thresholding process. The signal from the thresholding may contain false segment (e.g., FD segment).

We illustrate the formation of cough segments, starting from sub-blocks classified in Section 3.4, in FIG. 9. FIG. 9(A) shows the signal from the noise reduction process while FIG. 9(B) illustrates the output signal from TDNN-based classification ($\hat{w}_k$). In FIG. 9(B) we show the output of the network $net_c$ representing the approximation of the state of CG and NG classes (1 and 0, respectively). As can be seen, the groups of sub-blocks associated to cough sounds formed segments with value close to 1, and otherwise for the groups of sub-blocks from the non-cough sounds. From the FIG. 9(B) it also could be seen that the network $net_c$ effectively classify the sub-blocks into CG and NG classes, even though they overlap with speeches (illustrated in CG3 signal). However, some of the sub-blocks in the middle parts of CG2 and CG5 segments were misclassified as NG class indicated by the sharp transition from high to low values.

To refine the segments and reduce the misclassified sub-blocks in the segments, we processed the signal into a smoothing process based on moving average filter. In this stage, we carefully selected the span of the moving average filter as (β=9). We show the smoothed signal ($\ddot{w}_k$) obtained from smoothing process in FIG. 9(C). As can be seen from FIG. 9(C), the sharp transition parts in the corresponding segments were reduced.

Figure 10:
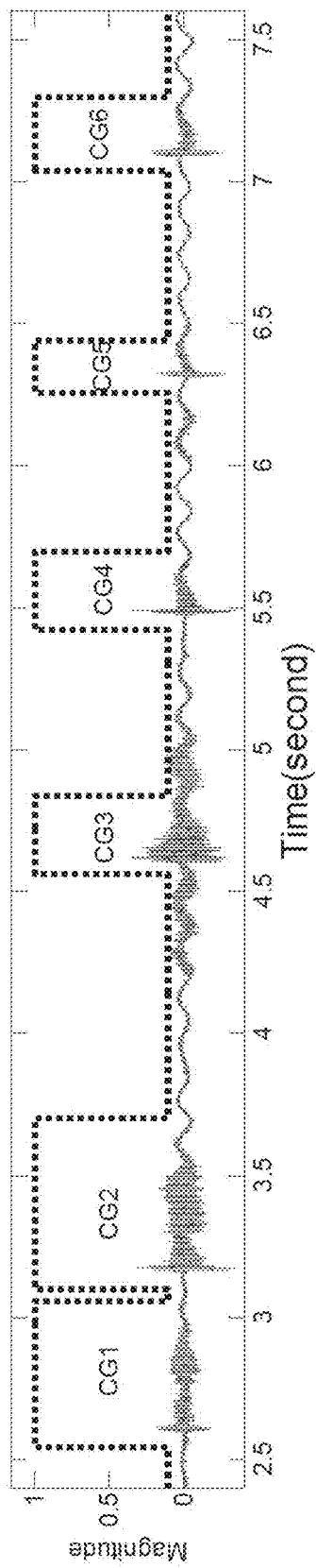
FIG. 10. The illustration of input signal and the output signal from segmentation algorithm. The dashed line indicates the segmentation output where the beginning and the end of each cough segment can be determined. The false segment FD (shown in FIG. 9(D)) is discarded because its duration is outside the criteria of duration ($\tau_{min} < \tau_s < \tau_{max}$). The algorithm successfully segments all cough sounds including CG3 which overlaps with speech (SP).

To determine the beginning and the end of cough segments, all elements in $\ddot{w}_k$ were compared against a threshold ($\lambda$). The corresponding element will be set to 1 If $\ddot{w}_k > \lambda$ then and 0 for otherwise ($\ddot{w}_k < \lambda$), where A was set to 0.05. This value of $\lambda$ was chosen to maximize the classifier performance. We show the output signal from thresholding process ($\ddot{w}_k$) in FIG. 9(D). It now contains two groups of segments formed from 1 and 0 elements. We denoted the segments with elements of 1 as cough segment candidates Next, we defined the first element in a cough segment candidate as the beginning of the segment and the last element as the end of the segment. From Section 3.3 and 3.4 we knew that each element in a segment represents the class of 20 ms sub-block. Hence, we can compute the duration of a segment by multiplying the number of elements between the beginning and the end of a segment with 20 ms. We computed the duration of each segment ($\tau_s$), and tested $\tau_s$ against a minimum and maximum cough duration obtained in Section 3.1. Only the cough segment candidates which durations within the boundary ($\rho_{min} < \tau_{max}$) were selected as cough segments. The illustration of this process is shown in FIG. 10. From the figure it could be seen that the proposed method effectively segments the cough (CG1-CG6) even though they have different intensity and duration. Moreover, although cough sound CG3 is overlapped with speech, the method is capable of extracting the corresponding cough sound. The false segment (FD) shown in FIG. 9(D) also has been eliminated.

Figure 11:
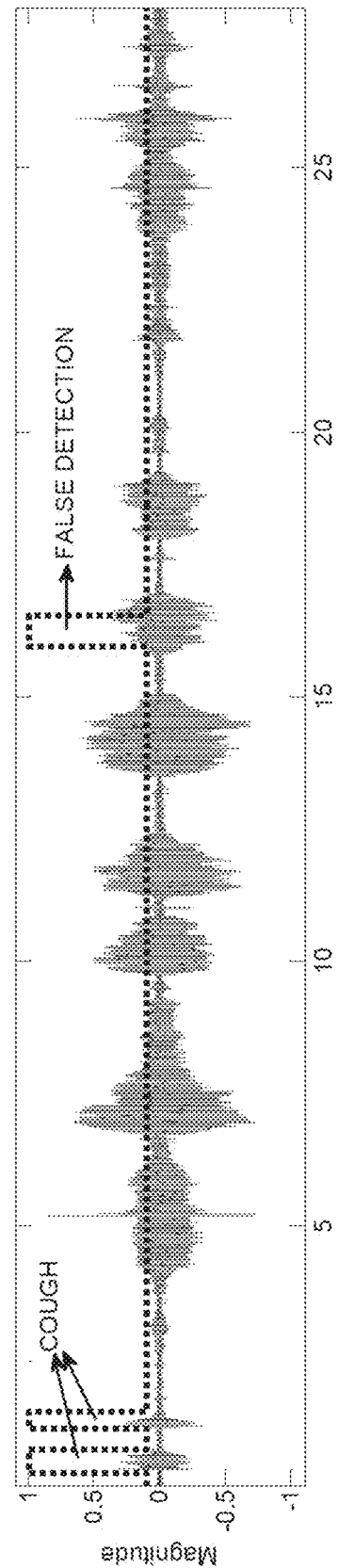
FIG. 11. The segmentation output (dashed line) of the signal which contains cough and cry sounds. Our segmentation algorithm successfully segmented two cough sounds and discarding the cry sounds. Only small part of cry sounds mistakenly detected as cough segment.

FIG. 11 illustrates the output of the segmentation method in a typical signal which contains cough sounds intermixed with cry sounds. The method successfully extracted the two cough sounds from the signal and only detected one false segment from a long duration of cry.

We show the performance of our segmentation method for M=14, ($C_m$, m=1, 2, . . . , 14) in Table 7.

TABLE 7

THE PERFORMANCE OF THE COUGH
SEGMENTATION METHOD FOR M = 14, (CM, M = 1, 2, . . . , 14).

| Data set | Sensitivity | | Specificity | |
|---|---|---|---|---|
| | mean | std | mean | std |
| TDS | 99.20 | 0.77 | 98.80 | 0.68 |
| VDS | 94.85 | 2.86 | 95.00 | 2.18 |
| TeDS | 95.07 | 3.43 | 94.76 | 4.02 |

Segmentation outcomes for each realization, $C_m$, m=1, 2, . . . , 14, were computed and the mean and the standard deviation of sensitivity and specificity were estimated (95.07±3.43% and 94.76±4.02%, respectively). The result also shows that the formation of cough segments from sub-blocks process improves the sensitivity and specificity by around 4% compared to the outcomes of sub-blocks classification. The proposed method successfully discounted sounds such as crying, vocalization, and other environmental sounds.

In this work, we recorded the cough from children in a pediatric ward in Indonesia using a non-contact sensor. We found that a non-contact sensor is preferable for this purposes because of the ease of deployment and infection control.

Our work focused on the pediatric populations less than 5.5 years which is an area left untouched by previous studies. Children in that age range are more vulnerable to respiratory diseases shown by the high rate of morbidity and mortality. Thus, investigation to develop a method for analyzing signal from the populations is extremely important.

Pneumonia/Non-Pneumonia and Wet/Non-Wet
Cough Sounds Classification Method

Figure 12:
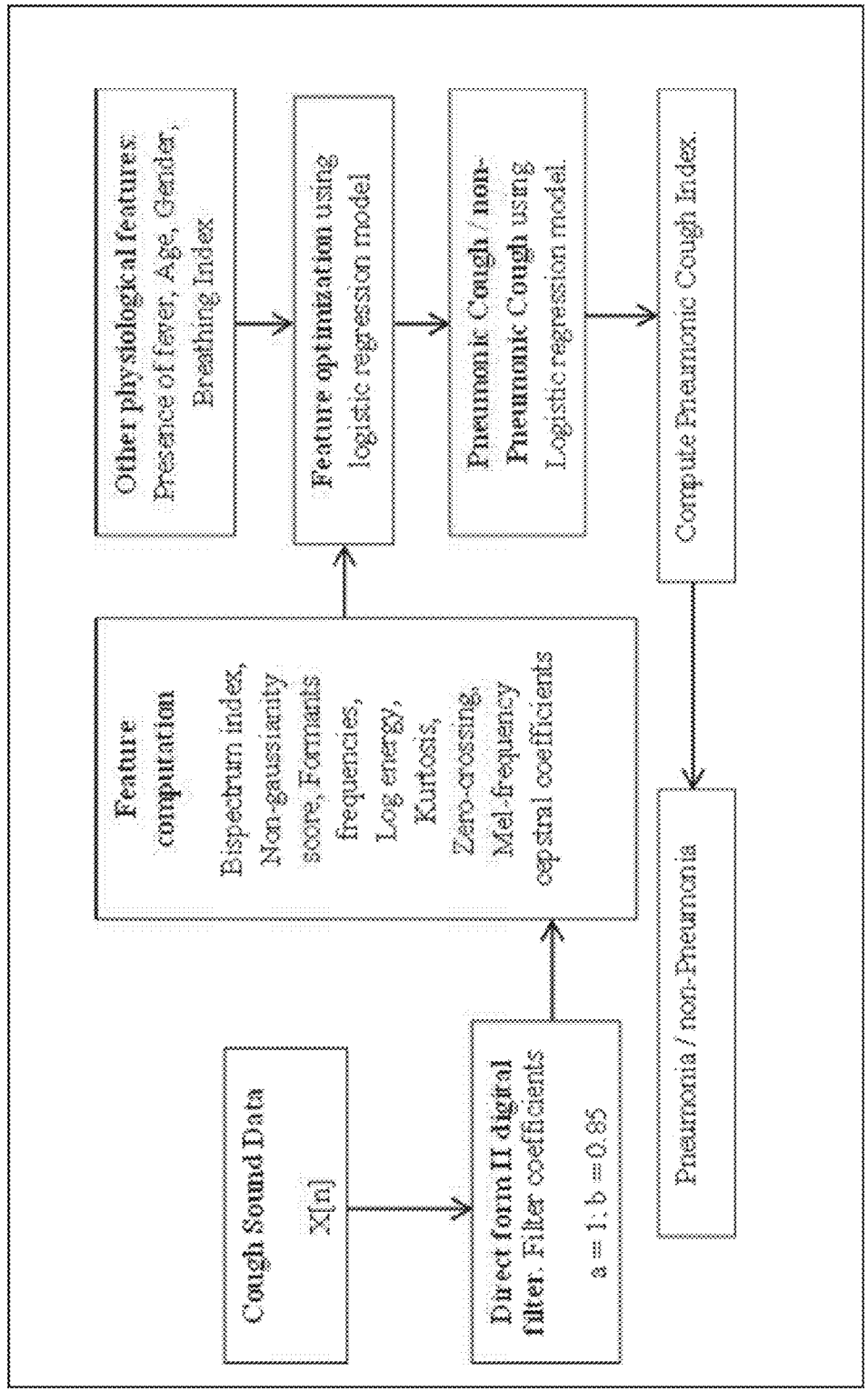
FIG. 12. Block diagram for the proposed algorithm for the Pneumonia diagnosis using cough feature.

Referring now to FIG. 12 there is shown a block diagram illustrating a method according to a preferred embodiment of a further aspect of the present invention. The method illustrated in FIG. 12 is developed for the diagnosis of particular disease states, for example Pneumonia/-non-Pneumonia classification, associated with a patient. A further embodiment of a classification method according to an embodiment of the present invention is discussed at the end of this specification.

Clinical Assessment and Inclusion-Exclusion Criteria

The data acquisition environment for this work is Respiratory Medicine Unit of the Sardjito Hospital, Gadjah Mada University, Indonesia. Our subject population includes individuals with symptoms of respiratory disease. Patients admitted to the general ward of the hospital were assessed by a clinician for the presented symptoms. All the observations were documented in a standard sheet. Observations included presence of cough, runny nose, fever, breathing difficulty, diarrhoea etc. Clinician also recorded Temperature, Breathing rate, SpO2 and Heart rate.

Table 8 lists the inclusion and exclusion criteria. All patients fulfilling the inclusion criteria were approached. An informed consent was made. Patients were recruited within first 12 hours of their admission. After the informed consent continuous sound recordings were made for next 4-6 hours.

TABLE 8

Inclusion and Exclusion Criteria Used in the study

| Inclusion Criteria | Exclusion Criteria |
|---|---|
| Patients with symptoms of chest infection: At least 2 of Cough Sputum Increased breathlessness Temperature >37.5° Consent | Advanced disease where recovery is not expected eg terminal lung cancer Droplet precautions NIV required No Consent |

A. Data Acquisition and Recording System.

The sound recordings were made in the general adult ward of the hospital. Patient shared the room with 5 other patients separated by curtains. The patients were accompanied by their family members. The attending physician regularly visited the patient, however no confidential information related to the patient was recorded. The common noise present in the recordings were from ceiling fan, foot step, speech, door banging, trolley movement and other ambiguity noises from outside the room.

Cough sound recordings were made using two systems,
  (i) Computerized data acquisition system—A high fidelity, professional quality pre-amplifier and A/D converter unit, (Model Mobile-Pre USB, M-Audio, California, USA) with a matched pair of low-noise microphones having a hypercardiod beam pattern (Model NT3, RODE, Sydney, Australia).
  (ii) Portable recording system—A high-end, light-weight portable, 2-AA battery powered audio recorder (Olympus LS-11) with two precision condenser microphones.

In both the recording setup we used a sampling rate of 44.1 kHz with a 16 bit resolution. The nominal distance from the microphone to the mouth of the patient was 50 cm, but could vary from 40 cm to 70 cm due to patient movements.

We received the digital sound data aided with the clinical diagnostic information from the hospital. Data was completely de-identified and was stored behind the secure firewall, under a strict regime of password control. The access of the data was restricted to the participant researchers individually authorized by the principle investigator.

B. Feature Computation from the Cough Sound Data

Figure 15:
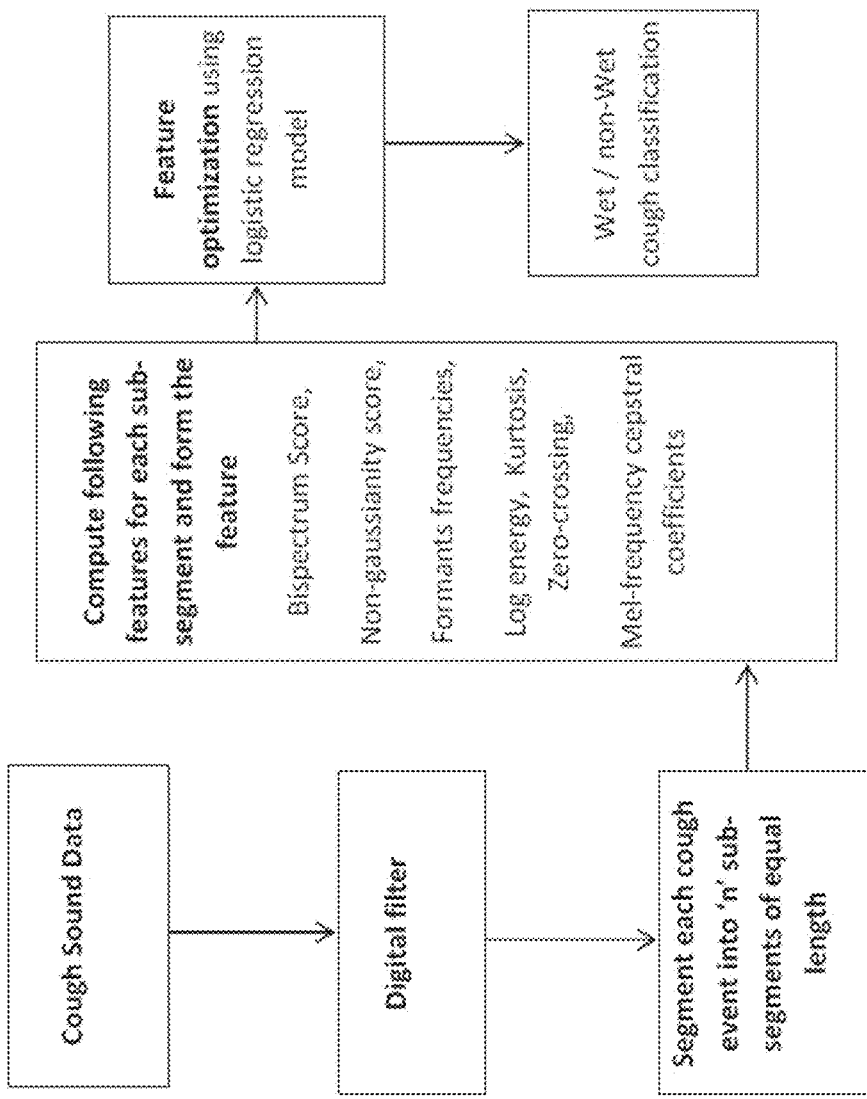

FIG. 12 shows the block diagram of the overall algorithm developed for the Pneumonia/-non-Pneumonia classification whereas FIG. 15 shows the block diagram of the algorithm developed for the Wet/non-Wet cough sound classification.

Figure 13:
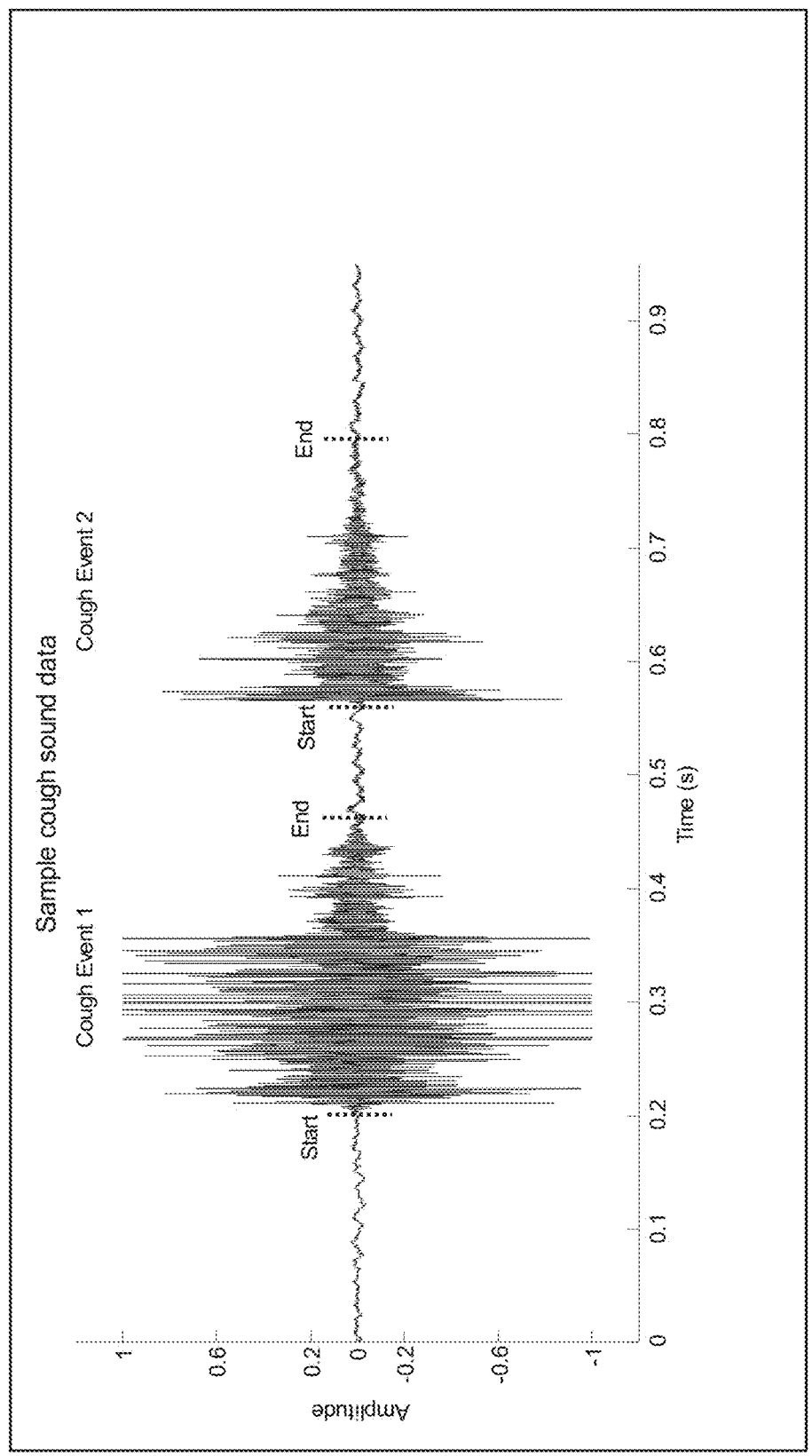
FIG. 13. Sample pneumonia cough sound. Start and end of the cough events were manually marked after carefully listening to the cough events.

FIG. 13 shows a sample of cough sound data with two cough events. Start and end of the cough events were manually marked after careful listening. After the manual scoring of start and end of cough events we followed the following steps to compute mathematical features from the cough event data.

Figure 14:
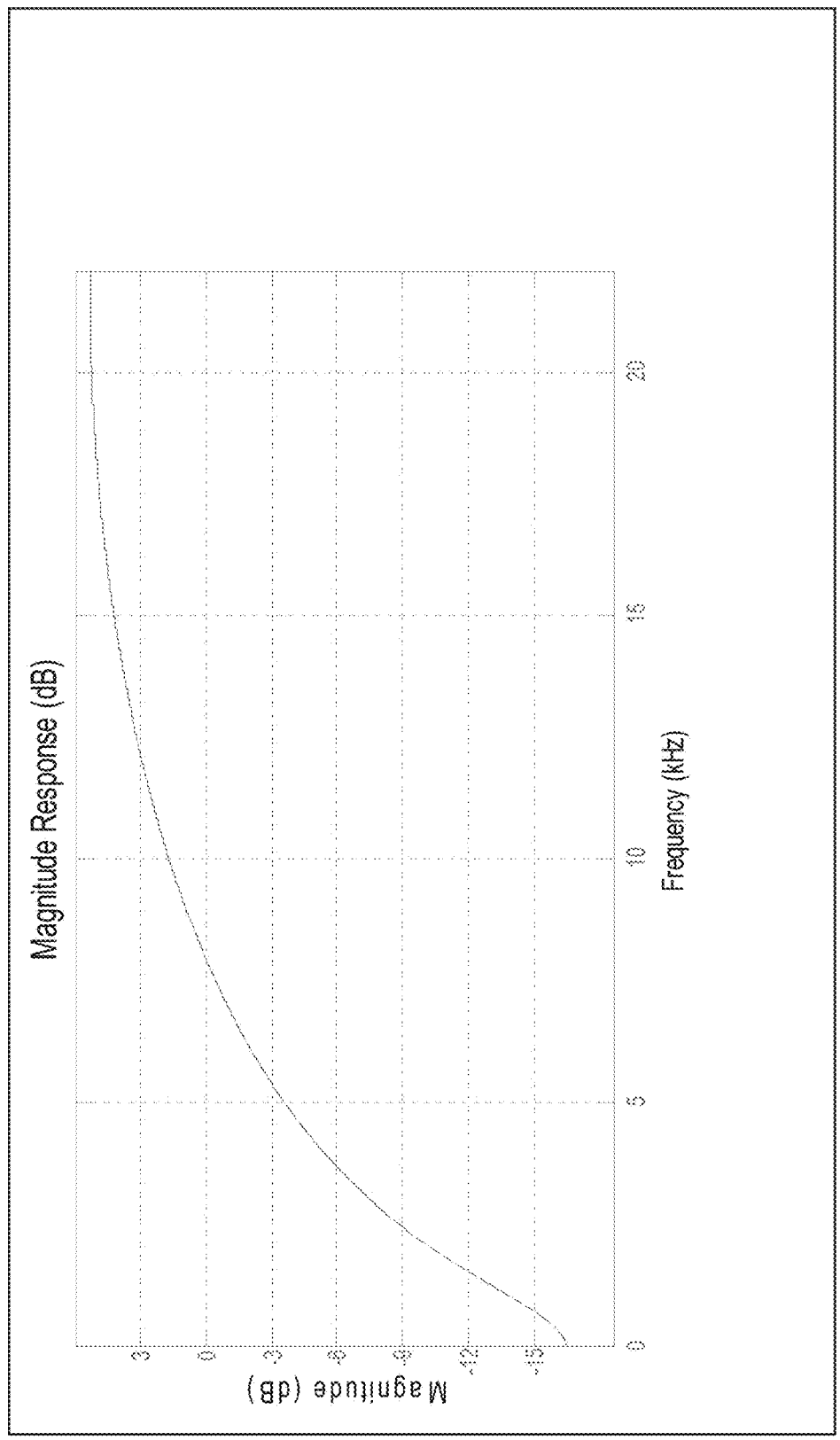
FIG. 14. Magnitude response of the digital high pass filter. Pneumonia classification method FIG. 15 Block diagram for the proposed algorithm for the Wet and Dry cough sounds classification FIG. 16. Histogram of sensitivity and specificities achieved for 200 training and testing datasets. Only selected features were used for LR model designing.

[C1]. Let x[k] denotes the $k^{th}$ sample of the discrete time cough sound. Filter x[k] using a digital high pass filter to get y[k]. The transfer function of the filter in z-transform is given by (1). FIG. 14 shows the filter response with B=[1-0.85] and A=[1].

$$Y(z) = \frac{B(1) - B(2)z^{-1}}{1 + Az^{-1}} X(z) \quad (1)$$

For the Wet/non-Wet cough sound classification divide y[k] into 'n' equal size segments. Let y"[k] represents the $n^{th}$ segment of y[k].

For pneumonia/non-pneumonia classification this sub-segmentation is not considered.

[C2]. Compute the following features from the filtered cough segment y[k] in case of pneumonia classification and from each filtered subsegment y"[k] in case of wet/non-wet classification.

1. Non-Gaussianity Score (NGS)—NGS gives the measure of non-gaussianity of a given segment of data. The normal probability plot can be utilized to obtain a visual measure of the gaussianity of a set of data. The NGS of the data segment y[k] can be calculated using (2). Note that in (2), p(k) and q(k) represents the probabilities and p and q represents the mean of the reference normal data and the analyzed data, respectively. Detail method of computing NGS can be found in [29].

$$NGS = 1 - \left( \frac{\sum_{k=1}^{N} p[k] - \overline{p}}{\sum_{k=1}^{N} q[k] - \overline{q}} \right) \quad (2)$$

2. Formants frequencies—In human voice analysis formants are referred as the resonance of the human vocal tract. They are manifested as the amplitude peak in the LPC spectrum of the acoustic signal. We included the $1^{st}$ four formant frequencies (F1, F2, F3, F4) in our feature set. Past studies in the speech and acoustic analysis have shown that F1-F4 corresponds to various acoustic features of upper airway [30]. We computed the F1-F4 by peak picking the LPC spectrum. For this work we used $14^{th}$ order LPC spectrum and its parameters were determined via Yule-Walker autoregressive method along with the Levinson-Durbin recursive procedure [31].

3. Log Energy(Log E)—The log energy for segment y[k] was computed using eq. 3

$$LogE = 10\log_{10}\left(\varepsilon + \frac{1}{N}\sum_{k=1}^{N}(y(k)^2)\right) \quad (3)$$

where ε is an arbitrarily small positive constant added to prevent any inadvertent computation of the logarithm of 0.

4. Zero crossing (Zcr)—The number of zero crossings were counted for each cough event.

5. Kurtosis (Kurt)—The kurtosis is a measure of the peaked-ness associated with a probability distribution of cough event data y[k], computed using (4), where μ and σ in (4) are mean and standard deviation of y[k].

$$kurt = \frac{E(y[k] - \mu)^4}{\sigma^4} \quad (4)$$

6. Mel-frequency cepstral coefficients (MFCC)—MFCCs are commonly used in the speech analysis systems [32]. They represent the short term power spectrum of an acoustic signal based on a cosine transform of a log power spectrum on a non-linear mel-scale of frequency. We included the 12 MFCC coefficients in our feature set.

7. Bispectrum Score (BS)—The $3^{rd}$ order spectrum of the signal is known as the bispectrum. The bispectrum can be estimated via estimating the $3^{rd}$ order cumulant and then taking a 2D-Fourier transform, this method, known as the indirect method of estimating the bispectrum, was followed. The $3^{rd}$ order cumulant $C(\tau_1, \tau_2)$ was estimated using (5) as defined in [33].

$$C(\tau_1, \tau_2) = \frac{1}{L}\sum_{k=0}^{L-1} y(k)y(k+\tau_1)y(k+\tau_2), \quad (5)$$

$$|\tau_1| \leq Q,$$

$$|\tau_2| \leq Q,$$

By applying a bispectrum window function to the cumulant estimate, windowed cumulant function $C_w(\tau_1, \tau_2)$ was obtained. We used the minimum bispectrum-bias supremum window described in [34] for the purpose.

The bispectrum $B(\omega_1, \omega_2)$ of the segment y[k] was estimated as the 2-D Fourier transform of the cumulant estimate $C_w(\tau_1, \tau_2)$ using (6). We used FFT length of 512 points.

$$B(\omega_1, \omega_2) = \sum_{\tau_1=-\infty}^{\tau_1=+\infty} \sum_{\tau_2=-\infty}^{\tau_2=+\infty} C^{yi}(\tau_1, \tau_2)e^{-j(\tau_1\omega_1+\tau_2\omega_2)} \quad (6)$$

In the frequency domain, a quantity $P(\omega;\phi,\rho)$ can be defined for the data segment y[k] such that $$P(\omega;\phi,\rho) = B(\omega,\phi\omega+\rho) \quad (7)$$

describing a one-dimensional slice inclined to the $\omega_1$-axis at an angle $\tan^{-1}\phi$ and shifted from the origin along the $\omega_2$-axis by the amount ρ, ($-\pi<\rho<\pi$). [5]. For this work we set $\phi=1$ and $\rho=0$ so that the slice of the bispectrum considered is inclined to the $\omega_1$-axis by 45 degrees and passes through the origin (i.e. the line described by $\omega_1=\omega_2$ in the ($\omega_1, \omega_2$)-plane).

Then Bispectrum Score (BS) is computed using (8). In (8) we used $\omega_1=90$ hz, $\omega_2=5$ khz, $\omega_3=6$ khz and $\omega_4=10.5$ khz, $$BI = \frac{\int_{\omega_1}^{\omega_2} P(\omega)}{\int_{\omega_3}^{\omega_4} P(\omega)} \quad (8)$$

After the feature computation, for each cough segment, in the case of the pneumonia classification we form a feature vector containing 21 features (12 from MFCC; 4—Formant frequency; 1 each from NGS, Log E, Zcr, Kurt and Bispectrum) and in the case of wet/non-wet cough classification we get a vector containing 63 features (36 from MFCC; 12—Formant frequency; 3 each from NGS, Log E, Zcr, Kurt and Bispectrum).

C. Pneumonia Classification Model and Feature Optimization

We followed a three-step process for the pneumonia classification using cough based features, which is as follows Step 1. In the first step we classified each cough event into one of the two categories, 'Pneumonic Cough' or 'non-Pneumonic Cough'. To solve this problem, we formed a feature vector for each cough event and derive a model, which can separate the cough events into two categories. Different models were derived with different feature set as shown in the Table 9.

TABLE 9

Derived logistic-regression model for classification of cough event into categories 'Pneumonic Cough' and 'non-Pneumonic Cough'.

| Features Models | Age (in months) | Presence of Fever | Breathing Index | Cough Feature |
|---|---|---|---|---|
| LR-model1 | | | | ✓ |
| LR-model2 | | | ✓ | ✓ |
| LR-model3 | | ✓ | ✓ | ✓ |
| LR-model4 | | ✓ | ✓ | ✓ |
| LR-model5 | ✓ | ✓ | ✓ | ✓ |

| Age | Breathing threshold for fast breathing |
|---|---|
| 1 months - 60 months | 40 breaths per minute |
| >60 months | 20 breaths per minute |

'✓' indicates the inclusion of that feature in model design.
Breathing index was calculated by subtracting the breathing threshold from the recorded breathing rate.

For the cough classification we used Logistic Regression statistical model. It is a generalized linear model, uses several predictors (independent variables) to estimate the probability of a categorical event (dependent variable).

In this work (pneumonia classification modelling), the dependent variable Y is assumed to be equal to "one" (Y=1) for Pneumonic Cough and "zero" (Y=0) for non-Pneumonic Cough.

A model is derived using logistic regression function to estimate the probability Y=1 (i.e cough event belong to category of 'Pneumonic Cough') given the independent variables (i.e feature set) as follows:

$$P(Y=1|x_1, x_2, x_3, \ldots x_n) = \frac{e^z}{e^z + 1} \quad (9)$$

$$z = \beta_0 + \beta_1 x_1 + \beta_2 x_2 + \ldots + \beta_n x_n \quad (10)$$

In (10) $\beta_0$ is called the intercept and $\beta_1$, $\beta_2$ and so on are called the regression coefficient of independent variables (features) $x_1$, $x_2$ respectively.

Logistic regression model were designed using the MATLAB statistical toolbox version 7.5. Features were selected to include only the best independent variables (variables with low 'p' value) that facilitate the classification, in the final model. The final model is then used to estimate the probability P and each cough event is classified as belonging to either of the two categories using a probability threshold $P_{th}$.

Step 2. In the second step for each patient, we summed number of 'Pneumonia cough' and computed an index called 'Pneumonic Cough Index (PCI)' using (9).

$$PCI = \frac{\text{Total number of Pneumonic cough}}{\text{Total number of cough}} \quad (11)$$

Step 3. In the third step we applied a predetermined threshold $PCI_{th}$ (optimized for high sensitivity while keeping specificity>75%) to the PCI to classify patient into two classes, 'Class I—Pneumonia' and 'Class II—non-Pneumonia'.

Wet/Non-Wet Cough Classification Model

For Wet and non-Wet cough classification we again used Logistic Regression statistical model. In this case, the dependent variable Y is assumed to be equal to "one" (Y=1) for Wet Cough and "zero" (Y=0) for non-Wet Cough.

A model is derived using logistic regression function to estimate the probability Y=1 (i.e cough event belong to category of 'Wet Cough') given the independent variables (i.e feature set) using (9) and (10). Features were then selected to include only the best independent variables (variables with low 'p' value) that facilitate the classification, in the final model. The final model is then used to estimate the probability P and each cough event is classified as belonging to either of the two categories using a probability threshold.

III. 3. Pneumonia Classification Results

A. Database and Clinical Diagnosis

Total of 541 cough events were analysed from the 81 subjects sound recording (minimum 2, maximum 12, and on average 6.6±2.14 cough events). Out of 81 subjects, 50 were Pneumonia patients and 31 were non-pneumonia patients. Non-pneumonia patients included with diseases such as, Asthma—11, Bronchitis—8, Rhinopharyngitis—6 and others (weezing, tonsilopharanzitis, heart disease, larangomalaysia, foreign body inhalation)—6. Chest x-ray was performed on all suspected pneumonia patients. Nineteen patients on which chest x-ray was not performed, 8 were asthma, 5 Rhinopharyngitis, 2 bronhitis and 4 other disease patients. Table 10 gives the age and gender statistics of the patient database.

TABLE 10

Age and gender statistics of the patients used in this study

| Mean Age | Min Age | Max Age | <2 months | 2-11 months | 12-60 months | >60 months | Male subjects | Female subjects |
|---|---|---|---|---|---|---|---|---|
| 41.75 ± 51.45 | 1 | 191 | 3 | 28 | 30 | 20 | 43 | 38 |

For deriving cough classification model using Logistic Regression in the section 2.D Step 1, we randomly divided our database into two groups, Training set and Testing set. To validate the model we generated 200 different training and testing dataset from the database of 81 subjects. Each training set and testing set were mutually exclusive and had 56 and 25 subjects respectively.

B. WHO Criteria for Pneumonia Diagnosis vs Clinical Diagnosis

Table 11 shows the contingency table for Pneumonia diagnosis using WHO criteria and Clinically diagnosed Pneumonia cases for our database of 81 subjects.

TABLE 11

Contingency table for pneumonia diagnosis using WHO criteria vs Clinically diagnosed Pneumonia.

|  | Sensitivity | Specificity | Accuracy |
|---|---|---|---|
| WHO criteria. [Cough OR Difficult Breathing & Fast breathing] | 92 | 26 Clinically Confirmed Diagnosis | 66.67 |

TABLE 11-continued

Contingency table for pneumonia diagnosis using WHO criteria vs Clinically diagnosed Pneumonia.

|  | Sensitivity | Specificity | Accuracy |
|---|---|---|---|
| Threshold for fast breathing used are | WHO | 46 | 23 |
| <2 months - 60 BPM | Criteria | 4 | 8 |
| 2-11 months - 50 BPM |  |  |  |
| 12-60 months - 40 |  |  |  |
| >60 months - 20 BPM |  |  |  |

BPM—Breaths per minute.

C. Pneumonia Diagnosis Based on Pneumonic Cough Index

Table 12 shows the training and testing classification results in separating cough events into two categories using designed 4 logistic regression models given in table 9.

TABLE 12

Classification results for cough events into two categories ('Pneumonic cough' and non-Pneumonic cough') using different Logistic Regression models as shown in table 3, following the method given in section 2.D Step 1. Selected cough features used to develop the model were BSG, FF1, FF2, FF4, ZCR, MFCC3 and MFCC6.

| Features | Training Dataset (374 ± 9 cough events from 56 subjects) | | | Testing Dataset (166 ± 9 cough events from 25 Subjects) | | |
|---|---|---|---|---|---|---|
| Models | Sensitivity | Specificity | Accuracy | Sensitivity | Specificity | Accuracy |
| LR-model1 | 68.84 ± 2.4 | 69.12 ± 2.4 | 68.94 ± 2.4 | 65.2 ± 8 | 64.5 ± 9 | 65 ± 5 |
| LR-model2 | 78.7 ± 2.4 | 79 ± 2.4 | 79 ± 2.4 | 73.8 ± 10 | 75.5 ± 10.4 | 74.3 ± 5.5 |
| LR-model3 | 77.9 ± 2.9 | 78 ± 2.9 | 78 ± 2.9 | 75.4 ± 9 | 72.6 ± 12 | 74.4 ± 5.7 |
| LR-model4 | 87.1 ± 2 | 87.4 ± 2 | 87.2 ± 2 | 83.5 ± 8.5 | 80.5 ± 10 | 82.3 ± 5 |
| LR-model5 | 90 ± 2.6 | 90.1 ± 2.6 | 90 ± 2.6 | 85.6 ± 8 | 80.1 ± 12 | 83.5 ± 5 |

Table 13 gives the pneumonia classification results using Pneumonic Cough Index. According to table 12, LR-Model5 gives the best classification results for cough events classification (mean sensitivity and specificity were 85.6±8% and 80.1±12% respectively). However in the pneumonia classification task LR-Model4 performed better than LR-Model5. It achieved the mean sensitivity and specificity of 86.2±9.6 and 84.3±15 respectively.

TABLE 13

Results for Pneumonic Cough Index based pneumonia diagnosis after only selected cough features were used in the model training. Cough Features selected were BI, FF1, FF2, Zcr, MFCC coefficients 4, 6 and 9.

| Features | | Training Dataset (56 Subjects) | | | Testing Dataset (25 Subjects) | | |
|---|---|---|---|---|---|---|---|
| Models | $PCI_{th}$ | Sensitivity | Specificity | Accuracy | Sensitivity | Specificity | Accuracy |
| LR-model1 | 0.4 | 83.3 ± 4 | 65.8 ± 6 | 76.7 ± 4 | 76.9 ± 12 | 60.5 ± 16 | 70.6 ± 8.3 |
| LR-model2 | 0.38 | 84 ± 3.2 | 81 ± 4 | 83 ± 3 | 80.8 ± 11.5 | 78.5 ± 12 | 79.7 ± 7.6 |
| LR-model3 | 0.4 | 87 ± 3.7 | 77 ± 4.8 | 83.4 ± 3 | 84.5 ± 9 | 70.8 ± 16 | 79 ± 7.5 |

TABLE 13-continued

Results for Pneumonic Cough Index based pneumonia diagnosis after only selected cough features were used in the model training. Cough Features selected were BI, FF1, FF2, Zcr, MFCC coefficients 4, 6 and 9.

| Features | | Training Dataset (56 Subjects) | | | Testing Dataset (25 Subjects) | | |
|---|---|---|---|---|---|---|---|
| Models | $PCI_{th}$ | Sensitivity | Specificity | Accuracy | Sensitivity | Specificity | Accuracy |
| LR-model4 | 0.4 | 90 ± 3 | 91.5 ± 4 | 90.7 ± 2.9 | 86.2 ± 9.6 | 84.3 ± 15 | 85.2 ± 7 |
| LR-model5 | 0.4 | 92.3 ± 2.8 | 88 ± 4 | 90.6 ± 2.9 | 87.4 ± 8.8 | 77.9 ± 14 | 83.6 ± 6.3 |

IV. Wet/Non-Wet Classification Results

A. Training and Testing Datasets

Total of 178 cough events from 46 subjects were analyzed. The male to female ratio of the subjects in database was 1:1. The mean age of the subjects was 3 years and 1 month. A pediatrician, with clinical and research experience of more than 20 years in the field of childhood illness with specialty in chronic cough, asthma, and other respiratory diseases, manually classified 178 cough events into Wet and non-Wet after careful listening. We consider this manual classification as the 'reference standard' against which results of automatic classification by designed LR model were compared.

Out of 178 cough events 82 were Wet and 96 were, as classified by reference standard. We used 70% (124 cough events) of the cough events for training and 30% (54 cough events) for testing the model. Training and testing cough events were randomly chosen using a random number generator. To validate the model, we generated 200 different training and testing dataset from the 178 cough events.

B. Classification Results

The mean sensitivity and specificity for Wet/non-wet classification using LR-model was 74.8±9% and 69.9±9.4% respectively for testing datasets, when all the cough features were used to train the model. Mean sensitivity and specificity values jumped to 79±9% and 72.7±8.7% when only selected cough features were used. In all 22 features were selected out of 63 after the feature optimization. The selected features were 1 each from BSG, Log E and Kurt; 2 from NGS; 3 from ZCR; 5 from formant frequency; and 9 from MFCC.

Table 14 shows the mean sensitivity, specificity, accuracy and kappa results for training and testing datasets.

The kappa agreement between the LR-model and reference method was 0.45±0.12 when all the cough features were used and 0.52±0.1 when only selected cough features were used.

TABLE 14

MEAN ± STD VALUES FOR SENSITIVITY, SPECIFICITY, ACCURACY AND KAPPA, FOR 200 DESIGNED LR MODELS

| 200 | Using all the cough features | | Using selected cough features | |
|---|---|---|---|---|
| Datasets | Training | Testing | Training | Testing |
| Sensitivity | 100 ± 0.1 | 74.8 ± 9 | 95.93 ± 2 | 79 ± 9 |
| Specificity | 100 ± 0 | 69.9 ± 9.4 | 83.4 ± 4 | 72.7 ± 8.7 |
| Accuracy | 100 ± 0.1 | 72.6 ± 6.1 | 88.7 ± 2.7 | 76.1 ± 5.5 |
| Kappa | 1 ± 0 | 0.45 ± 0.12 | 0.77 ± 0.05 | 0.52 ± 0.1 |

Figure 16:
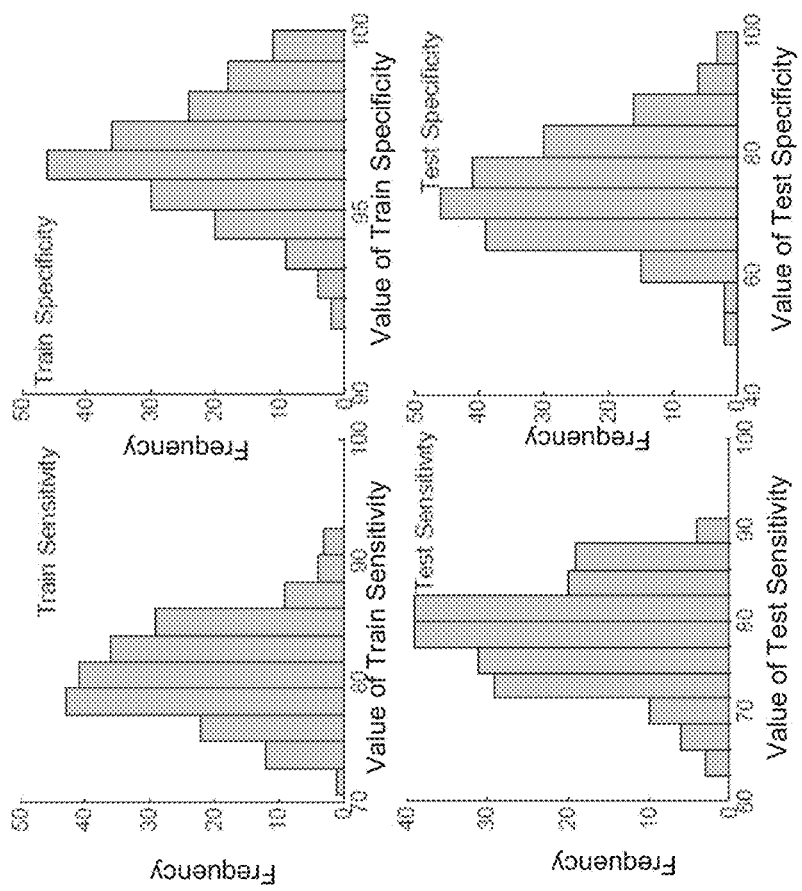

FIG. 16 shows the histogram plots for the sensitivity and specificity obtained using 200 training and testing datasets.

Table 15 shows the contingency table for the best LR-model among 200. It has the sensitivity of 90%, specificity of 80% and a high kappa agreement of 0.71.

TABLE 15

CONTINGENCY TABLE FOR BEST LR MODEL (LR = 149)

| | | Test Method | | |
|---|---|---|---|---|
| | | Wet | Non-Wet | |
| Reference Standard | Wet | 27 | 3 | 30 |
| | Non-Wet | 5 | 20 | 25 |
| | | 32 | 23 | 55 |

A second pneumonia diagnosis method, according to a further and preferred embodiment of an aspect of the invention will now be described.

V. 2. Material and Method $2^{ND}$ Pneumonia Diagnosis Method

Figure 17:
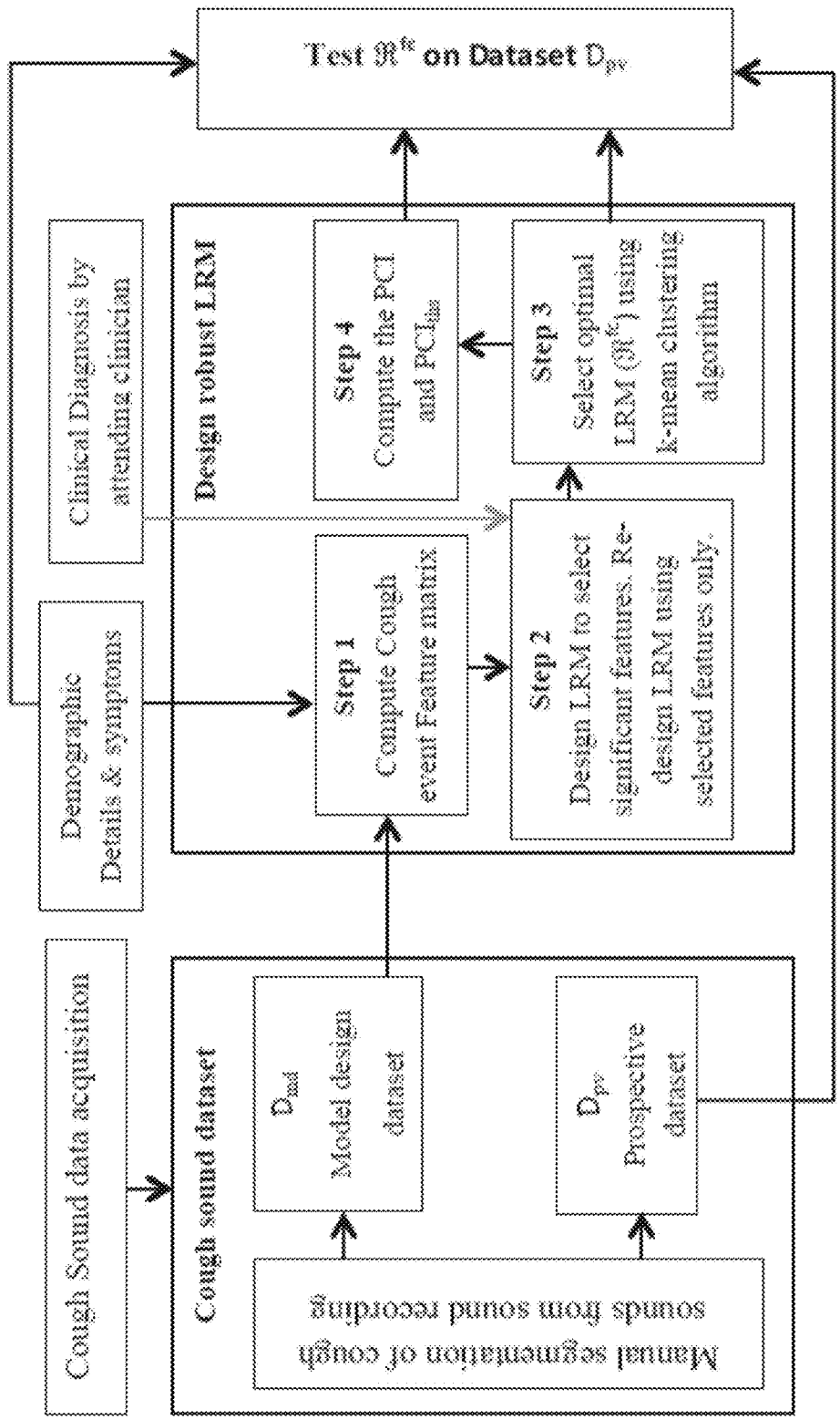
FIG. 17 is a flowchart of a method according to a further embodiment of the present invention for diagnosis of a disease state, for example pneumonia.

The overall approach of a preferred embodiment of the present invention is summarised in FIG. 17. The method consists of three main stages: the acquisition of data from subjects, the development of features and the training of pattern classifiers, and, the prospective validation and performance evaluation of the technology. In Section 2A-2C we provide details of these steps.

D. The Development of the Cough Sound Database

The clinical data acquisition environment for this work is Respiratory Medicine Unit of the Sardjito Hospital, Gadjah Mada University, Indonesia. Table 16 lists the inclusion and exclusion criteria of subjects.

TABLE 16

| Inclusion Criteria | Exclusion Criteria |
|---|---|
| Patients with symptoms of chest infection: At least 2 of Cough Sputum Increased breathlessness Temperature >37.5° Consent | Advanced disease where recovery is not expected eg terminal lung cancer Droplet precautions NW required No Consent |

Patients suspected of acute respiratory illness such as pneumonia, bronchiolitis, bronchitis, asthma, rhinopharyngitis etc. were recruited for the study. An informed consent was made using form approved by the human ethics committees of Gadjah Mada University and The University of Queensland. Patients were recruited within the first 12 hours of their admission.

A pediatric clinician assessed the patient for the presented symptoms. All the observations such as the presence of cough, runny nose, fever, breathing difficulty, diarrhoea etc. were documented in a standard sheet. The database also contained routine demographic information and the results of clinical (eg. chest auscultation, breathing rate, oxymetry, temperature) as well as laboratory (eg: blood, sputum analysis) investigations. The reference standard used for Pneumonia diagnosis in this discussion is the overall diagnosis provided by physicians, on the basis of clinical presentation, laboratory tests, chest X-ray and the clinical course of the disease. In order to minimize the radiation exposure to children, X-ray was performed only on subjects clinically suspected of pneumonia, or if there was a clear clinical need for it. Thus, not all subjects in our database had undergone X-ray imaging.

After the initial medical assessment, sound recordings were made in the natural environment of the respiratory ward. We collected sound data records of 6-8 hr durations from each patient, using bedside microphones (Rode® NT7 or Olympus® LS11, 44.1 kHz sampling rate). The distance from the mouth to the microphone could vary between 40 cm to 70 cm depending on the position of the patient's head. The inventors' objective has been to develop technology that is robust against intensity variations, such that the distance from the mouth to the recording device does not play any significant role in the diagnosis.

We used a total of 91 patients (63 pneumonia and 28 non-pneumonia subjects) to develop and validate our technology. Diseases such as bronchiolitis, asthma, bronchitis, pharyngitis, laryngomalacia are lumped within the non-pneumonia group. Details of the subjects are given in FIG. 18. The overall dataset at our disposal was separated into two non-overlapping groups: the Model Development Dataset ($D_{md}$) and the Prospective Validation Dataset ($D_{pv}$). These two datasets were completely independent of each other. The sets $D_{md}$ and $D_{pv}$ did not share either coughs or any subjects. Patients were assigned to each group based on the order of presentation to the respiratory clinic of the hospital. $D_{md}$ and $D_{pv}$ consisted of $N_{md}=66$ and $N_{pv}=25$ subjects respectively.

Figure 19:
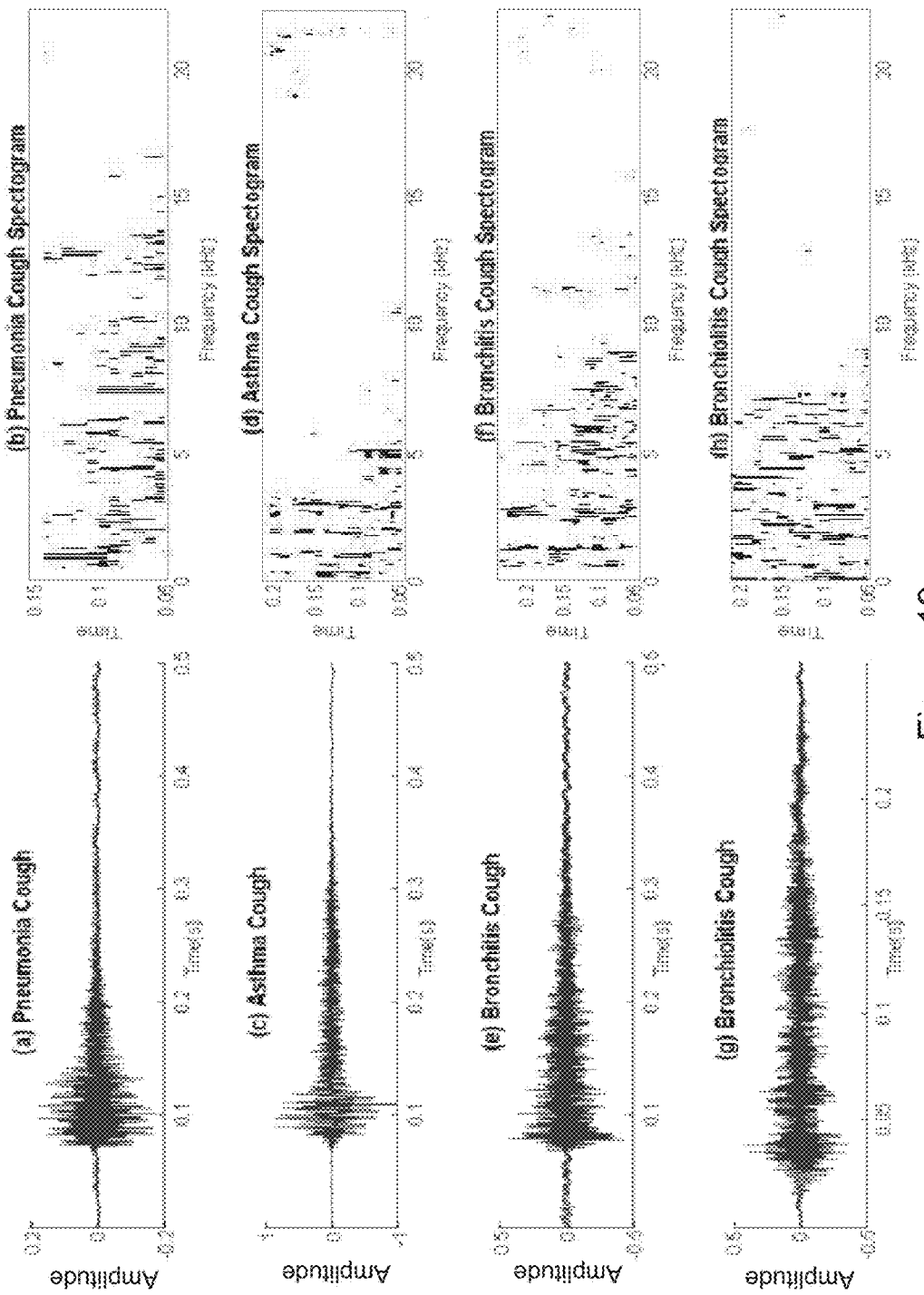
FIG. 19 shows typical examples of (a) pneumonia-cough, (c) asthma-cough, (e) bronchitis-cough and (g) bronchiolitis-cough waveforms and their corresponding power spectrogram.

Sound data from each subject consisted of about 6-8 hrs or continuous recordings. Cough sounds were manually segmented after a careful listening process. There is no accepted method for automatic identification of coughs and the manual analysis is still used as the gold standard in clinical work as well as in research literature. FIG. 19 shows typical examples of (a) pneumonia-cough, (c) asthma-cough, (e) bronchitis-cough and (g) bronchiolitis-cough waveforms and their corresponding power spectrogram. A clear characteristic difference between the pneumonia-cough and other-coughs in duration and power spectrogram magnitude can be seen.

E. Feature Extraction and Pattern Classifier Design

We used the Model Development Dataset $D_{md}$ for the work described in this section. Let $C_{md}$ be the total number of coughs events from the subjects in $D_{md}$. The approach taken in here uses a leave-one-out model building and validation process to develop features and optimize model parameters. Within this framework, our method can be described in four major processing steps (see FIG. 17), Step-1 to Step-4 as described below.

In the first step we compute a feature matrix. In the second step we design automatic classifiers using the feature matrix from step 1 to classify cough sounds into 'pneumonic cough' and 'non-pneumonic cough' classes. In the third step we select an optimal classifier and in the fourth step we define a new index called Pneumonic Cough Index (PCI) to identify patients with pneumonia.

Step-1: Extraction and Augmentation of Cough Features

In this step, our first target is to extract features from cough sounds to be used in the pneumonia diagnosis algorithm. Mathematical features from each cough event in $D_{md}$ were computed as follows:

[1]. Let x denotes a discrete time sound signal from an arbitrary cough event.

[2]. Segment x into 'n=3' equal size non-overlapping sub-segments. In the literature[19], clinicians and scientist alike have described cough sounds consisting of 3 phases, (i) initial opening burst, (ii) followed by noisy airflow and last (iii) glottal closure. It has been shown that these phases carry different significant information specific to quality of cough. On this basis we divided each cough segments into n=3 sub-segments. Let $x_i$ represents the $i^{th}$ sub-segment of x, where i= 1, 2, 3, . . . , n.

[3]. For each of the sub-segments $x_i$ compute the following features: Bispectrum Score (BGS), Non-Gaussianity score (NGS), the first four formant frequencies (FF), log energy (Log E), zero crossing (ZCR), kurtosis (Kurt), and twelve Mel-frequency cepstral coefficients (MFCC). Note that we do not make use of the $0^{th}$ coefficient of MFCC, which represents energy, in the signal $x_i$,

[4]. Repeat steps (i)-(iii) for all $C_{md}$ cough events in $D_{md}$.

This process leads to a candidate cough feature matrix $M_c$ of the size $C_{md} \times C_f$ for each sub-segment $x_i$. Where $C_f=63$ represents cough based features and $C_{md}$ is the total cough events in database $D_{md}$.

In the simplest form of the diagnostic algorithm, we will only be using cough-based features to diagnose pneumonia. However, we recognize the existence of some simple clinical measurements that can be used to improve our algorithms at minimal cost in complexity. The WHO algorithm for resource-poor areas, Table 17, uses the age and breathing rates, and other researchers have used the existence of fever.

TABLE 17

| | |
|---|---|
| Screening in criteria | Cough or difficult breathing |
| Criterion for Pneumonia | Cough and fast breathing. Threshold for fast breathing depends on the child's age.<br>2-11 months - 50 Breaths Per Minute<br>12-60 months - 40 Breaths Per Minute |
| Criterion for Severe Pneumonia or Very Sever Pneumonia | Cough and fast breathing with general danger signs such as<br>Lower chest wall indrawing<br>Stridor in calm child |

While none of these alone or in combination have yielded the desired diagnostic performance in remote areas, these measurements have the potential to augment cough-derived features. Inspired by the WHO algorithm that uses age as one of the parameters, we used age in months as a candidate parameter in our models. We also used the presence or absence of fever as a binary variable. In the WHO algorithm, breathing rate is used as the prime parameter in diagnosing pneumonia. In our work, we propose a new measure (see (1)), which we call the Breathing Index (BrI), to capture breathing rate elevations in pneumonia.

$$BrI = \begin{cases} BR - 20 & \text{if Age} \geq 60 \text{ months} \\ BR - 40 & \text{otherwise} \end{cases} \quad (1)$$

In (1) BR is breathing rate and Age is age of the patient in months. While fever is a common symptom of pneumonia, it is not specific to pneumonia. A similar observation holds for the breathing rate. Table 18 shows the candidate feature set $F^c = \{C_f, f_1, f_2, \ldots, f_f\}$, where $C_f$ represents cough-derived features and the rest denotes augmented features used in our models.

TABLE 18

Six different combinations of features used to form feature matrix in section 2-B [Step 1]. Here a tick indicates the inclusion of that feature in the model design. Breathing index was calculated by subtracting the breathing threshold from the recorded breathing rate.

| Features Combination | Age (in months) | Presence of Fever | Breathing Index | Cough Feature (#66) |
|---|---|---|---|---|
| $F^1$ (All cough features. $C_f$) | | | | ✓ |
| $F^2$ ($C_f$ + BrI) | | | ✓ | ✓ |
| $F^3$ ($C_f$ + Fever) | | ✓ | | ✓ |
| $F^4$ ($C_f$ + Age) | ✓ | | | ✓ |
| $F^5$ ($C_f$ + Fever + BrI) | | ✓ | ✓ | ✓ |
| $F^6$ ($C_f$ + Age + Fever + BrI) | ✓ | ✓ | ✓ | ✓ |

The final features in our algorithms will be drawn from the group of candidate features. Details of the feature selection, model development and validation will be described in Step-2 below.

[Step 2] Feature Selection and Automatic classifier design—
The inventors used Logistic-regression model (LRM) as the preferred pattern classifier however those skilled in the art will appreciate that other classifier methods are also applicable. LRM is a generalized linear model, which uses several independent features to estimate the probability of a categorical event (dependent variable). In this work, the dependent variable Y is assumed to be equal to "one" (Y=1) for pneumonic cough and "zero" (Y=0) for non-pneumonic cough. Cough events drawn from a subject with a diagnostic classification of pneumonia are labelled pneumonic coughs and vice versa. A model is derived using a regression function to estimate the probability Y given the independent cough features (i.e. $F^c = \{C_f, f_1, f_2, \ldots, f_f\}$) as follows:

$$Prob(Y = 1 | f_1, f_2, f_2, \ldots f_F) = \frac{e^z}{e^z + 1} \quad (2)$$

$$z = \beta_0 + \beta_1 f_1 + \beta_2 f_2 + \ldots + \beta_n f_F \quad (3)$$

In (2) and (3) $f_1, f_2, \ldots f_F$ are the elements of feature vector $F^c$ (independent variables), $\beta_0$ is called the intercept and $\beta_1, \beta_2$ and so on are called the regression coefficient of independent variables. To select the optimal decision threshold $\lambda$ from Y (that the cough is pneumonic if Y is above $\lambda$, otherwise non-pneumonic) we used the Receiver-Operating Curve (ROC) analysis.

We used a leave-1-out cross validation (LOV) technique for the LRM design. As the name suggests, LOV technique involves using data from all the patients except one to train the model and cough events from one patient to validate the model. This process was systematically repeated such that each patient in $D_{md}$ was used as the validation data exactly one time. At the end of this process, we end up in $N_{md}$ different LRM models. To evaluate the performance of the designed $N_{md}$ LRMs, performance measures such as Sensitivity, Specificity, Accuracy, Positive Predicted Value (PPV), Negative Predicted Value (NPV), Cohen's Kappa (K) statistic were computed.

(i) Feature Selection: Feature selection is a technique of selecting a sub-set of relevant features for building a robust learning model. Theoretically, optimal feature selection requires exhaustive search of all possible subsets of features. However, to do so for large number of features it will be computationally intensive and impractical. Therefore we searched for satisfactory set of features using p-value. In LRM design a p-value is computed for each feature and it indicates how significantly that feature contributed in the development of the model. Important features have low p-value. We used this property of LRM to select a reasonable combination of features (independent variables with low p-value) that facilitate the classification, in the model during the training phase. Compute mean p-value for $F^c$ features over $N_{md}$ LRMs. Select the features with mean p-value less than a threshold value given by $p_{ths}$. Let $C_f^s$ be the sub-set of selected cough features from $C_f$ and $F^c_s$ be the candidate features set formed by augmenting features with selected cough features.

(ii) Robust LRM design: Once the subset $F^c_s$ is known, we use those features and build a new set of LRMs once again following another leave-one-out validations process. At the end of this process, we have $N_{md}$ number of LRMs using $F^c_s$ as the input feature set.

[Step 3] Selecting a good model from $N_{md}$ LRMs—From the candidate LRMs that use the selected features $F^c_s$ as the input features, we selected one model as the best based on the k-mean clustering algorithm. In the k-mean clustering algorithm, target is to divide q data points in d-dimensional space into k clusters, so that within the cluster sum of squared distance from the centroid is minimized. Problem in our hand is to select a good model from the $N_{md}$ models available to us. To do so we divided $N_{md}$ models in d-dimensional space into k=2 clusters, i.e. high performance model cluster and low-performance model cluster. We set space dimension d equal to model parameters plus three performance measures (sensitivity, specificity and kappa). Then from the cluster of the high performance models, we selected that model which had the lowest mean square error value with respect to the centroid. Let $\mathfrak{R}^{fc}$ represent the selected LRM and $\lambda \mathfrak{R}_{fc}$ is the corresponding probability decision threshold (value determined using ROC curves such that the classifier performance is maximized) for a specific combination of features.

Once $\mathfrak{R}^{fc}$ is chosen, we fix all the parameters of the model and completely terminate the training process. The model $\mathfrak{R}^{fc}$ is then used as the best model to classify each individual cough event into 'pneumonic-cough' or 'non-pneumonic-cough' groups.

[Step 4] Pneumonic Cough Index—In this step, for each $N_{md}$=66 patient in the $D_{md}$ we compute a Pneumonic Cough Index (PCI) using the below definition.

Definition of Pneumonic Cough Index (PCI): Let 'P' be the total number of coughs recorded and analysed from a patient. And let 'Q' out of 'P' coughs are classified as pneumonic cough using selected LRM $\Re^{fc}$ in step 3. Then the PCI index for the patient is computed as $$PCI = Q/P \quad (4)$$

Then using the ROC analysis we computed a threshold $PCI_{th}$ (optimized for high sensitivity while keeping acceptable specificity) to classify patient into two classes, 'Pneumonia' and 'non-Pneumonia'.

F. Testing of Selected LRM $\Re^{fc}$ and PCI on $D_{pv}$

Following the procedure described in section 2-B [Step 1] and using the cough events sound data from $N_{pv}=25$ patients in dataset $D_{pv}$, compute the cough event feature matrix $M_c$ $D^{pv}$ of size $C_{pv} \times C_f$. $C_{pv}$ is total cough events in $D_{pv}$ and $C_f=63$ represents cough based features. Form $M_cD^{pv}$ from $M_{fc}{}^sD^{pv}$ by augmenting clinical features with selected cough features $C_f^s$. Use selected LRM $\Re^{fc}$ in Section 2-B [Step 3] to classify data in $M_{fc}{}^s\Re^{pv}$ into classes 'pneumonic cough' and 'non-pneumonic cough'. Then using (4) compute the PCI for each patient in $D_{pv}$. Applying $PCI_{ths}$ computed in section 2-B [step 4] to PCI and classify patients as 'Pneumonia' if $PCI>PCI_{th}$ and 'non-pneumonia' otherwise.

Compare the results of automatic classification by PCI with that of attending clinician and compute the performance measures.

D. Database and Clinical Diagnosis

Figure 18:
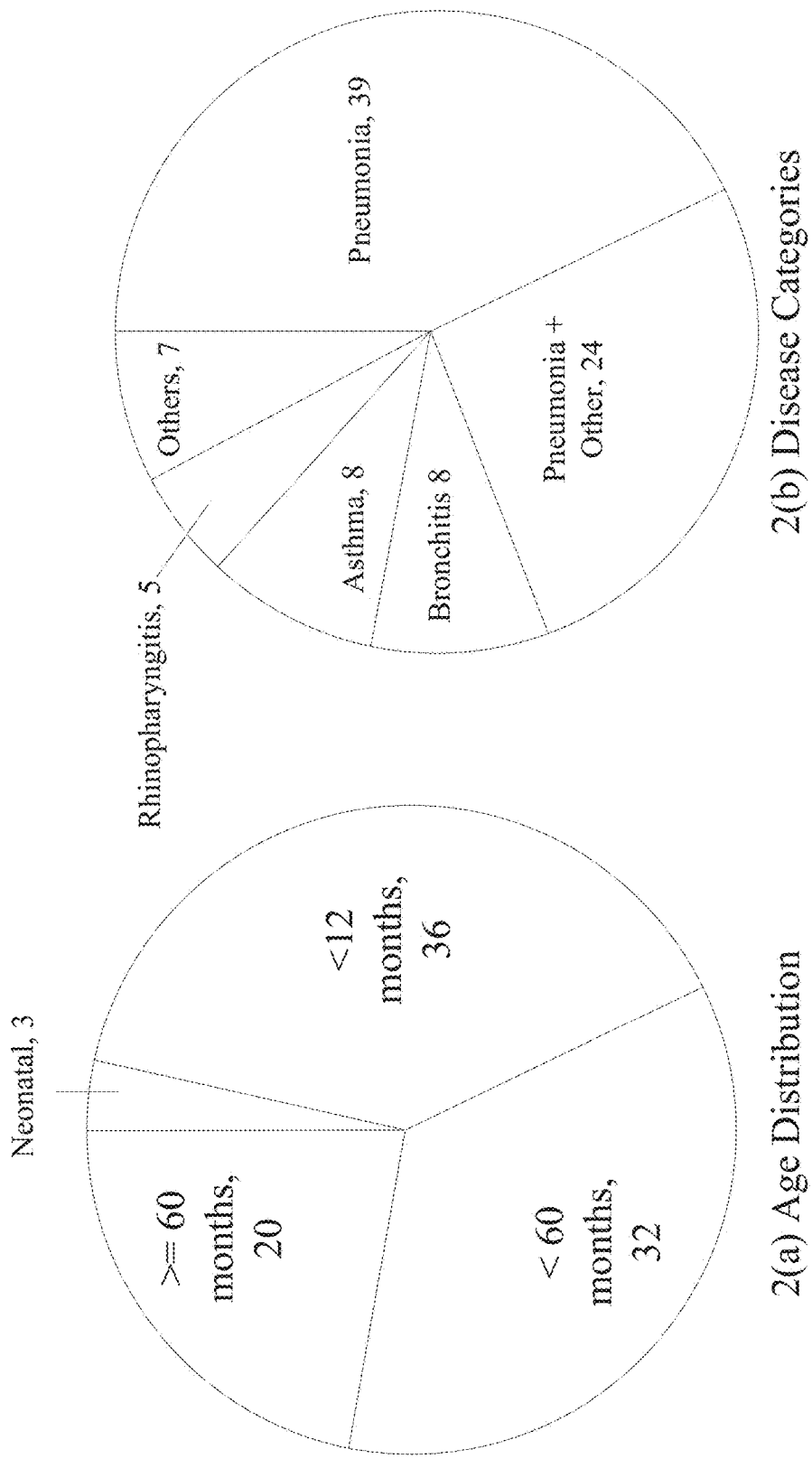
FIG. 18 comprises charts presenting details of subjects associated with application of the method of FIG. 17.

Sound recordings from N=91 patients (48 males and 43 females) were used. The mean age of the subjects was 3 years and 1 month (standard deviation 3 years and 11 months). The age range of the subjects varied from 1 month to 15 years. Of the 91 subjects, 63 were Pneumonia patients and 28 were non-pneumonia patients. Non-pneumonia patients had diseases such as Asthma, Bronchitis, Rhinopharyngitis and others (wheezing, tonsilopharyngitis, heart disease, foreign body inhalation). Chest X ray (CXR) was performed on 65 patients to confirm the diagnosis. Of the 26 patients on whom CXR was not done, eight had been clinically diagnosed as pneumonic and 17 as non-pneumonia patients. FIG. 18 gives the distribution of age and disease categories in the database.

E. Cough Sounds Characteristics

FIG. 4 shows a typical example of pneumonia-cough, asthma-cough, bronchitis-cough and bronchiolitis-cough waveforms and their corresponding power spectrogram. We can see a clear characteristic difference between the pneumonia-cough and other-coughs in duration and power spectrogram magnitude. The pneumonia-cough is of short duration with widely spread power spectrum up-to 20 kHz. On the contrary other coughs are of long duration with power spectrum up-to 15 kHz. The mean duration of pneumonia-cough (0.26±0.7s using n=401 coughs) was significantly less (2-tailed t-test, p<0.005, t=−8.6786) than that of other cough (0.32±0.08s using n=198 coughs). The cough sound waveforms were generally clean with high signal-to-noise-ratio (SNR). The mean SNR for the $D_{md}$ was 15.8±5.6 db (maximum=28.05 db and minimum=2.08 db) and that for $D_{pv}$ was 16.7±5 db (maximum=26.7 db and minimum=7.9 db).

F. Pneumonia Dagnosis Bsed on WHO Criteria

Table 19 shows the contingency table for Pneumonia diagnosis using WHO criteria and clinically diagnosed Pneumonia.

| | Sensitivity | Specificity | Accuracy |
|---|---|---|---|
| WHO criteria. [Cough and/or breathing difficulty] Threshold for fast breathing used are <2 months - 60 BPM 2-11 months - 50 RPM 12-60 months - 40 >60 months - 20 BPM | 86% | 22% | |

WHO guidelines for pneumonia diagnosis in community settings are designed for children with age group of 2 months to 5 years[18]. "Infants less than 2 months with signs of pneumonia are referred promptly to the nearest health facility because they are at high risk of suffering severe illness or death"[18]. Therefore table 19 is generated using #68 subjects in our database, which falls in the age range 2 months to 5 years. WHO criteria achieved a high sensitivity of 83% in picking clinically confirmed pneumonia cases, however presented with a poor specificity of 47%.

G. Pneumonia Diagnosis using Designed Model on Training/Validation Dataset

From N=91 patients a total of C=599 cough events were analysed. On the average 6.6±2 cough events per patients were analysed (minimum=2 and maximum=12 per each patient). In section 2-A, we divided N=91 patients into two datasets $D_{md}$ (Training/Validation dataset) and $D_{pv}$ (Prospective study dataset). $D_{md}$ has data from $N_{md}=66$ patients with $C_{md}=440$ cough events (average=6.7±2, minimum=2, maximum=12). $D_{pv}$ has data from $N_{pv}=25$ patients with $C_{pv}=159$ cough events (average=6.4±1, minimum=5, maximum=10).

Feature Matrix: Following the method given in section 2-B [Step 1] we computed feature matrix $M_c$. We used n=3 to divide each cough segment into 3 sub-segments. Setting n=3 gave 63 mathematical features from each cough event, consisting of (36 MFCC)+(12 FF)+(3 each of BSG, NGS, Log E, ZCR and Kurt). Augmenting clinical features with cough features 6 cough event feature matrix $M_{fc}$ were created. Following LOV technique $N_{md}=66$ LRMs were designed (since $N_{md}=66$ patients in $D_{md}$).

Pneumonic Cough Classification using LRM before feature selection: For $F^1$ feature combination (only mathematical features of cough), the mean training sensitivity and specificity over 66 LRMs in classifying cough events into Pneumonic and non-pneumonic cough classes were 81±1%. Validation sensitivity and specificity were 63% and 52% respectively. When BrI was included as feature, sensitivity and specificity of validation set jumped to 71% and 55% respectively. And when all the features, Age, presence of fever and BrI were included in train LRM along with mathematical features of cough, sensitivity and specificity further increased to 73% and 62% respective. Table 20 gives the performance of the model in classifying cough events into Pneumonic and non-pneumonic cough classes using different combination of features.

TABLE 20

Performance of the LRM models in classifying cough events into 'pneumonic cough' and 'non-pneumonic cough' classes on training/validation dataset $D_{md}$ when all the features were used to train the model. $F^c$ represents the different feature combination.

| $F^c$ | Training | | | | | | Validation | | | | | |
|---|---|---|---|---|---|---|---|---|---|---|---|---|
| | Sens | Spec | Acc | PPV | NPV | K | Sens | Spec | Acc | PPV | NPV | K |
| $F^1$ (All cough features, $C_f$) | 81 ± 1% | 81 ± 1% | 81 ± 1% | 90 ± 1% | 68 ± 1% | 0.59 ± 0.01 | 63% | 52% | 59% | 73% | 40% | 0.13 |
| $F^2$ ($C_f$ + BrI) | 85 ± 1% | 85 ± 1% | 85 ± 1% | 92 ± 1% | 73 ± 2% | 0.67 ± 0.02 | 71% | 55% | 66% | 77% | 48% | 0.26 |
| $F^3$ ($C_f$ + Fever) | 83 ± 1% | 83 ± 1% | 83 ± 1% | 91 ± 1% | 70 ± 2% | 0.62 ± 0.01 | 68% | 54% | 63% | 75% | 45% | 0.20 |
| $F^4$ ($C_f$ + Age) | 85 ± 1% | 85 ± 1% | 85 ± 1% | 92 ± 1% | 73 ± 1% | 0.68 ± 0.02 | 70% | 56% | 65% | 77% | 47% | 0.24 |
| $F^5$ ($C_f$ + Fever + BrI) | 87 ± 1% | 87 ± 1% | 87 ± 1% | 93 ± 1% | 76 ± 1% | 0.71 ± 0.02 | 70% | 59% | 67% | 78% | 49% | 0.28 |
| $F^6$ ($C_f$ + Age + Fever + BrI) | 91 ± 1% | 92 ± 1% | 91 ± 1% | 96 ± 1% | 83 ± 2% | 0.8 ± 0.02 | 73% | 62% | 70% | 80% | 53% | 0.34 |

Pneumonic Cough Classification using LRM after feature selection: Following the procedure described in section 2-B [Step-2] and using p-value, we selected features for each of $F^c_s$. Table 6 gives the details of the cough features selected and the $p_{ths}$ used for selection.

TABLE 21

30 cough features were selected from $C_f = 63$ features after the feature selection step.

| | | | Features selected | | | | |
|---|---|---|---|---|---|---|---|
| $P_{ths}$ used | BSG | NGS | FF | LogE | Kurt | ZCR | MFCC |
| 0.23 | 2 | 1 | 3 | 2 | 0 | 3 | 19 |

Table 22 gives the performance of the model after feature selection in classifying cough events into Pneumonic and non-pneumonic cough classes.

TABLE 22

Performance of the LRM models in classifying cough events into 'pneumonic cough' and 'non-pneumonic cough' classes on training/validation dataset $D_{md}$ when selected features were used to train the model.

| $F^c_s$ | Training | | | | | | Validation | | | | | |
|---|---|---|---|---|---|---|---|---|---|---|---|---|
| | Sens | Spec | Acc | PPV | NPV | K | Sens | Spec | Acc | PPV | NPV | K |
| $F^1_s$ ($C^s_f$) | 79 ± 1% | 79 ± 1% | 79 ± 1% | 89 ± 1% | 64 ± 1% | 0.54 ± 0.01 | 69% | 64% | 68% | 80% | 50% | 0.31 |
| $F^2_s$ ($C^s_f$ + BrI) | 82 ± 1% | 83 ± 1% | 83 ± 1% | 91 ± 1% | 70 ± 1% | 0.60 ± 0.02 | 72% | 69% | 71% | 83% | 54% | 0.39 |
| $F^3_s$ ($C^s_f$ + Fever) | 82 ± 1% | 82 ± 1% | 82 ± 1% | 91 ± 1% | 69 ± 1% | 0.61 ± 0.02 | 72% | 60% | 68% | 79% | 51% | 0.31 |
| $F^4_s$ ($C^s_f$ + Age) | 82 ± 1% | 82 ± 1% | 82 ± 1% | 91 ± 1% | 69 ± 2% | 0.71 ± 0.02 | 71% | 67% | 70% | 82% | 53% | 0.36 |
| $F^5_s$ ($C^s_f$ + BrI + Fever) | 86 ± 1% | 87 ± 1% | 86 ± 1% | 93 ± 1% | 75 ± 1% | 0.70 ± 0.01 | 77% | 74% | 76% | 86% | 60% | 0.49 |
| $F^6_s$ ($C^s_f$ + BrI + Age + Fever) | 89 ± 1% | 89 ± 1% | 89 ± 1% | 94 ± 1% | 79 ± 1% | 0.75 ± 0.01 | 80% | 73% | 78% | 86% | 63% | 0.51 |

According to Table 22 we see a general improvement in model performance after the feature selection for all $F^c$. The validation sensitivity and specificity for $F^1_s$, where only mathematical feature from cough events were used to train the model, increased to 69% and 64% respectively with K=0.31. Best sensitivity and specificity of 80% and 73% respectively were achieved for $F^6_s$.

PCI based classification: From $N_{md}$=66 designed LRMs for each $F^c_s$ using data from $D_{md}$, robust model $\Re^{fc}$ was selected using k-mean clustering method as discussed in section 2-B [Step 3]. The chosen model $\Re^{fc}$ and all its parameters were fixed for use in step [4] of section 2-B. Using the definition given in section 2-B [Step 4], PCI index was computed for each patient. By ROC analysis a $PCI_{th}$ was selected and applied on PCI to classify patients into 'Pneumonia' and 'non-Pneumonia'. Table 23 shows the PCI based pneumonia/non-pneumonia classification results for 6 feature combinations $F^c_s$.

TABLE 23

Performance of the selected LRM $\Re^{fc}$ on train/validation dataset $D_{md}$, in diagnosing pneumonia using Pneumonic Cough Index.

| Selected LRM model | Dataset $D_{md}$ | | | | | | |
|---|---|---|---|---|---|---|---|
| | $PCI_{tbs}$ | Sens | Spec | Acc | PPV | NPV | K |
| $\Re^{f1}$ ($C^s_f$) | 0.5 | 93% | 90.5% | 92% | 95% | 86% | 0.83 |
| $\Re^{f2}$ ($C^s_f$ + BrI) | 0.5 | 93% | 90.5% | 92% | 95% | 86% | 0.83 |
| $\Re^{f3}$ ($C^s_f$ + Fever) | 0.5 | 91% | 86% | 89% | 93% | 82% | 0.76 |
| $\Re^{f4}$ ($C^s_f$ + Age) | 0.5 | 91% | 91% | 91% | 95% | 83% | 0.80 |
| $\Re^{f5}$ ($C^s_f$ + BrI + Fever) | 0.5 | 93% | 90.5% | 92% | 95.5% | 86% | 0.83 |
| $\Re^{f6}$ ($C^s_f$ + BrI + Age + Fever) | 0.67 | 91% | 90.5% | 91% | 95% | 83% | 0.8 |

All the feature combinations achieved a sensitivity and specificity greater than 90% except for $F^3_s$ which registered a slightly lower specificity of 86%. $F^1_s$ which uses only cough features has the sensitivity of 93% and specificity 90.5% with K=0.83.

H. Pneumonia Diagnosis using Designed Model on Prospective Study Dataset

The model $\Re^{fc}$ selected in section 2-B [Step 3], was tested on completely new dataset $D_{pv}$ consisted of $N_{pv}$=25 patients and $C_{pv}$=159 cough events. Model was tested for both, performance in classifying cough events into pneumonic and non-pneumonic cough and in separating the patients with pneumonia from non-pneumonic using PCI. Table 24 shows the performance of the selected LRM $\Re^{fc}$ in classifying cough events into Pneumonic and non-pneumonic cough classes.

TABLE 24

Performance of the selected LRM $\Re^{fc}$ on prospective dataset $D_{pv}$ in classifying cough events into classes 'Pneumonic cough' and 'non-pneumonic cough'.

| | Prospective Dataset $D_{pv}$ | | | | | |
|---|---|---|---|---|---|---|
| Selected LRM model | Sens | Spec | Acc | PPV | NPV | K |
| $\Re^{f1}$ ($C_f^s$) | 83% | 58% | 74% | 79% | 64% | 0.42 |
| $\Re^{f2}$ ($C_f^s$ + BrI) | 82% | 60% | 74% | 80% | 64% | 0.42 |
| $\Re^{f3}$ ($C_f^s$ + Fever) | 82% | 78% | 81% | 88% | 69% | 0.58 |
| $\Re^{f4}$ ($C_f^s$ + Age) | 84% | 75% | 81% | 86% | 71% | 0.57 |
| $\Re^{f5}$ ($C_f^s$ + BrI + Fever) | 82% | 69% | 77% | 83% | 67% | 0.50 |
| $\Re^{f6}$ ($C_f^s$ + BrI + Age + Fever) | 88% | 85% | 87% | 92% | 78% | 0.71 |

Table 25 shows the performance of model in classifying patients into pneumonia and non-pneumonia.

TABLE 25

Performance of the selected LRM $\Re^{fc}$ on prospective dataset $D_{pv}$, in diagnosing pneumonia using Pneumonic Cough Index.

| | Prospective Dataset $D_{pv}$ | | | | | |
|---|---|---|---|---|---|---|
| Selected LRM model | Sens | Spec | Acc | PPV | NPV | K |
| $\Re^{f1}$ ($C_f^s$) | 94% | 75% | 88% | 89% | 86% | 0.72 |
| $\Re^{f2}$ ($C_f^s$ + BrI) | 82% | 63% | 76% | 82% | 63% | 0.45 |
| $\Re^{f3}$ ($C_f^s$ + Fever) | 94% | 87.5% | 92% | 94% | 88% | 0.82 |
| $\Re^{f4}$ ($C_f^s$ + Age) | 94% | 75% | 88% | 89% | 86% | 0.72 |
| $\Re^{f5}$ ($C_f^s$ + BrI + Fever) | 88% | 75% | 84% | 88% | 75% | 0.63 |
| $\Re^{f6}$ ($C_f^s$ + BrI + Age + Fever) | 82% | 100% | 88% | 100% | 73% | 0.75 |

For cough classification, model $\Re^{f6}$ (selected cough features along with presence of fever, Age and BrI) achieved the best classification with sensitivity=88% and specificity=85%. $\Re^{f1}$ which used only cough features has sensitivity and specificity of 83% and 58% respectively. In separating pneumonia and non-pneumonia patients, top 3 performing models were $\Re^{f1}$, $\Re^{f3}$, $\Re^{f4}$ and $\Re^{f6}$ all with kappa agreement greater than 0.7, substantial agreement. $\Re^{f1}$ achieved a high sensitivity and specificity of 94% and 75% respectively.

VI. 4. Discussion and Conclusion—$2^{ND}$ Pneumonia Diagnosis Method

The preceding embodiment of the invention provides an automated procedure to diagnose pneumonia using cough sounds. The method is based on initially classifying individual cough events into 'pneumonic cough' and 'non-pneumonic cough' classes and then calculating a Pneumoic Cough Index (PCI) over all the cough events recorded. Working on 599 cough events from 91 pediatric patients diagnosed with a range of respiratory diseases, we showed the method is capable of classifying pneumonia at a sensitivity >90% while holding the specificity at >85%.

As far as the inventors are aware this is the first attempt in the world to develop an objective model for the pneumonia diagnosis centred about cough sounds. The results indicate the feasibility of taking a cough-centred approach in diagnosing pneumonia in resource-poor regions. Furthermore, using features derived from cough only we obtained a sensitivity >90% at a specificity of 75%. Cough can be recorded with non-contact instrumentation, and our algorithms can be implemented on ubiquitous platforms such as smart phones in a form ready to be used by a minimally trained person. The device will not require physical contact with the subject, making sterilization easy and requiring minimal operator training for field use. The technology, in the simplest version, will require between 5-10 cough sounds and will automatically and immediately provide a diagnosis. Such a system is expected to be a paradigm shifting novelty in the field of pneumonia diagnosis in remote regions.

The simplicity of proposed technology and potential low cost implementation on ubiquitous devices make our approach valuable in long term monitoring. It also will have substantial strategic value in developing new vaccines as well management strategies for childhood pneumonia. Clinical trials of new pneumonia vaccines conducted in resource-limited regions of the world require reliable tools to measure the efficacy of intervention. The same is true for assessing the effectiveness of any new pneumonia management strategy targeting large populations. There are no field deployable gold standards to diagnose pneumonia, especially the early stage (non-severe) disease where even chest X-rays file. The existing WHO algorithm is limited due to its low diagnostic performance. While the algorithm serves a very useful role in picking up potential cases of pneumonia, the cost of doing so, the low specificity, makes it difficult to use in assessing the validity of a new intervention.

Automated Cough Classifier Using Logistic Regression

Figure 20:
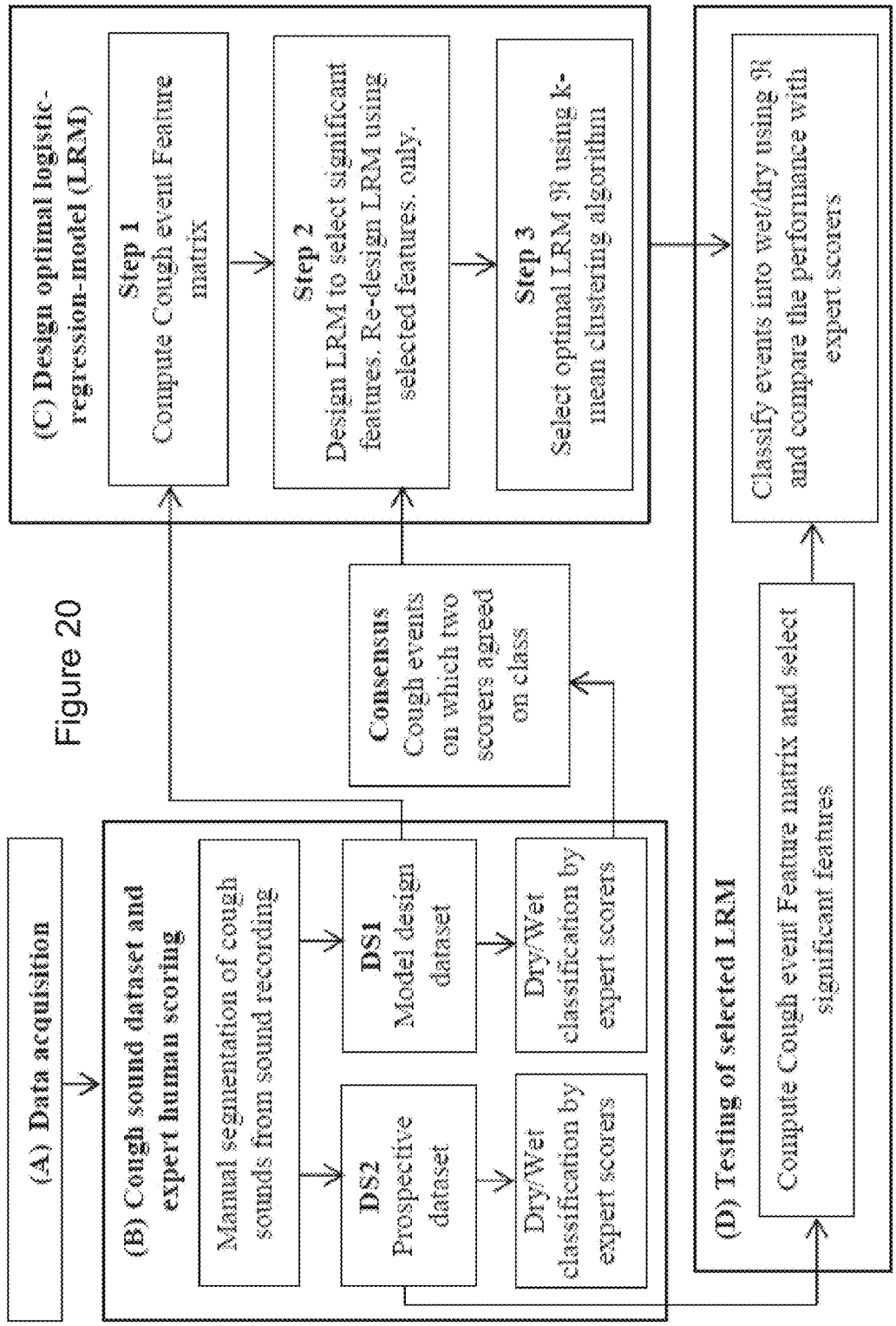
FIG. 20 is a block diagram of an automated cough classification procedure according to a further and preferred embodiment of an aspect of the present invention.

FIG. 20 shows the block diagram of the automated cough classification process according to an embodiment of the invention. It is divided into four stages, (A) data acquisition process (B) creating a cough sound database and classification into wet/dry classes by expert scorer (C) designing of automatic classifier (D) testing of classifier on prospective cough sound dataset. In Section II-A to Section II-D we describe details of the method.

A. Data Acquisition

The clinical data acquisition environment for this work is Respiratory Medicine Unit of the Sardjito Hospital, Gadjah Mada University, Indonesia. Table 26 lists the inclusion and exclusion criteria of subjects.

TABLE 26

Inclusion and Exclusion Criteria for Subjects

| Inclusion Criteria | Exclusion Criteria |
|---|---|
| Patients with symptoms of chest infection: At least 2 of Cough Sputum Increased breathlessness Temperature >37.5° Consent | Advanced disease where recovery is not expected eg terminal lung cancer Droplet precautions NIV required No Consent |

All patients fulfilling the inclusion criteria were approached. An informed consent was made using form approved by the human ethics committees of Gadjah Mada University and The University of Queensland. Patients were recruited within the first 12 hours of their admission. After the initial medical assessment sound recordings were made for next 4-6 hours in the natural environment of the respiratory ward.

Sound recordings were made using two systems,
1. Computerized data acquisition system—A high fidelity system with a professional quality pre-amplifier and A/D converter unit, (Model Mobile-Pre USB, M-Audio, California, USA) and a matched pair of low-noise microphones having a hypercardiod beam pattern (Model NT3, RODE, Sydney, Australia). Adobe audition software version 2 was used to record the sound data on to the laptop computer.—See FIG. 1 for an illustration of this type of arrangement.
2. Portable recording system—A high-end, light-weight portable, 2-AA battery powered audio recorder (Olympus LS-11) with two precision condenser microphones.

In both sound recording systems we used a sampling rate of 44.1 khz with a 16 bit resolution (CD-quality recording). The nominal distance from the microphone to the mouth of the patient was 50 cm, but could vary from 40 cm to 70 cm due to patient movements. For each patient, we also received the final diagnosis as well as all the laboratory and clinical examination results.

B. Cough Sound Dataset and Classification into Wet or Dry by Expert Human Scorers Let N be the number of patients whose sound recording is used and C be total number of cough events from N patients. These C cough events were manually segmented after screening though 6-8 hours of the sound data of each patient. There is no accepted method for automatic marking of start and end of a cough event. Manual marking is still considered the gold standard. After careful listening start and end of all cough events were manually marked.

We divided N patients with C cough events into two datasets, (i) DS1 (model design dataset) and (ii) DS2 (prospective study dataset). The patients were divided into DS1 and DS2 based on the order of presentation to the respiratory clinic of the hospital. Patients in datasets DS1 and DS2 were mutually exclusive.
 (i) DS1—consisted of C1 cough events from N1 patients. Cough events from this dataset were used to design the optimal model.
 ii) DS2—consisted of C2 cough events from N2 patients. Cough events from this dataset were used to test the designed model. Cough events from DS2 were blind to the process of model design.

Two expert scorers having experience of 15-20 years in pediatric respiratory diseases then scored cough events from two datasets into two classes, wet or dry. Scorers were blinded to the subject's history and diagnosis. This manual classification is considered as the reference standard against which results of automatic classification are compared.

C. Design of Cough Sound Classifier

To design a system for automatic classification of cough sounds we used cough events from DS1. Let DS11 be the subset of DS1 containing those cough events on which both scorers agreed on the class of cough sounds. We had C11 cough events in DS11. Use cough events in DS11 to design automatic classifier model. This is a three step process.

[Step 1] Cough event Feature matrix computation: In this step, feature vector containing 'F' mathematical features is computed from each of C11 cough events and a cough event feature matrix '$M_{DS11}$' of size, C11×F was formed. To compute 'F' features from a cough event use below steps.
 (i) Let x denotes a discrete time sound signal from a cough event.
 (ii) Normalize x by dividing it by absolute maximum value.
 (iii) Segment x into 'n' equal size non-overlapping sub-segments. Let $x^i$ represents the $i^{th}$ sub-segment of x, where i=1, 2, 3, . . . , n.
 (iv) Compute following features for each sub-segment and form feature vector containing F features: Bispectrum Score (BGS), Non-gaussianity score (NGS), formant frequencies (FF), Pitch (P), log energy (Log E), zero crossing (ZCR), kurtosis (Kurt), and twelve mel-frequency cepstral coefficients (MFCC).
 (v) Repeat steps (i)-(iii) for all C11 cough events and form cough event feature matrix $M_{DS11}$ of size C11×F.

[Step 2] Automatic classifier design: In a preferred embodiment of the presently described aspect of the invention we used a Logistic-regression model (LRM) as the pattern classifier. LRM is a generalized linear model, which uses several independent predictors to estimate the probability of a categorical event (dependent variable). In this work, the dependent variable Y is assumed to be equal to "one" (Y=1) for wet cough and "zero" (Y=0) for dry cough. A model is derived using regression function to estimate the probability Y=1 (i.e cough event belong to category of 'wet cough') given the independent variables (i.e F features) as follows:

$$Prob(Y = 1 |_{f_1, f_2, f_3, \ldots f_F}) = \frac{e^z}{e^z + 1} \quad (1)$$

$$z = \beta_0 + \beta_1 f_1 + \beta_2 f_2 + \ldots + \beta_n f_F \quad (2)$$

In (1) and (2) $f_1, f_2, \ldots f_F$ are the elements of feature vector (independent variables), $\beta_0$ is called the intercept and $\beta_1, \beta_2$ and so on are called the regression coefficient of independent variables. To select the optimal decision threshold $\lambda$ from Y (that the cough is wet if Y is above $\lambda$ otherwise dry) we used the Receiver-Operating Curve (ROC) analysis.

Use data in matrix $M_{DS11}$ (C11 observations from F independent variables) and adopt leave-1-out cross validation (LOV) technique for LRM design. As the name suggests, LOV technique involves using data from all cough events except one to train the model and one cough event to validate the model. This process was systematically repeated C11 times such that each cough event in DS11 was used as the validation data once. This resulted in $L_{C11}$ number of LRMs.

To evaluate the performance of the designed $L_{C11}$, performance measures such as Sensitivity, Specificity, Accuracy, Positive Predicted Value (PPV), Negative Predicted Value (NPV), Cohen's Kappa (K) statistic were computed. Please see appendix A2 on how to interpret K values.

Design logistic regression model (LRM) for
(i) Feature Selection: Feature selection is a technique of selecting a sub-set of relevant features for building a robust learning model. Theoretically, optimal feature selection requires exhaustive search of all possible subsets of features. However, to do so for large number of features it will be computationally intensive and impractical. Therefore we searched for satisfactory set of features using p-value. In LRM design a p-value is computed for each feature and it indicates how significantly that feature contributed in development of the model. Important features have low p-value. We used this property of LRM to select a reasonable combination of features (independent variables with low p-value) that facilitate the classification, in the model during the training phase. Compute mean p-value for 'F' features over C11 LRMs. Select the features with mean p-value less than $p_{ths}$. Let $F_s$ be the sub-set of selected features from F.
(ii) Robust LRM design: Create a matrix $M'_{DS11}$ of size $C11 \times F_s$ from $M_{DS11}$. Matrix $M'_{DS11}$ is a cough event feature matrix with only selected features $F_s$ from C11 cough events in DS11. Using $M'_{DS11}$ and adopting LOV, retrain C11 LRMs.

[Step 3] Selecting a good model from $L_{C11}$ LRMs: From $L_{C11}$ LRMs we selected one model as the best, using the k-mean clustering algorithm[9] to test on prospective study dataset DS2. In the k-mean clustering algorithm, target is to divide q data points in d-dimensional space into k clusters, so that within the cluster sum of squared distance from the centroid is minimized.

Problem in our hand is to select a good model from the $L_{C11}$ models available to us. To do so we divided $L_{C11}$ models in d-dimensional space into k=2 clusters, i.e. high performance model cluster and low-performance model cluster. We set space dimension d equal to model parameters plus three performance measures (sensitivity, specificity and kappa). Then from the cluster of the high performance models, we selected that model which had the lowest mean square error value with respect to the centroid. Let $\Re$ represent the selected LRM and $\lambda\Re$ is the corresponding probability decision threshold (value determined using ROC curves such that the classifier performance is maximized). Once $\Re$ is chosen, we fix all the parameters of the model and use it for classifying cough sounds in the prospective dataset DS2.

D. Testing of Selected LRM $\Re$

Following the procedure described in section C [Step 1] and using the cough events from dataset DS2, compute the cough event feature matrix $M_{DS2}$ of size $C2 \times F$. C2 is total cough events in DS2 and 'F' is feature vector. Form $M'_{DS2}$ from $M_{DS2}$ by selecting only robust $F_s$ features. Use selected LRM $\Re$ to classify data in $M'_{DS2}$ into classes wet or dry. Decision process of wet/dry class from the output of $\Re$ is as follows:

Let the Output of the $\Re$ to a Given Cough Input is $Y\Re$. Then, the Cough is Classified as Wet if $Y\Re \geq \lambda\Re$ and Dry Otherwise.

Compare the results of automatic classification by $\Re$ with that of expert scorers and compute the performance measures described in section C [Step 2]. All the algorithms were developed using software programming language MATLAB version 7.14.0.739 (R2012a).

Cough Sound Datasets and Agreement Between Expert Scorers

The inventors used sound recording data from N=78 patients (41 were male and 37 were female). The mean age of the subjects was 2 years and 11 month. The age range of the subjects varied from 1 month to 15 years and having diseases such as asthma, pneumonia, bronchitis and rhinopharyngitis. Table 27 gives the demographic and clinical details of the patients.

TABLE 27

Demographic and Clinical Details of the Subject

| GENDER | Male | 41 |
| | Female | 37 |
| AGE | Neonatal | 2 |
| | <12 months | 31 |
| | <60 months | 29 |
| | >=60 months | 16 |
| DIAGNOSIS | Pneumonia | 34 |
| | Pneumonia + other | 21 |
| | Bronchitis | 8 |
| | Asthma | 3 |
| | Rhinopharyngitis | 5 |
| | Asthma + Rhinopharyngitis | 1 |
| | Others | 6 |

From N=78 patients a total of C=536 cough events were analyzed. On the average 7 cough events per patients were analyzed (minimum=2 and maximum=13). Dataset DS1 has C1=385 cough events from N1=60 patients and dataset DS2 has C2=151 cough events from N2=18 patients.

Table 28 shows the contingency table between two scorers in classifying cough sounds from DS1 and DS2, into two classes wet and dry.

TABLE 28

Contingency table between human scorers for classifying coughs into wet/Y. K = 0.56 and % agreement = 80.5% for DS1 and K = 0.54 and % agreement = 77.5 for DS2.

| | | Dataset DS11 | | | | | Dataset DS2 | | |
| | | Scorer 1 | | | | | Scorer 1 | | |
| | | WET | DRY | | | | WET | DRY | |
| Scorer 2 | WET | 82 | 55 | 60% | Scorer 2 | WET | 47 | 23 | 67% |
| | DRY | 20 | 228 | 92% | | DRY | 11 | 70 | 86.4% |
| | | 80.4% | 80.6% | 310 | | | 81% | 75.3% | 117 |

In DS1 out of 385 cough events, scorers agreed C11=310 times (80.5%) on the classes of cough events which were used to form subset DS11. In dataset DS2 they agreed 117 times out of 151 (77.5%). The kappa agreement between Scorer 1 and Scorer 2 is 0.55 for DS1 and 0.54 for DS2. Of the 310 cough events in DS11, 82 belonged to wet class and 228 belonged to dry class. The DS11 cough events were then used to design LRM models described in section II-C.

E. Cough Sound Characteristics in Our Databases

Figure 21:
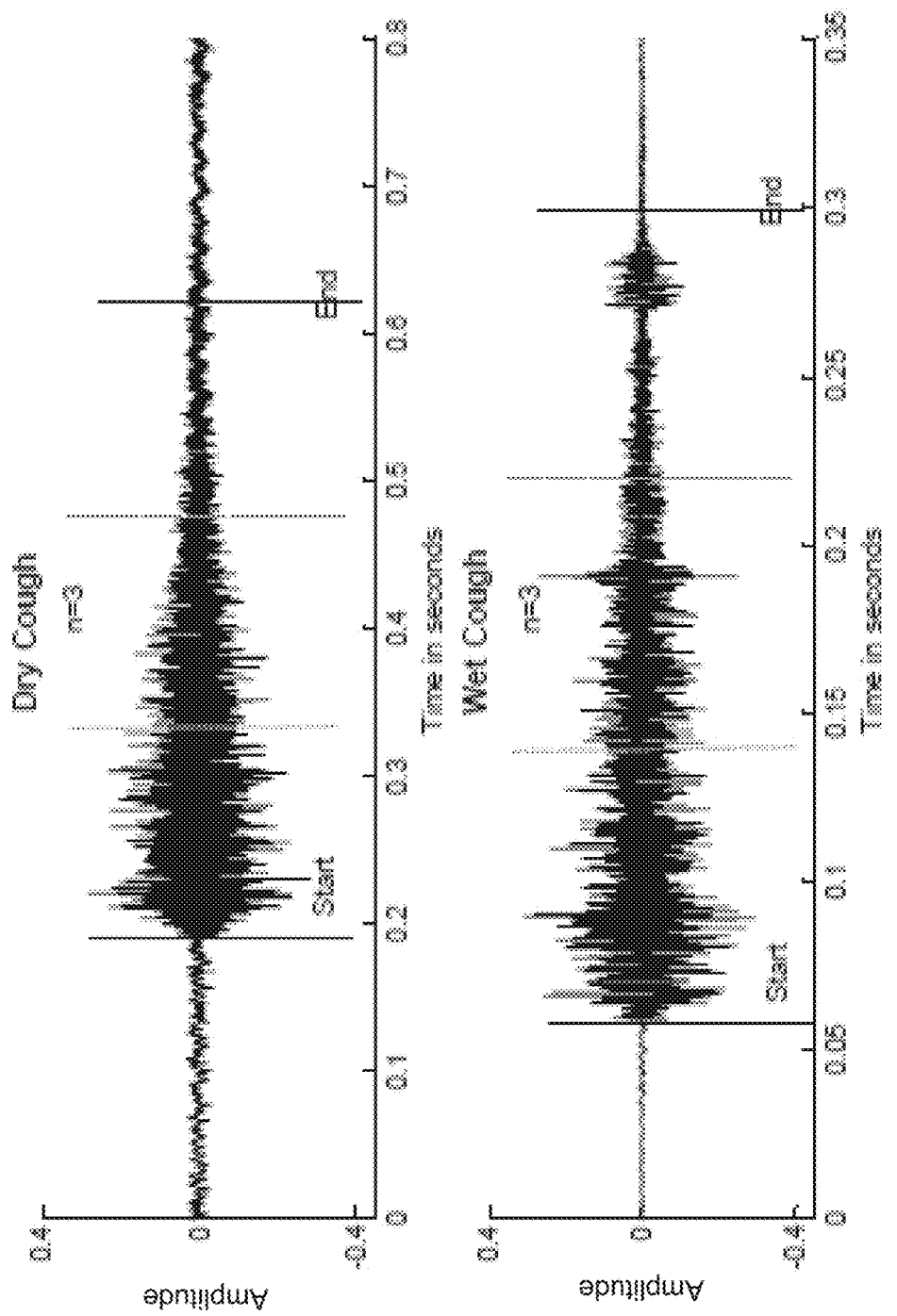
FIG. 21 shows a typical example of dry cough waveform and wet cough waveform from two patients.
Figure 22:
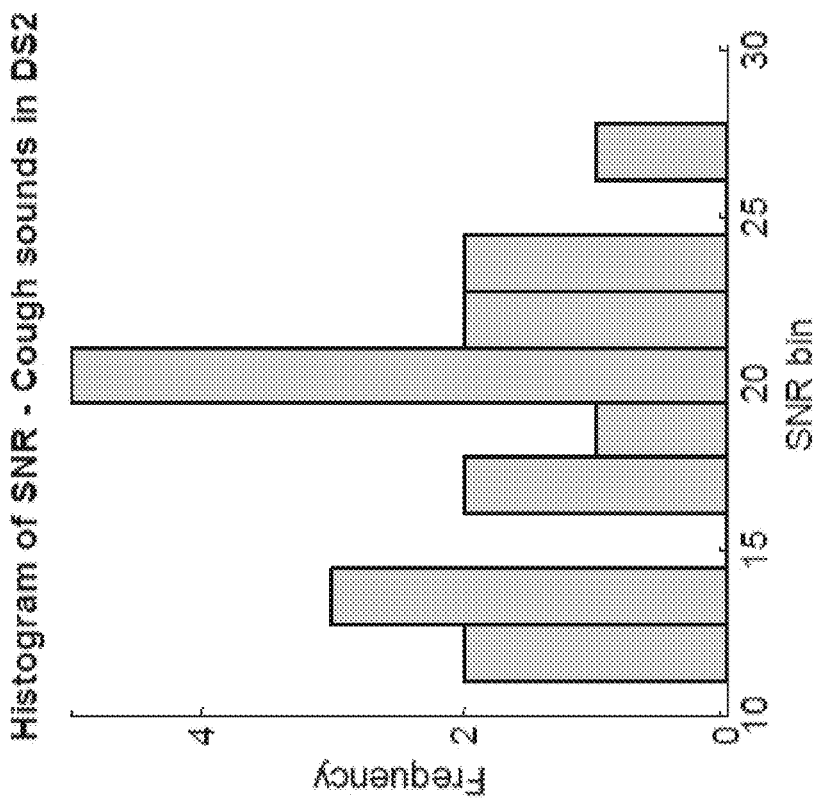
FIGS. 22A and 22B are histograms of SNR for the cough sound.

The mean duration of dry cough in DS11 was 260±77 ms (computed using 228 dry coughs) and that of wet cough was 238±54 ms (computed using 82 wet coughs). FIG. 21 shows a typical example of dry cough waveform and wet cough waveform from two patients, ids #35 & #38 respectively. The cough sound waveforms were generally clean with high signal-to-noise-ratio (SNR). The mean signal to noise ratio for the DS11 was 15.2±5.5 db (maximum=28.65 db and minimum=2.9 db) and that for DS2 was 18.6±4.5 db (maximum=27.8 db and minimum=11.1 db). FIGS. 23A and 22B are histograms of SNR for the cough sound in DS11 and DS2.

Start and end of each coughs were carefully marked by a human operator after listening to cough sounds as shown in the FIG. 21. Following the method given in section II-C-[Step 1] we computed feature matrix $M_{DS11}$. We used n=3 to divide each cough segment into 3 sub-segments. In the literature, clinicians and scientist alike have described cough sounds consisting of 3 phases, (i) initial opening burst, (ii) followed by noisy airflow and last (3) glottal closure[24,25]. It has been shown that these phases carry different significant information specific to quality of cough, wet or dry. On this basis we divided each cough segments into 3 sub-segments. Setting n=3 led to a feature vector F of length 66 consisting of following features (n×12 MFCC)+(n×4 FF)+([n×[BGS, NGS, P, Log E, Zcr, Kurt]). From C11=310 cough events and F=66 features, cough event feature matrix $M_{DS11}$ was created.

F. Automatic Classification using LRM

Feature Matrix and LRM performance during training stage: Following LOV technique, $L_{C11}$=310 LRMs were designed.

The mean training sensitivity and specificity for the 310 LRMs were 92±1% and 93±0.5% respectively. Validation sensitivity and specificity for these models were 62% and 84% respectively. Table 4-(A) gives the detailed classification results when all the F=66 features were used to train the LRMs.

TABLE 29

LRM performance before and after the feature selection. Statistics provided in the table are mean ± standard deviation. 95% confidence interval for mean of the training dataset is provide at bottom. For scorer 1 and scorer 2 sample size is C1 = 385 cough events from N1 = 60 patients in dataset DS1. Out of 385 cough events scorers had wet/dry consensus on C11 = 310 cough events.

| | | Sensitivity | Specificity | Accuracy | PPV | NPV | K |
|---|---|---|---|---|---|---|---|
| (A) When all the features were used to develop LRM | | | | | | | |
| Consensus of scorer 1 & scorer 2 | Training | 91.76 ± 0.68 [91.69-91.84] | 92.65 ± 0.45 [92.6-92.7] | 92.45 ± 0.5 [92.36-92.47] | 81.80 ± 1 [81.68-81.91] | 96.90 ± 0.3 [96.87-96.93] | 0.8125 ± 0.1 [0.8112-0.8138] |
| | Validation | 62 | 84 | 78 | 59 | 86 | 0.46 |
| Scorer 1 wet/dry class | Training | 87.15 ± 0.95 [86.9-87.4] | 87.49 ± 0.89 [87.26-87.72] | 87.40 ± 0.90 [87.17-87.63] | 71.53 ± 1.84 [71-72] | 94.97 ± 0.40 [94.87-95.07] | 0.6977 ± 0.02 [0.69-0.70] |
| | Validation | 53 | 78 | 71 | 47 | 82 | 0.3 |
| Scorer 2 wet/dry class | Training | 81.96 ± 1.01 [81.7-82.23] | 82.24 ± 0.97 [81.98-82.49] | 82.14 ± 0.98 [81.89-82.4] | 71.83 ± 1.37 [71.48-72.19] | 89.18 ± 0.78 [88.98-89.38] | 0.6224 ± 0.01 [0.6173-0.6276] |
| | Validation | 45 | 67 | 59 | 43 | 69 | 0.12 |
| (B) When selected all the features were used to develop LRM | | | | | | | |
| Consensus of scorer 1 & scorer 2 | Training | 87.36 ± 0.61 [87.29-87.43] | 87.82 ± 0.43 [87.77-87.87] | 87.70 ± 0.46 [87.65-87.75] | 72.07 ± 0.87 [71.98-72.17] | 95.07 ± 0.25 [95.05-95.10] | 0.7041 ± 0.01 [0.7029-0.7053] |
| | Validation | 81 | 83 | 82 | 63 | 92 | 0.58 |
| Scorer 1 wet/dry class | Training | 82.75 ± 0.57 [82.60-82.89] | 83.06 ± 0.52 [82.92-83.19] | 82.98 ± 0.52 [82.84-83.11] | 63.78 ± 1.18 [63.47-64.08] | 93.03 ± 0.27 [92.96-93.10] | 0.60 ± 0.01 [0.59-0.60] |
| | Validation | 76 | 79 | 78 | 57 | 90 | 0.5 |
| Scorer 2 wet/dry class | Training | 75.66 ± 0.57 [7.5.51-75.81] | 75.92 ± 0.58 [75.77-76.07] | 75.83 ± 0.57 [75.68-75.98] | 63.44 ± 0.96 [63.19-63.69] | 84.95 ± 0.61 [84.79-85.11] | 0.49 ± 0.01 [0.4916-0.4975] |
| | Validation | 72 | 73 | 72 | 59 | 82 | 0.43 |

Figure 23:
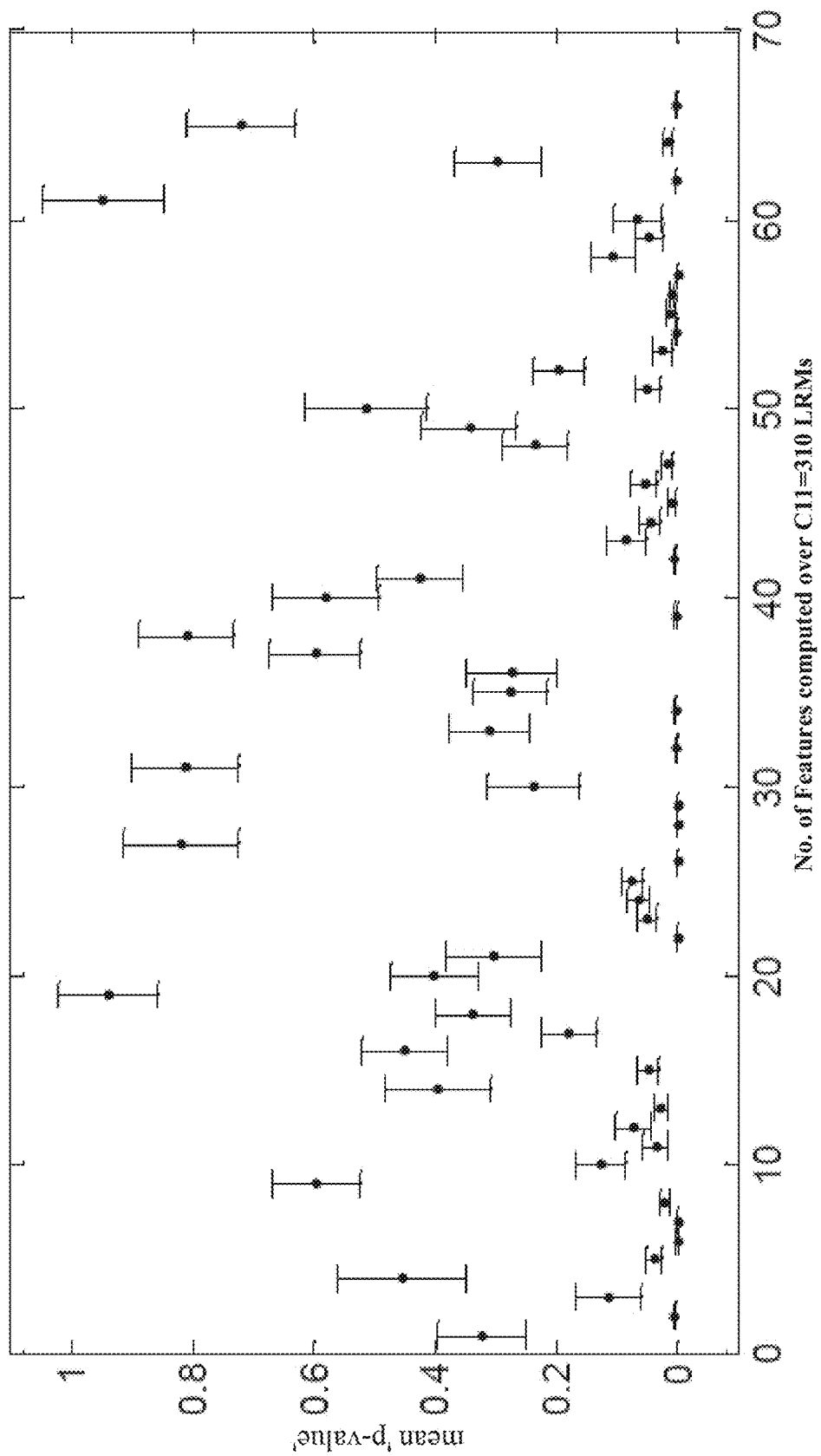
FIG. 23 Shows statistical information used in an analysis and discussion of the method illustrated in FIG. 20.

Following the process described in section II-B [Step 2] and using $p_{ths}$=0.06, we selected $F_s$=31 features. FIG. 23 shows the mean 'p-value' associated with F=66 features computed over C11=310 LRMs. All the features which have mean 'p-value' less than $p_{ths}$=0.06 were selected. The selected features were 1 each from Bispectrum score, kurtosis, and number of zero-crossing, 2 each from non-gaussianity score and log-energy, 5 from formant frequencies, and 19 from mel-frequency cepstral coefficients. Table 30 gives details of the feature selected for designing the final LRM.

TABLE 30

F = 66 features were computed from each cough segment by using n = 3 at section II-C [Step 1]. '✓' indicates that feature was selected for designing the final model at section II-C [Step 2].

| | BSG | | | NGS | | | FF1 | | | FF2 | | | FF3 | | | FF4 | | |
|---|---|---|---|---|---|---|---|---|---|---|---|---|---|---|---|---|---|---|
| Features | 1 | 2 | 3 | 1 | 2 | 3 | 1 | 2 | 3 | 1 | 2 | 3 | 1 | 2 | 3 | 1 | 2 | 3 |
| Selected | | ✓ | | ✓ | ✓ | ✓ | ✓ | | | | ✓ | | ✓ | | | ✓ | | |
| | Pitch | | | LogE | | | Kurt | | | ZCR | | | MFCC0 | | | MFCC1 | | |
| Features | 1 | 2 | 3 | 1 | 2 | 3 | 1 | 2 | 3 | 1 | 2 | 3 | 1 | 2 | 3 | 1 | 2 | 3 |
| Selected | | | | ✓ | ✓ | | | ✓ | | ✓ | | | | ✓ | | ✓ | | |
| | MFCC2 | | | MFCC3 | | | MFCC4 | | | MFCC5 | | | MFCC6 | | | MFCC7 | | |
| Features | 1 | 2 | 3 | 1 | 2 | 3 | 1 | 2 | 3 | 1 | 2 | 3 | 1 | 2 | 3 | 1 | 2 | 3 |
| Selected | | ✓ | ✓ | | ✓ | | ✓ | ✓ | ✓ | ✓ | | | | ✓ | | | ✓ | ✓ |
| | MFCC8 | | | MFCC9 | | | MFCC10 | | | MFCC11 | | | | | | | | |
| Features | 1 | 2 | 3 | 1 | 2 | 3 | 1 | 2 | 3 | 1 | 2 | 3 | | | | | | |
| Selected | ✓ | ✓ | ✓ | ✓ | | | | ✓ | | ✓ | | ✓ | | | | | | |

According to this table MFCC based features were most dominant. Out of 31 selected features, 19 features were contributed from different MFCC components. After MFCC formant frequencies made second most dominant contribution with 5 features. Moreover except for $4^{th}$ formant frequency and pitch based features, which were completely omitted, all other features contributed with features from at-least one sub-segment towards building of final LRM model.

When only selected features $F_s$ were used to re-train LRMs, mean training sensitivity and specificity were recorded as 87±1% and 88±0.5% respectively and validation sensitivity and specificity were 81% and 83%. The validation kappa agreement between the LRM and scorers was 0.46 when all the features were used to train LRM and it increased to 0.58 when only selected features were used. Table 29-(B) gives the detailed training and validation results after feature selection.

Selection of LRM ($\Re$): From $L_{C11}$=310 designed LRMs using data from DS11, optimal model $\Re$ was selected using k-mean clustering method as discussed in section II-C-[Step 3]. Models were clustered into two groups, high performance model and low performance models based on model parameters and performance measures. Of 310 models, 202 were clustered in high performance model group and 108 into low performance model group. LRM model #26 has the lowest mean square error value with respect to centroid of the high performance models. This model $\Re$ was chosen and all its parameters were fixed for future use. $\Re$ was tested on prospective dataset DS2.

Performance of $\Re$ on prospective dataset DS2: Table 31 gives the classification results of $\Re$ against expert scorers.

TABLE 31

Performance of $\Re$ on dataset DS2 prospective study dataset.

| | Sensitivity | Specificity | Accuracy | PPV | NPV | K |
|---|---|---|---|---|---|---|
| Against individual scorer when tested on all the cough events (151) from DS2 | | | | | | |
| Scorer 1 | 77.5% | 76% | 76% | 54% | 90% | 0.47 |
| Scorer 2 | 75% | 64% | 67% | 43% | 87% | 0.31 |
| Tested on only those events when both Scorer 1 and Scorer 2 agreed on class | | | | | | |
| | 84% | 76% | 78% | 55% | 93% | 0.51 |

When Scorer 1, wet/dry classification was used as reference standard, $\Re$ has the sensitivity of 77.5%, specificity of 76% and kappa agreement of 0.47. For the Scorer 2, results were sensitivity 75%, specificity 64% and kappa 0.31. When model $\Re$ was tested on only those events, in which Scorer 1 and Scorer 2 agreed on classification (117 cough events), sensitivity jumped to 84% and kappa value to 0.51. Table 32 shows the contingency table.

TABLE 32

Contingency table for selected LRM tested on dataset DS2. K = 0.51.

| | | Scorers | | |
|---|---|---|---|---|
| | | W | nW | |
| LRM | W | 26 | 21 | 55% |
| | nW | 5 | 65 | 93% |
| | | 84% | 76% | 78% |

LRM results when matched for Age and Gender: Table 33 shows the performance of the LRM on DS11 and DS2 when matched for age and gender.

TABLE 33

LRM validation results for dataset DS11 and prospective dataset DS2 with age and gender matched.

| | Sensitivity | Specificity | Accuracy | PPV | NPV | K |
|---|---|---|---|---|---|---|
| (A) Validation results for dataset DS11. All the features were used to train the LRM ||||||||
| Age <=60 months, Male (#121 cough events) | 59% | 83% | 76% | 57% | 84% | 0.41 |
| Age <=60 months, Female (#145 cough events) | 58% | 88% | 80% | 63% | 85% | 0.47 |
| Age >60 months, Male (#20 cough events) | 89% | 64% | 75% | 67% | 87.5% | 0.51 |
| Age >60 months, Female (#24 cough events) | 100% | 83% | 83% | 20% | 100% | 0.28 |
| Validation results for dataset DS11. Selected features were used to train the LRM ||||||||
| Age <=60 months, Male (#121 cough events) | 73.5% | 78% | 77% | 57% | 88% | 0.47 |
| Age <=60 months, Female (#145 cough events) | 84% | 87% | 86% | 70% | 94% | 0.67 |
| Age >60 months, Male (#20 cough events) | 89% | 64% | 75% | 67% | 87.5% | 0.51 |
| Age >60 months, Female (#24 cough events) | 100% | 91% | 92% | 33% | 100% | 0.47 |
| (B) Prospective Study dataset DS2 ||||||||
| Age <=60 months, Male (#36 cough events) | 92% | 87.5% | 89% | 78.5% | 95% | 0.76 |
| Age <=60 months, Female (#27 cough events) | 87.5% | 95% | 92.5% | 87.5% | 95% | 0.82 |
| Age >60 months, Male (#30 cough events) | 50% | 54% | 53% | 14% | 87.5% | 0.02 |
| Age >60 months, Female (#24 cough events) | 86% | 71% | 75% | 54.5% | 92% | 0.48 |

Due to limited availability of data we considered only 4 divisions; (i) male with age<=60 months, (ii) female with age<=60 months, (iii) male with age>60 months and (iv) female with age>60 months. According to this table during the model designing stage, generally no significance difference was seen in the model validation performance across four divisions in comparison to when no division was considered, table 29 & table 33(A). Similar to this on the prospective dataset DS2, selected model $\Re$ performed well across all division (table 31 & table 33(B)), except in the $3^{rd}$ division (male with age>60) where performance were very poor.

Embodiments of the present invention encompass an automated, objective method to classify cough sounds in to wet and dry categories. As far as the inventors are aware know, this is the first attempt to develop objective technology for the dry/wet classification of pediatric cough sounds, especially in diseases such as pneumonia. The results presented herein are based on 536 cough events from 78 subjects, compared to existing work which use no more than 30 coughs in their descriptive analyses. For these reasons no other work has been available to directly compare the results against.

The reference method used for the assessment of our technology is the subjective classification of cough sounds into wet/dry classes by two pediatric respiratory physicians from different countries. These scorers were blinded to the actual clinical diagnosis of the subjects. In an event-by-event cough classification, the two experts agreed with each other at a Moderate Level (kappa value of $\kappa=0.54$). In[5], inter-clinician agreement for wet/dry cough is reported as $\kappa=0.88$. However it should be noted that, in[5] clinicians assessed wetness of cough at the patient level but not at individual cough level. When we computed the agreement between scorers at the patient level, the kappa value increased to $\kappa=0.66$ (Substantial Agreement). These numbers further illustrate the subjective nature of dry/wet classification.

Our classifier technology was trained on coughs from the training set (set DS1) using only events where both scorers reached consensus. As the output of the training process we identified a good Logistic Regression Model ($\Re$) and fixed its parameters. The model was then tested on the Prospective Set (Set DS2) in several different ways. The highest sensitivity and specificity (84% and 76%) of classification were achieved when we tested $\Re$ against consensus events within DS2. It is interesting to note that these numbers were consistently higher than what we got by testing against individual classification outcomes of each scorer.

Another salient feature of our method is that it has a high negative predictive value (NPV=93%), when scorer consensus data is used as the ground truth. This means that if the model classifies a cough as non-wet (dry), it is most likely that the two expert scorers would independently reach the same conclusion. However, the positive predictive value of our method compared to human scorers is lower (PPV=55%). Thus, a sizable fraction of coughs classified by the model as wet ends up being consensus-classified as dry by human scorers. This phenomenon appears to be explained by the results presented by Chang et. al[5] which found that expert human scorers underscore wet coughs. In[5] they systematically compared subjective dry/wet classifications of expert clinicians with bronchoscopic indications of airway mucus. They reported that clinician's classification of dry cough do not necessarily indicate the absence of secretions. Certain situations in airways, for instance small amounts of secretions, may not be reflected in cough sounds at a sufficient magnitude to be detected by a human observer. One of the possible reasons for a lower PPV value found in our method can be this weakness in the gold standard, human scorers, used to generate our performance statistics. This hypothesis needs to be carefully validated against bronchoscopic findings in the future.

The ability to correctly detect airway mucus can be particularly important in the management of suppurative lung diseases[3,5]. Cough is an early symptom of diseases such as pneumonia, bronchitis and bronchiolitis. The accurate assessment of this symptom is a crucial factor in diagnosing acute diseases or the monitoring of chronic symptoms and treatment efficacy. It is known that in children, wet coughs are more likely to be associated with lower respiratory tract infections[3]. The subjective classification of wet coughs has low sensitivity as a method of detecting airway mucus, even in the hands of expert clinicians. Accurate, objective technology for the classification of dry/wet coughs is currently unavailable either at the commercial or research levels. To the best of our knowledge, this work is the first attempt in the world to develop such technology.

We present the first ever approach to automate dry-wet classification of coughs. The results that have been presented herein can be improved by systematically optimizing the parameters and fine tuning the training processes of the classifier. The heuristic model selection process that has been discussed makes the reported results pessimistic estimates. The inventors also believe that the feature set can be improved and the classification accuracy of the method can be further increased. However before an optimization attempt, issue we need to resolve is to improve the 'gold standard' used in the clinical diagnosis. A carefully controlled bronchoscopy study will be best suited as the gold standard.

Another possible limiting factor to this study is the biasedness of the cough sound database towards dry coughs; almost 70% cough sounds are dry as perceived by expert human scorers. However, with all these factors, embodiments of the present invention can currently classify wet and dry coughs with high sensitivity (84%) and specificity (76%) and with a good agreement ($\kappa=0.51$) with the expert human scorers.

In light of the above it will be realized that methods according to embodiments of the invention described herein can classify the cough sounds into dry and wet classes with high accuracy and good agreement with pediatricians. To the best of the inventors' knowledge it is the first known method for wet/dry classification, presented with complete training and testing results on significantly large cough samples. It is also the first effort to automate the wet/dry classification in pediatric population with range of respiratory infectious diseases. It carries the potential to develop as a useful clinical tool for long term cough monitoring and in the assessment of treatment efficacy or in characterizing the lower respiratory tract infections. It will be essentially useful in clinical or research studies where temporal patterns of cough quality (wet/dry) from hour to hour basis are needed.

The methods described herein may be simultaneously implemented with other potential technologies such as microwave imaging and ultrasound imaging that may be capable of detecting consolidations and mucus in lungs.

Explanations of some of the terms used in explaining the previous embodiment are as follows:

[A2]. Kappa statistic is widely used in situations where the agreement between two techniques should be compared. Below are the guidelines for interpreting the Kappa values.

| Kappa | Interpretation |
| --- | --- |
| <0 | less than chance agreement |
| 0.01-0.20 | Slight agreement |
| 0.21-0.40 | Fair agreement |
| 0.41-0.60 | Moderate agreement |
| 0.61-0.80 | Substantial agreement |
| 0.81-1 | Almost perfect agreement |

[A3]. Definition of the statistical measures used to evaluate the performance of the LRM.
True Positive (TP)—Wet cough correctly identified as 'WET' by LRM.
False Positive (FP)—Dry cough incorrectly identified as 'WET' by LRM.
True Negative (TN)—Dry cough correctly identified as 'DRY by LRM.
False Negative (FN)—Wet cough incorrectly identified as 'DRY' by LRM.

$$\text{Accuracy} = \frac{TP + TN}{TP + FP + TN + FN} \qquad 10$$

$$\text{Sensitivity} = \frac{TP}{TP + FN} \qquad 11$$

$$\text{Specificity} = \frac{TN}{TN + FP} \qquad 12$$

A preferred embodiment of one aspect of the invention comprises a method which is capable of extracting cough sounds from a recording by defining the beginning and the end of the cough segments. A set of different features were computed from the sound signal and used as an input to a decision engine, for example an adaptive neural network-based pattern recognition algorithm or a logistic regression model. In one embodiment the proposed method achieved segmentation sensitivity and specificity of about 95%. This method can be used as the front-end of cough analysis system; hence the quantitative and qualitative information from a larger number of cough sounds in a recording can be analyzed automatically.

According to a preferred embodiment of a further aspect of the invention a method of operating a computational device to process a sound recording of a patient for diagnosis of a particular disease state of the patient is provided. For example, as discussed in detail herein, the disease state may comprise pneumonia.

REFERENCES

[1] A. J. Hotaling and G. T. Moynihan, "Cough," in *Pediatric Otolaryngology*. vol. 2, ed Philadelphia: Saunders, 2003, pp. 1395-1404.

[2] R. E. Black, et al., "Global, regional, and national causes of child mortality in 2008: a systematic analysis," *The Lancet*, vol. 375, pp. 1969-1987, 2010.

[3] Igor Rudan, et al., "Epidemiology and etiology of childhood pneumonia," *Bulletin of the World Health Organization*, vol. 86, pp. 408-416, 2008.

[4] WHO, "WHO-recommended standards for surveillance of selected-preventable diseases," Geneva, WHO/V&B/03.01, 2003.

[5] S. Barry, et al., "The automatic recognition and counting of cough," *Cough*, vol. 2, p. 8, 2006.

[6] S. Matos, et al., "An Automated System for 24-h Monitoring of Cough Frequency: The Leicester Cough Monitor," *Biomedical Engineering, IEEE Transactions on*, vol. 54, pp. 1472-1479, 2007.

[7] PDA Cortex. (accessed at 12 Oct. 2011). *LifeShirt a new era in ambulatory monitoring.* Available: http://www.pdacortex.com/VivoMetrics.htm.

[8] J. Thomas. (accessed at 12 Oct. 2011). *VitaloJAK Cough Monitor.* Available: http://www.trustech.org.uk/case-study/the-vitalojak/

[9] KarmelSonix. (accessed at 12 Oct. 2011). *PulmoTrack.* Available: http://www.karmelsonix.com/solution-pulmotrack.html

[10] M. A. Coyle, et al., "Evaluation of an ambulatory system for the quantification of cough frequency in patients with chronic obstructive pulmonary disease," *Cough*, vol. 1, p. 3, 2005.

[11] E. Vizel, et al., "Validation of an ambulatory cough detection and counting application using voluntary cough under different conditions," *Cough*, vol. 6, p. 3, 2010.

[12] K. McGuinness, et al., "Automated cough detection: a novel approach [abstract]," *Am J Resp Crit Care Med*, p. 175: A381, 2007.

[13] J. Smith and A. Woodcock, "New Developments in the Objective Assessment of Cough," *Lung*, vol. 186, pp. 48-54, 2008.

[14] S. Ferrari, et al., "Cough sound analysis to identify respiratory infection in pigs," *Computers and Electronics in Agriculture*, vol. 64, pp. 318-325, 2008.

[15] R. Martin, "Noise power spectral density estimation based on optimal smoothing and minimum statistics," *Speech and Audio Processing, IEEE Transactions on*, vol. 9, pp. 504-512, 2001.

[16] S. Greenberg, et al., *Speech processing in auditory system.* New York: Springer, 2004.

[17] S. Chatterjee and W. B. Kleijn, "Auditory model based modified MFCC features," in *Acoustics Speech and Signal Processing (ICASSP), 2010 IEEE International Conference on*, 2010, pp. 4590-4593.

[18] W. D. Duckitt, et al., "Automatic detection, segmentation and assessment of snoring from ambient acoustic data," *Physiological Measurement*, vol. 27, p. 1047, 2006.

[19] E. Goldshtein, et al., "Automatic Detection of Obstructive Sleep Apnea Using Speech Signals," *Biomedical Engineering, IEEE Transactions on*, vol. 58, pp. 1373-1382, 2011.

[20] S. K. Asela, et al., "Multi-feature snore sound analysis in obstructive sleep apnea-hypopnea syndrome," *Physiological Measurement*, vol. 32, p. 83, 2011.

[21] U. R. Abeyratne, et al., "Multi-parametric analysis of snore sounds for the community screening of sleep apnea with non-gaussianity index," US patent, 2010.

[22] J. E. Markel and A. H. Gray, *Linear Prediction of Speech*: Springer-Verlag New York, Inc., 1982.

[23] H. Ghaemmaghami, et al., "Normal probability testing of snore signals for diagnosis of obstructive sleep apnea," in *Engineering in Medicine and Biology Society, 2009. EMBC 2009. Annual International Conference of the IEEE*, 2009, pp. 5551-5554.

[24] S. El Safty and A. El-Zonkoly, "Applying wavelet entropy principle in fault classification," *International Journal of Electrical Power & Energy Systems*, vol. 31, pp. 604-607, 2008.

[25] G. M. Foody, "Using prior knowledge in artificial neural network classification with a minimal training set," *International Journal of Remote Sensing*, vol. 16, pp. 301-312, 1995/01/01 1995.

[26] A. Waibel, et al., "Phoneme recognition using time-delay neural networks," *Acoustics, Speech and Signal Processing, IEEE Transactions on*, vol. 37, pp. 328-339, 1989.

[27] M. Riedmiller and H. Braun, "A direct adaptive method for faster backpropagation learning: the RPROP algorithm," in *Neural Networks, 1993, IEEE International Conference on*, 1993, pp. 586-591 vol. 1.

[28] V. Tyagi, et al., "A variable-scale piecewise stationary spectral analysis technique applied to ASR," in *Machine learning for multimodal interaction*, Edinburgh, 2005, pp. 274-284.

[29] 1. Ghaemmaghami, H., U. Abeyratne, and C. Hukins. *Normal probability testing of snore signals for diagnosis of obstructive sleep apnea.* 2009: IEEE.

[30]. Ng, A. K., et al., *Could formant frequencies of snore signals be an alternative means for the diagnosis of obstructive sleep apnea?* Sleep medicine, 2008. 9(8): p. 894-898.

[31] Oppenheim, A. V., R. W. Schafer, and J. R. Buck, *Discrete-time signal processing.* Vol. 1999. 1989: Prentice hall Englewood Cliffs, N.J.:

[32] Zheng, F., G. Zhang, and Z. Song, *Comparison of different implementations of MFCC.* Journal of Computer Science and Technology, 2001. 16(6): p. 582-589.

[33] Abeyratne, U. *Blind reconstruction of non-minimum-phase systems from 1-D oblique slices of bispectrum.* 1999: IET.

[34] Mendel, J. M., *Tutorial on higher-order statistics (spectra) in signal processing and system theory: Theoretical results and some applications.* Proceedings of the IEEE, 1991. 79(3): p. 278-305.

3. Tessa Wardlaw, E. W. Johansson, and M. Hodge, *Pneumonia: The forgotten killer of children.* UNICEF/WHO, 2006.

4. Berman, S., E. Simoes, and C. Lanata, *Respiratory rate and pneumonia in infancy.* Archives of disease in childhood, 1991. 66(1): p. 81-84.

5. WHO, *Childhood disease*, WHO.

6. Cardoso, M. R. A., et al., *Adding fever to WHO criteria for diagnosing pneumonia enhances the ability to identify pneumonia cases among wheezing children.* Archives of disease in childhood, 2011. 96(1): p. 58.

7. Harari, M., et al., *Clinical signs of pneumonia in children.* The Lancet, 1991. 338(8772): p. 928-930.

8. Lozano, J., et al., *Clinical predictors of acute radiological pneumonia and hypoxaemia at high altitude.* Archives of disease in childhood, 1994. 71(4): p. 323-327.

9. Mulholland, E., et al., *Standardized diagnosis of pneumonia in developing countries.* The Pediatric infectious disease journal, 1992. 11(2): p. 77.

10. Palafox, M., et al., *Diagnostic value of tachypnoea in pneumonia defined radiologically.* Archives of disease in childhood, 2000. 82(1): p. 41-45.

Any embodiment of the invention is meant to be illustrative only and is not meant to be limiting to the invention. Therefore, it should be appreciated that various other changes and modifications can be made to any embodiment described without departing from the spirit and scope of the invention.

In the present specification and claims, the word "comprising" and its related and derivative terms, including "comprises" and "comprise", are to be interpreted in an inclusive sense as including each of the stated integers but without excluding the inclusion of one or more further integers.

The invention claimed is:

1. A method of operating a computational device to process patient sounds for diagnosing a respiratory disease, the method comprising:
   having a sound receiving device configured to receive the patient sounds from a patient and form a corresponding digitized sound signal;
   computing feature vectors for each of a plurality of sub-blocks of the digitized sound signal including two or more of: Mel-frequency cepstral coefficients (MFCCs), entropy features, Zero Crossing Rate, and Non-Gaussianity;
   operating a trained cough detection pattern classifier to respond to the feature vectors to produce a cough detection pattern classifier output signal;
   filtering said output signal to produce a smoothed output signal;
   thresholding the smoothed output signal to identify candidate cough segments in the digitized sound signal;
   classifying candidate cough segments to be cough segments based upon their duration being longer than a minimum cough length and shorter than a maximum cough length;
   forming a plurality of sub-segments of each of the cough segments and computing feature vectors for each of the sub-segments, these feature vectors including two or more of: Mel-frequency cepstral coefficients (MFCCs), entropy features, Zero Crossing Rate, and Non-Gaussianity features;
   applying said feature vectors of the plurality of sub-segments to a trained diseased cough pattern classifier to classify each of the cough segments as being one of diseased and non-diseased for a particular respiratory disease;
   computing a diseased cough index indicating a proportion of cough segments classified as diseased relative to all of the cough segments;
   deeming the patient to be suffering from the particular respiratory disease based on the diseased cough index; and
   presenting a diagnosis of the particular respiratory disease on a display under control of the computational device.

2. A method according to claim 1, wherein the forming a plurality of sub-segments of the cough segments comprises forming three sub-segments.

3. A computational device including at least one electronic processor in communication with an electronic memory containing instructions for the processor to carry out a method according to claim 1.

4. A computational device according to claim 3, wherein the computational device comprises a mobile telephone that is programmed to carry out said method.

5. A method according to claim 1, wherein the computing feature vectors for each of a plurality of sub-blocks of the digitized sound signal includes extracting any one of the following groups of features:
   MFCCs and Formant Frequency and Zero Crossing Rate and Shannon Entropy and Non-Gaussianity features; or
   Zero Crossing Rate and Shannon Entropy and Non-Gaussianity features; or
   MFCCs and Zero Crossing Rate and Formant frequency and Non-Gaussianity features.

6. A method according to claim 1, wherein the trained cough detection pattern classifier comprises an artificial neural network.

7. A method according to claim 6, wherein the artificial neural network comprises a time delay neural network (TDNN).

8. A method according to claim 7, wherein the TDNN has a hidden layer between an output layer and an input layer with 10 to 50 neurons in the hidden layer.

9. A method according to claim 1, further comprising applying higher order statistical analysis to the cough segments for further classification of the cough segments.

10. A method according to claim 9, wherein the higher order statistical analysis comprises calculating a bispectrum.

11. A method according to claim 1, wherein the forming a plurality of sub-segments of each of the cough segments and computing feature vectors for each of the sub-segments further comprises:
    determining one or more of: Bispectrum Index (BSG), Formants Frequencies (FF), Log energy (Log E), and Kurtosis (Kurt) features for each of the cough sub-segments.

12. A method according to claim 11, wherein the trained diseased cough pattern classifier comprises any one of: a logistic regression model; an artificial neural network; a Bayes classifier; a hidden Markov model; and a support vector machine.

13. A method according to claim 12,
    wherein the trained diseased cough pattern classifier has been trained with a training set that includes non-pneumonic sounds recorded from patients suffering from one or more of the following complaints: Asthma, Bronchitis, Rhinopharyngitis, wheezing, tonsilopharanzitis, heart disease, larangomalaysia, malaria, and foreign body inhalation.

14. A method according to claim 1, wherein the trained diseased cough pattern classifier comprises any one of: a logistic regression model; an artificial neural network; a Bayes classifier; a hidden Markov model; and a support vector machine.

15. A method according to claim 14,
    wherein the trained diseased cough pattern classifier has been trained with a training set that includes non-pneumonic sounds recorded from patients suffering from one or more of the following complaints: Asthma, Bronchitis, Rhinopharyngitis, wheezing, tonsilopharanzitis, heart disease, larangomalaysia, malaria, and foreign body inhalation.

16. A method according to claim 1, wherein the particular respiratory disease comprises pneumonia.

17. A method according to claim 16, wherein the diseased cough index is a pneumonic cough index.

18. A method according to claim 1, wherein the presenting of the diagnosis of the disease related state on the display comprises presenting a diagnosis of pneumonia.

19. A method according to claim 1, wherein the patient sounds are acquired with one or more microphones that are removed from physical contact with the patient.

* * * * *